(12) United States Patent
Zuk, Jr.

(10) Patent No.: US 6,379,625 B1
(45) Date of Patent: Apr. 30, 2002

(54) APPARATUS COMPRISING A DISPOSABLE DEVICE AND REUSABLE INSTRUMENT FOR SYNTHESIZING CHEMICAL COMPOUNDS, AND FOR TESTING CHEMICAL COMPOUNDS FOR SOLUBILITY

(76) Inventor: Peter Zuk, Jr., 258 Old Littleton Rd., Harvard, MA (US) 01451

( * ) Notice: Subject to any disclaimer, the term of this patent is extended or adjusted under 35 U.S.C. 154(b) by 0 days.

(21) Appl. No.: 09/470,909

(22) Filed: Dec. 23, 1999

(51) Int. Cl.⁷ .............................. B01L 3/00; B01L 3/02; B01J 19/08; B01J 19/12; B01J 10/00; G01N 1/10; B01F 13/08
(52) U.S. Cl. ................... 422/101; 422/99; 422/186.1; 422/186.01; 422/187; 422/100; 436/180; 366/273; 366/274
(58) Field of Search ................... 422/99, 101, 102, 422/104, 130, 186.01, 186.1, 187; 366/273, 274; 436/180

(56) References Cited

U.S. PATENT DOCUMENTS

| | | | | |
|---|---|---|---|---|
| 4,111,754 A | * | 9/1978 | Park ............................ | 195/127 |
| 4,734,262 A | * | 3/1988 | Bagshawe ..................... | 422/101 |
| 4,895,706 A | * | 1/1990 | Root et al. .................... | 422/102 |
| 4,902,481 A | * | 2/1990 | Clark et al. ................... | 422/101 |
| 5,116,496 A | * | 5/1992 | Scott ........................... | 210/232 |
| 5,227,137 A | * | 7/1993 | Monti et al. .................. | 422/101 |
| 5,972,694 A | * | 10/1999 | Mathus ....................... | 435/288.4 |
| 6,054,100 A | * | 4/2000 | Stanchfield et al. .......... | 422/102 |

* cited by examiner

Primary Examiner—Jill Warden
Assistant Examiner—Brian R Gordon

(57) ABSTRACT

An apparatus for mixing a solvent with a solute to form a solution, and for separating said solution from excess solute so that a sample of solution less excess solute can be obtained, and for synthesizing drug compounds.

39 Claims, 44 Drawing Sheets

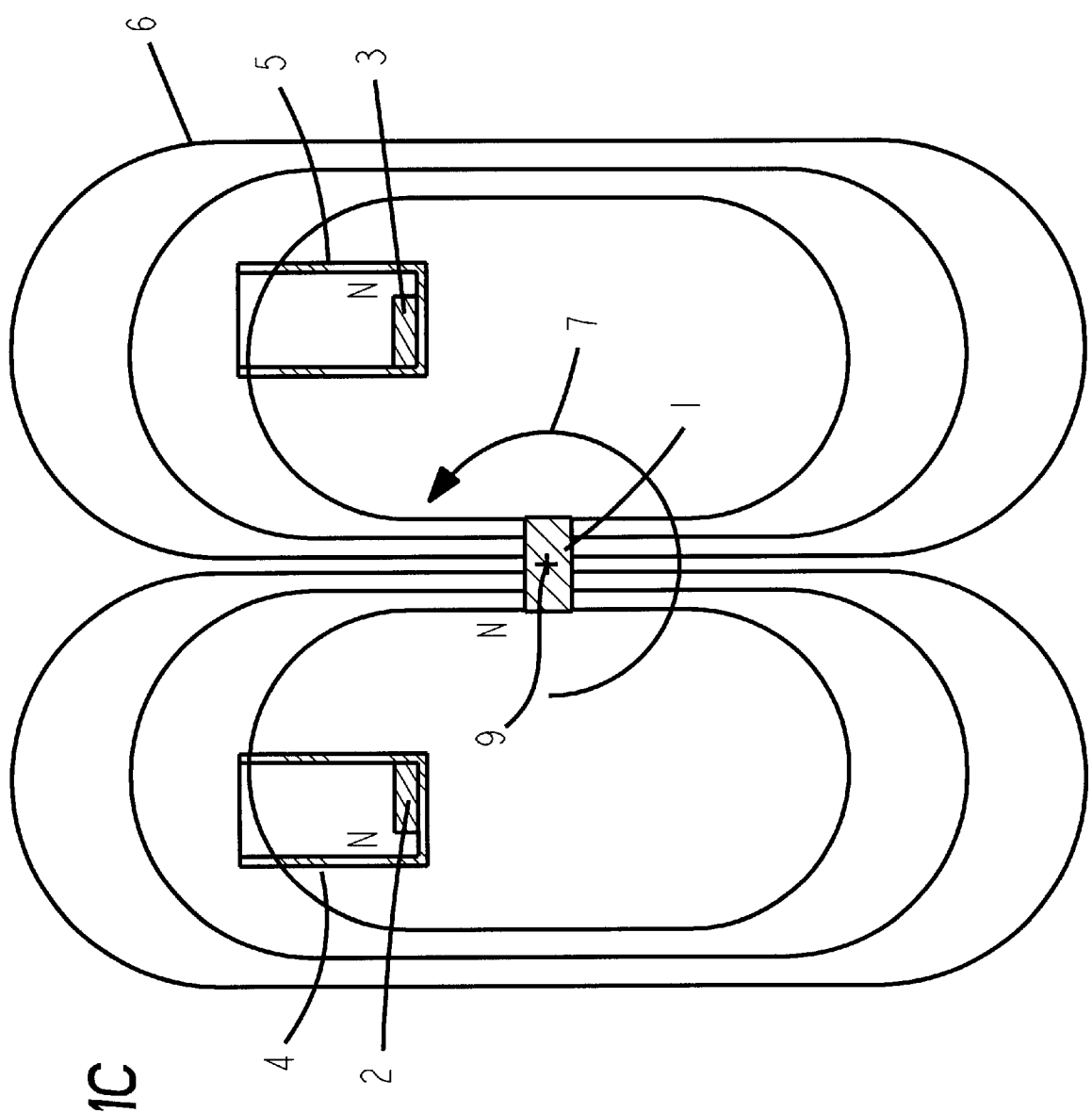

Fig. 5

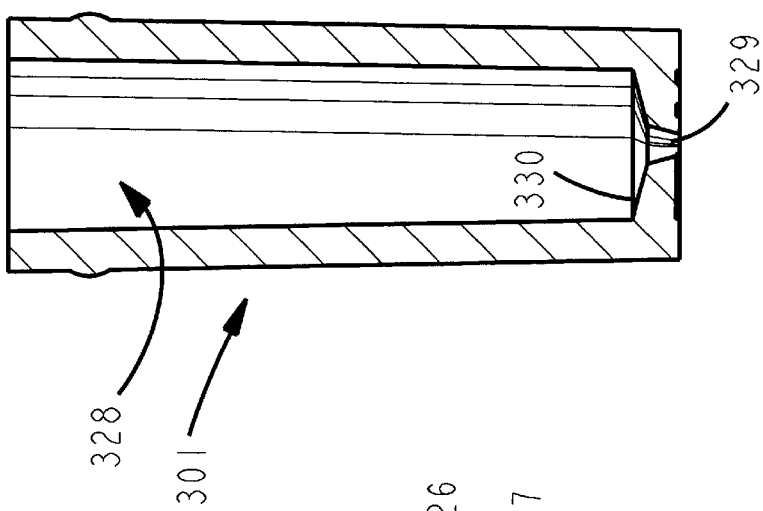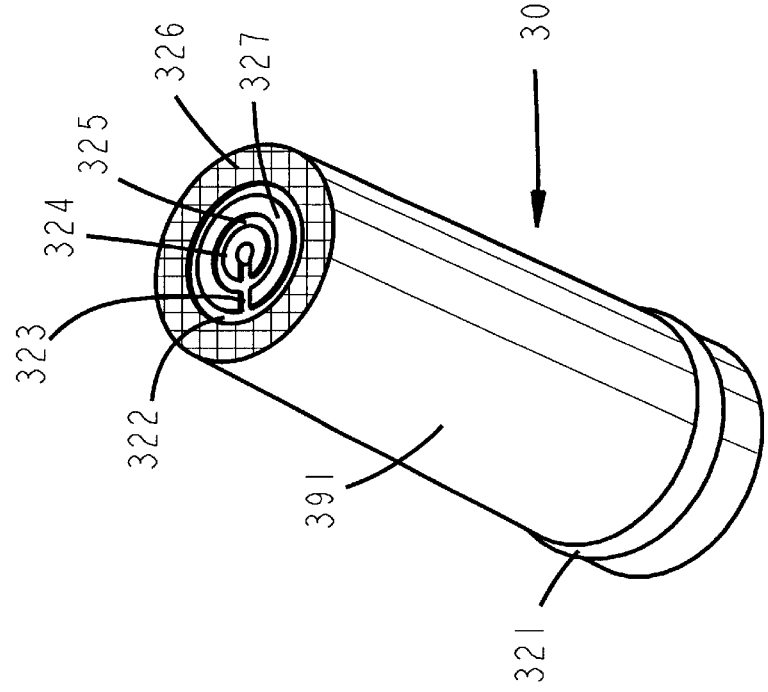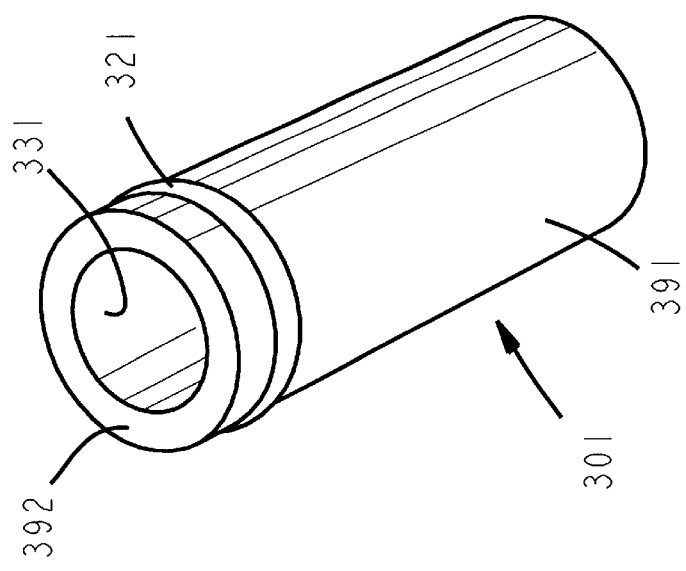

Fig. 37　SECTION B-B

APPARATUS COMPRISING A DISPOSABLE DEVICE AND REUSABLE INSTRUMENT FOR SYNTHESIZING CHEMICAL COMPOUNDS, AND FOR TESTING CHEMICAL COMPOUNDS FOR SOLUBILITY

BACKGROUND OF THE INVENTION

Field of the Invention

This invention relates to the field of solubility testing of drug compounds and other compounds, and to the field of combinatorial chemistry, and more particularly to the field of micro-solubility testing of drug compounds and other compounds, and to the field of combinatorial chemistry using multi-well reaction blocks for creating new drug compounds. This invention uses a apparatus comprising a disposable device and a reusable instrument that in the case of solubility testing can rapidly mix a solution containing a solvent and a solute, and that can separate the excess solute from the solution to enable testing the solution for solubility. The invention allows this procedure to be performed at a constant temperature. In the case of combinatorial chemistry this invention can rapidly mixes solid phase beads in a solution, and can then separate the solution from the solid phase beads. The invention allows this procedure to be performed at a constant temperature.

At present solubility testing of drug compounds is done by placing the compound (i.e. the solute) in a vial or test tube with a solvent. The vial is capped and the placed on a rocking mechanism in a constant temperature oven, that gently rocks the vial to slowly dissolve the compound into the solvent. At predetermined intervals of time samples are taken from the vial. The samples will contain a solution of solute dissolved in solvent, and some excess solute. The sample must then be filtered to remove the excess solute, so that the solubility can be measured. This method requires a minimum volume of approximately 500 $\mu$l and is labor intensive and time consuming.

At present reaction blocks used to synthesize drug compounds are expensive reusable devices, that must be cleaned after each use. The filter frits that are used to separate the drug compound from the solvent must also be replaced after each use. The presently available reusable reaction blocks must be assembled and disassembled several times to synthesize a compound.

SUMMARY OF THE INVENTION

The foregoing problems of the prior art are solved, and the objects of the present invention are achieved, by use of the disposable device and reusable instrument constructed in accordance with the principles of the present invention. In accordance with the principles of present invention, the disposable part of the invention includes one or more pairs of chambers, each chamber pair being separated by a filtration means. Each chamber pair includes a first chamber in which a solution is mixed, a filtration means for separating mixed solution from excess solute, and a second chamber that holds the solution less the excess solute. The means for mixing the solution in the first chamber is a rotating magnet. The disposable part of the invention also includes a sealing means that allows the two chambers to be pressurized, and also allows for the removal of a part or all of the solution less excess solute from the second chamber without removing the sealing means.

The reusable part of the invention includes a means to rotate one or more drive magnets; each drive magnet, through its magnetic field, causes one or more follower magnets in the disposable part of the invention to rotate at the same rotational speed as the drive magnet. The follower magnets mix the solution in the one or more first chambers of the disposable part of the invention. Also included in the reusable part of the present invention is a constant temperature water bath for controlling the temperatures of the first and second chambers of the disposable part of the invention. The reusable part of the invention also includes a means to transfer the solution less the excess solute from the first chamber, through the filtration means, to the second chamber, and from the second chamber, through the filtration means, to the first chamber.

BRIEF DESCRIPTION OF THE DRAWINGS

These and other objects, features and advantages of the invention will be evident from the following detailed description when read in conjunction with the accompanying drawings in which:

FIG. 1C is an schematic view of a magnetic circuit of the type used in this invention showing a drive magnet and two follower magnets, with the central axis of the drive magnet being oriented vertically;

FIG. 5 is an exploded bottom isometric view, having portions thereof removed, of some of the components of the embodiment of the disposable device depicted in FIG. 2;

FIG. 24 is an isometric view of a cup insert which is a component of the disposable device depicted in FIG. 21;

FIG. 25 is a bottom isometric view of the cup insert depicted in FIG. 24;

FIG. 26 is a cross-sectional view of the cup insert depicted in FIG. 24;

DETAILED DESCRIPTION OF THE PREFERRED EMBODIMENTS

Figure 1A:
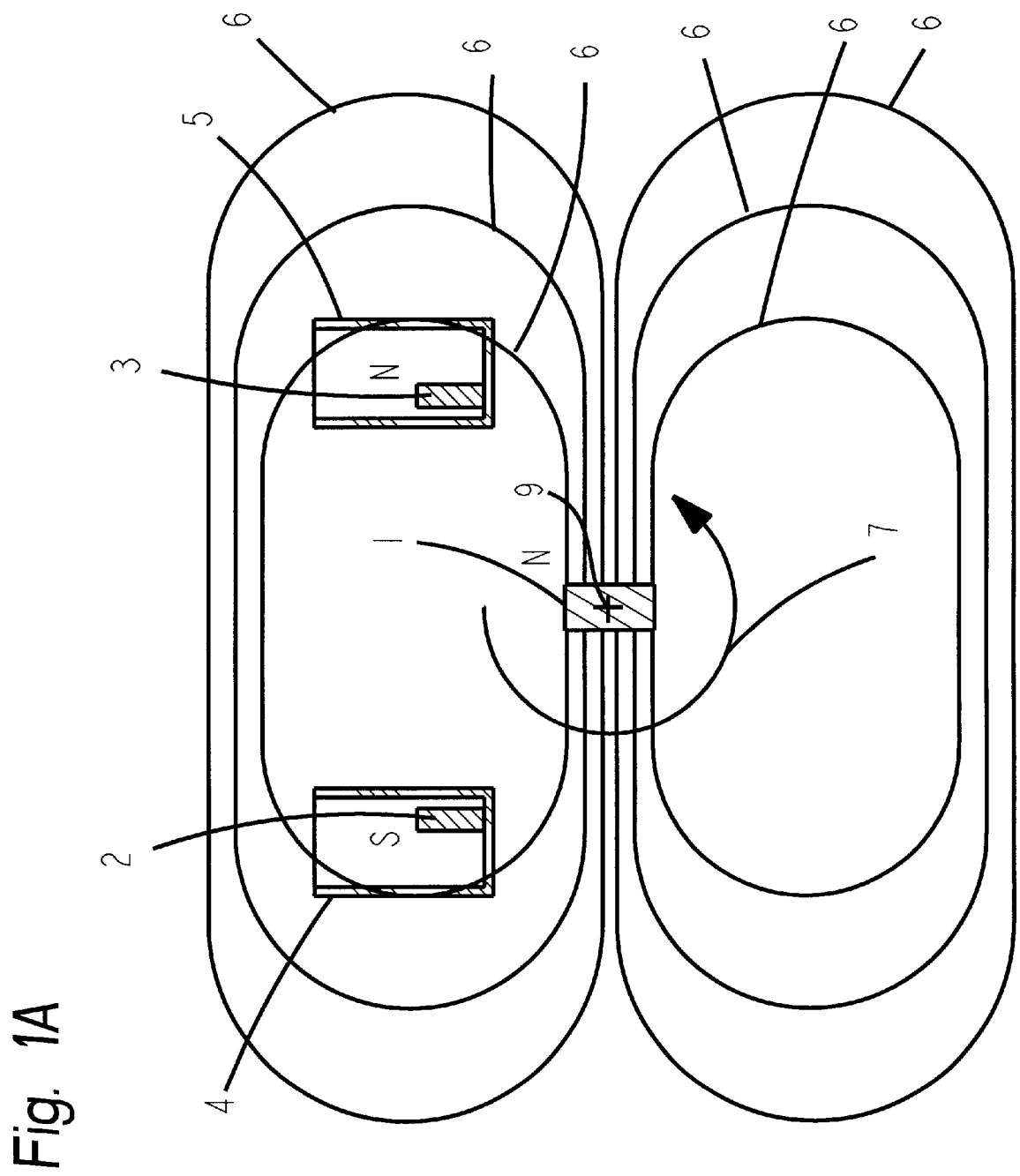
FIG. 1A is an schematic view of a magnetic circuit of the type used in this invention showing a drive magnet and two follower magnets, with the central axis of the drive magnet being oriented horizontally.

In the following description of the preferred embodiments, some of the components of an assembly are comprised of multiple parts. When this is the case, the same reference character will be used when referring to a detail of the part as well as when referring to the same detail when the detail becomes a part of the assembly.

Figure 1B:
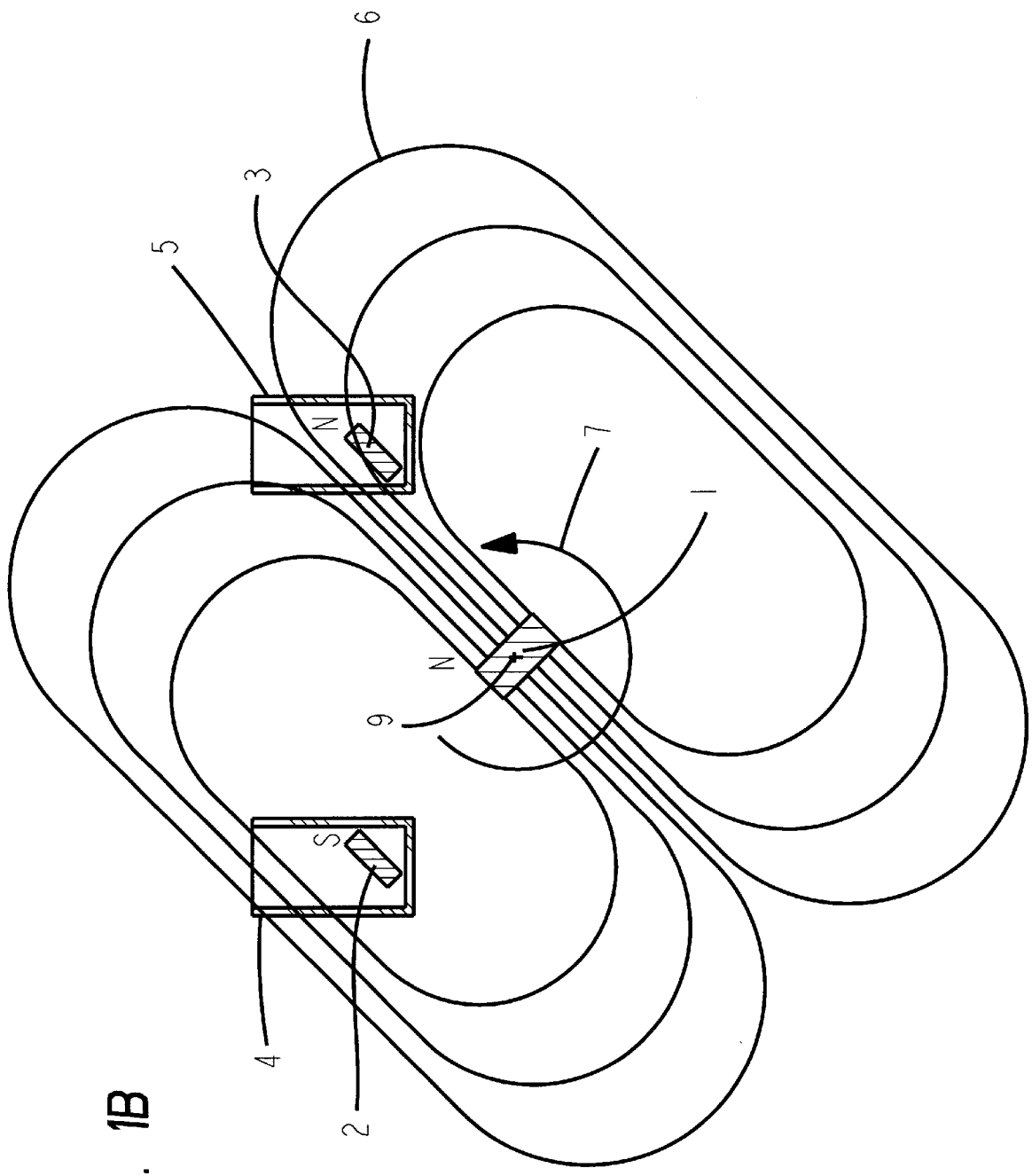
FIG. 1B is an schematic view of a magnetic circuit of the type used in this invention showing a drive magnet and two follower magnets, with the central axis of the drive magnet being oriented 45° from the horizontal.
Figure 1D:
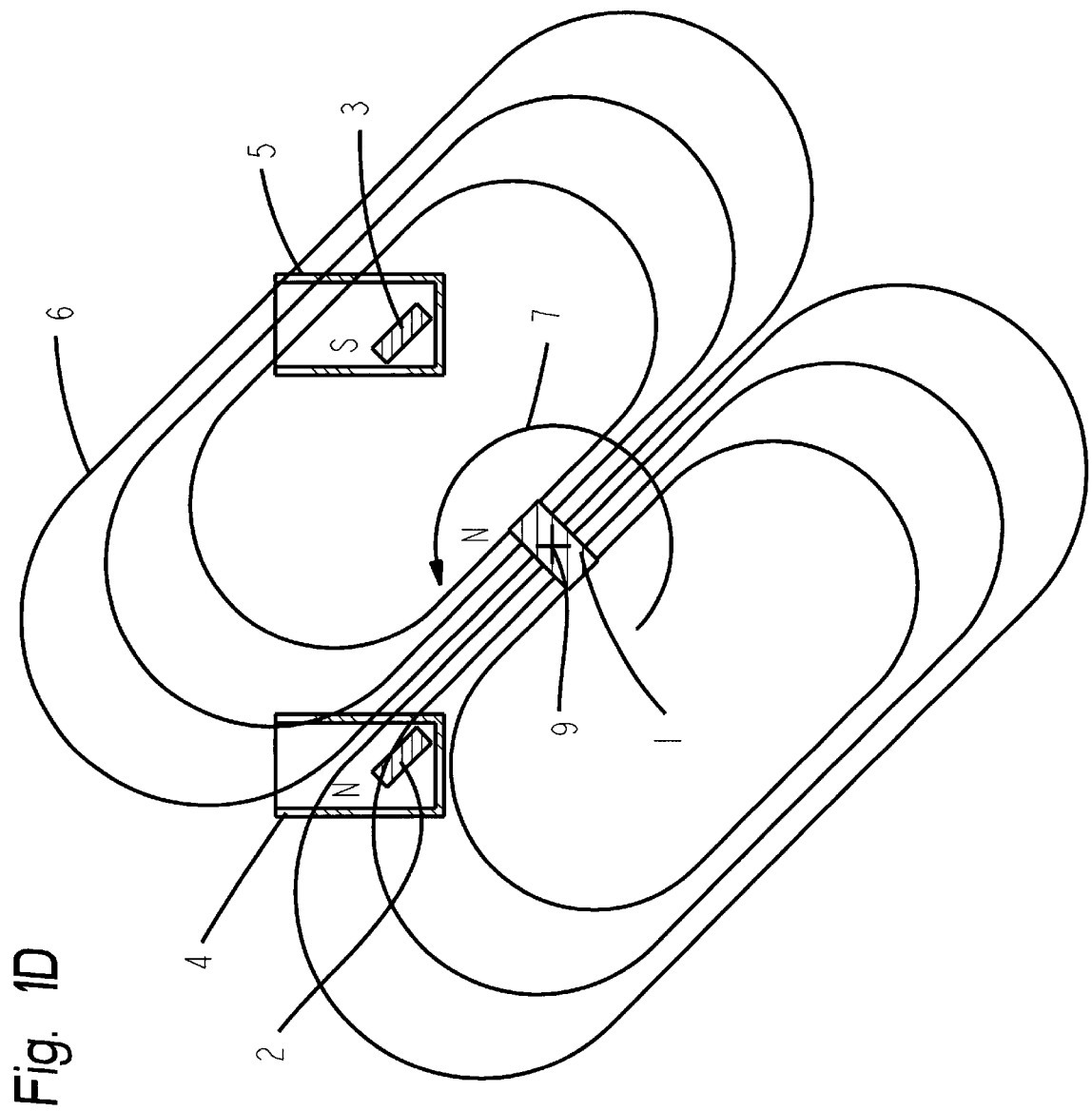
FIG. 1D is an schematic view of a magnetic circuit of the type used in this invention showing a drive magnet and two follower magnets, with the central axis of the drive magnet being oriented 135° from the horizontal.
Figure 1E:
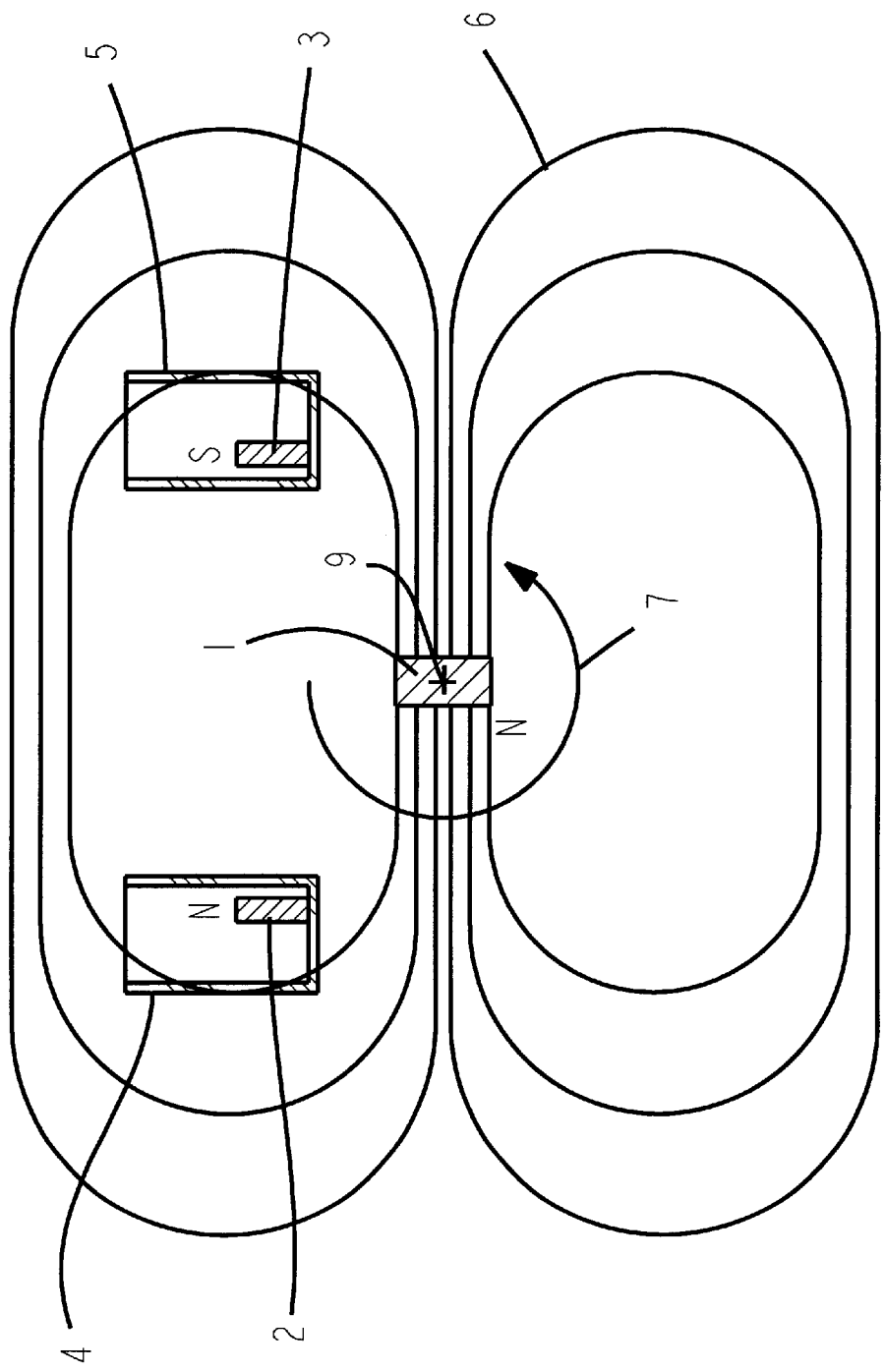
FIG. 1E is an schematic view of a magnetic circuit of the type used in this invention showing a drive magnet and two follower magnets, with the central axis of the drive magnet being oriented horizontally opposite the direction shown in FIG. 1A.

The mixing mechanism used to mix a solution in an individual well of the various embodiments of the present invention can be understood by referring to FIGS. 1A through 1E, which illustrate how follower magnets 2 and 3 respond when driver magnet 1, with its magnetic flux lines 6, rotates counterclockwise in the direction of arrow 7, about axis 9 through the center of driver magnet 1. FIG. 1A shows that when driver magnet 1 is oriented horizontally with its north pole to the right, follower magnet 3 is oriented vertically with its north pole up, and follower magnet 2 is oriented vertically with its south pole up. FIG. 1b shows that when driver magnet 1 is oriented 45° from the horizontal with its north pole up, follower magnet 3 is oriented 45° from the horizontal with its north pole up, and follower magnet 2 is oriented 45° from the horizontal with its south pole up. FIG. 1C shows that when driver magnet 1 is oriented 90° from the horizontal with its north pole up, follower magnet 3 is oriented horizontally with its north pole to the right, and follower magnet 2 is oriented horizontally with its south pole to the right. FIG. 1D shows that when driver magnet 1 is oriented 135° from the horizontal with its north pole up, follower magnet 3 is oriented 135° from the horizontal with its north pole down, and follower magnet 2 is oriented 135° from the horizontal with its north pole up. FIG. 1E shows that when driver magnet 1 is oriented horizontally with its north pole to the left, follower magnet 3 is oriented vertically with its north pole down, and follower magnet 2 is oriented vertically with its north pole up. FIGS. 1A through 1E show that as the driver magnet 1 rotates counter-clockwise the follower magnet 2 will rotate with a tumbling action in the clockwise direction in cup 4, and follower magnet 3 will rotate with a tumbling action in the clockwise direction in cup 5. For each complete revolution of driver magnet 1 in the counter-clockwise direction, the follower magnets 2 and 3 will rotate with a tumbling action one complete revolution in the clockwise direction, in their respective cups. The follower magnets should be made from a medium strength permanent magnetic material such as a sintered Alnico, or a cast Alnico, but could be made from any permanent magnetic material of sufficient strength; and the driver magnet should be made from a high strength permanent magnetic material such as Neodymium, but could be made from any permanent magnetic material with a sufficiently strong magnetic field. The follower magnets should be coated with an inert material such as Teflon.

If, instead of using two cups with a follower magnet in each cup as shown in FIGS. 1A through 1E, a single cup with one follower magnet were placed directly above the driver magnet, the follower magnet would tumble clockwise, as the driver magnet rotates counter-clockwise. Likewise a third cup with a third follower magnet could be added in line with cups 4 and 5, and directly above driver magnet 1, in FIGS. 1A through 1E. In this case all three follower magnets would tumble in the clockwise direction in their respective cups as the driver magnet rotates counter-clockwise. If the magnetic force of the driver magnet 1 is strong enough additional cups with follower magnets could be added to the right of cup 5, and to the left of cup 4 in FIGS. 1A through 1E. Also if the magnetic force of the driver magnet 1 is strong enough, additional rows of 1 or more cups with follower magnets could be added in front of driver magnet 1 (i.e. out of the page), and additional rows of 1 or more cups with follower magnets could be added behind the driver magnet 1 (i.e. behind the page), and all of the follower magnets would tumble in a clockwise direction in their respective cups as the driver magnet rotates in a counter-clockwise direction.

Figure 2:
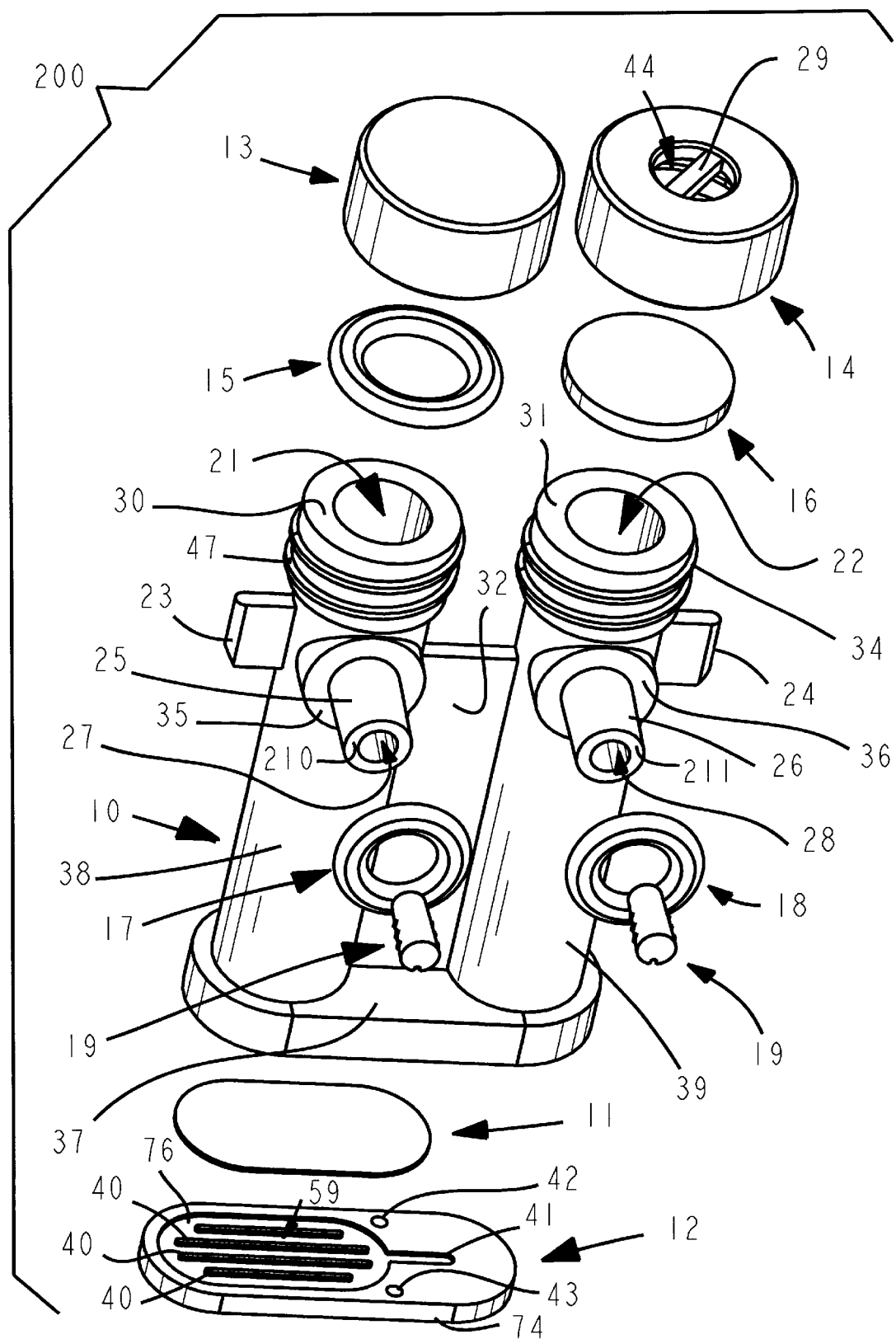
FIG. 2 is an exploded isometric view of the components of the disposable device of the first embodiment of the present invention.

Features of the disposable device 200 of the first embodiment of the present invention can be best understood by referring to FIG. 2 through FIG. 6. FIG. 2 is an exploded view showing the components that comprise the disposable device 200. The disposable device 200 contains body 10, filter element 11, bottom cover 12, mix cap o-ring 15, mix cap 13, storage septum 16, storage cap 14, gas plugs 19, mix gas o-ring 17, and storage gas o-ring 18. Body 10 is comprised of mix cylinder 38, storage cylinder 39, rib 32, and lower portion 37. Mix cylinder 38 contains mix chamber 21, defined by interior cylindrical wall 8, of mix cylinder 38, and surface 61 of lower portion 37. Storage cylinder 39 contains storage chamber 22, defined by interior cylindrical wall 57 of storage cylinder 39, and surface 65 of bottom cover 12. The bottom part of mix cylinder 38, and the bottom part of storage cylinder 39 are attached to lower portion 37. Lower portion 37 acts as a bridge between mix cylinder 38, and storage cylinder 39. Rib 32 acts as a stiffening rib to keep mix cylinder 38 and storage cylinder 39 parallel to each other, and to add strength to the disposable device 10. The bottom of lower portion 37 contains surface 69 and surface 72. The outer perimeter of surface 72 is defined by side wall 71, and the level of surface 72 relative to the level of surface 69 is defined by the height of side wall 71. Ribs 70 protrude above surface 72, and the top of ribs 70 are at the same elevation as surface 69. Lower portion 37 also contains skirt 73, which contains stepped wall 67. Guide pins 68 protrude above surface 69. The outer periphery of surface 75 of filter element 11 is sealed to surface 69 of lower portion 37, of body 10. Guide pins 68 and stepped side wall 67 position filter element 11 before filter element 11 is sealed to surface 69. Chamber 60 is defined inside of side wall 71, and in-between surface 72 of body 10, and surface 75 of filter element 11. Chamber 60 contains filter support ribs 70, which protrude above surface 72. The top surface of ribs 70 are at the same elevation as surface 69. One or more holes 55 communicate between mix chamber 21, and chamber 60. Surface 66 protrudes above surface 69 an distance equal to the thickness of filter element 11. Stepped side wall 67 of skirt 73 of body 10, contains an upper portion 142, the inner periphery of which is larger than the outer periphery of side wall 74, of bottom cover 12.

Stepped side wall 67 also contains a lower portion 141, the inner periphery of which is smaller than the outer periphery of side wall 74, of bottom cover 12. The upper portion 142 of side wall 67 locates bottom cover 12, to allow side wall 74 of bottom cover 12 to be ultrasonically shear welded to the lower portion 141 of side wall 67. The bottom cover 12 could also be bonded to body 10 using a heat bond, a glue bond, or any other type of leak tight bond. When the shear weld is complete surface 65 of bottom cover 12 will be in contact with filter element 11, and with surface 66 of body 10. Pins 68 of body 10 fit into counter bores 42 of bottom cover 12. Bottom cover 12 contains surface 76, at a level below surface 65. Chamber 59 is defined inside of side wall 63 of bottom cover 12, and in-between surface 76 of bottom cover 12, and surface 122 of filter element 11. Chamber 59 contains filter support ribs 40. The top surfaces of ribs 40 lie in the same plane as surface 65 of bottom cover 12. When bottom cover 12 is welded in place to body 10, channel 41 of bottom cover 12 places chamber 59 in communication with storage chamber 22 of storage cylinder 39.

Figure 4:
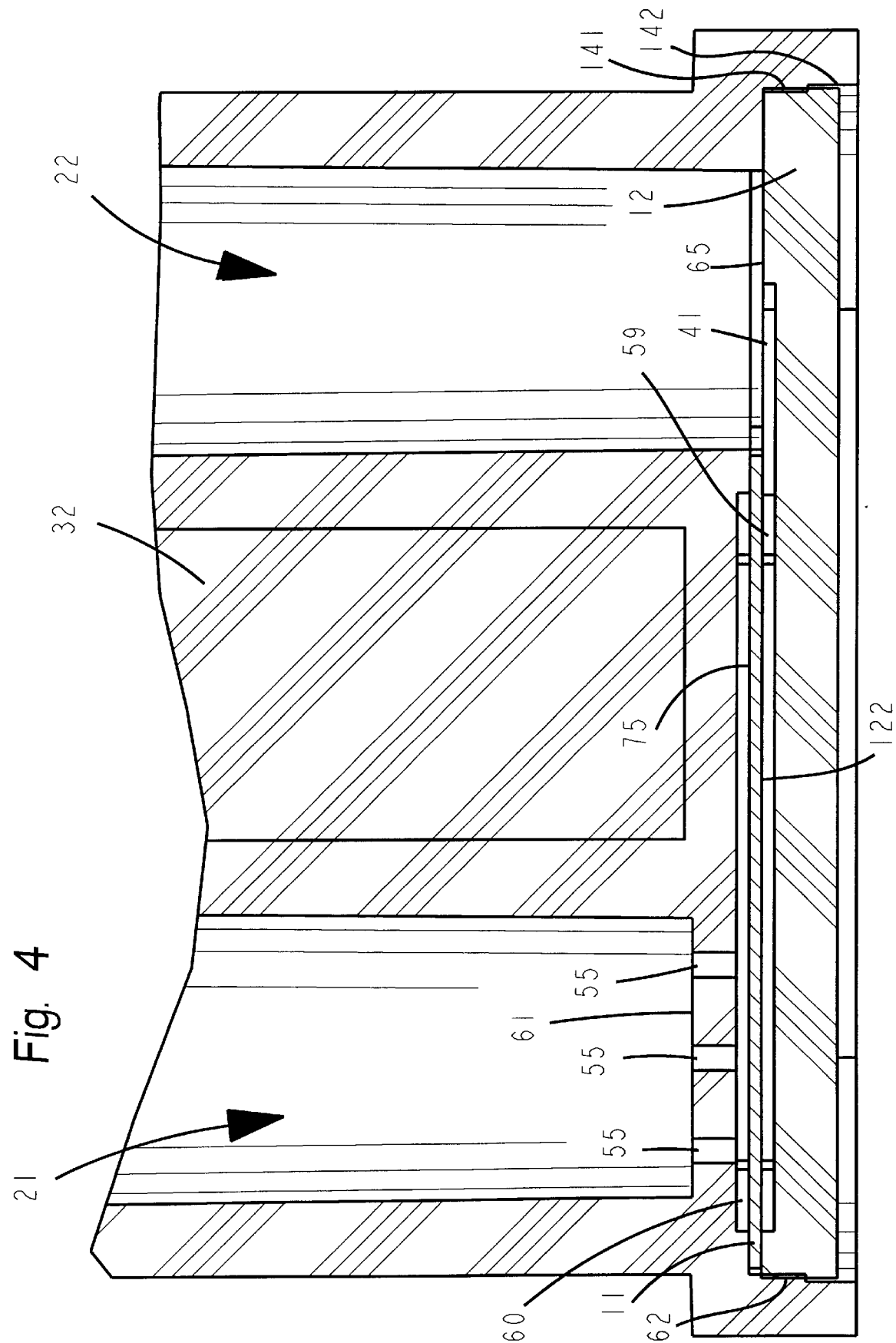
FIG. 4 is a partial sectional view of the lower portion of the embodiment of the disposable device depicted in FIG. 2.
Figure 5:
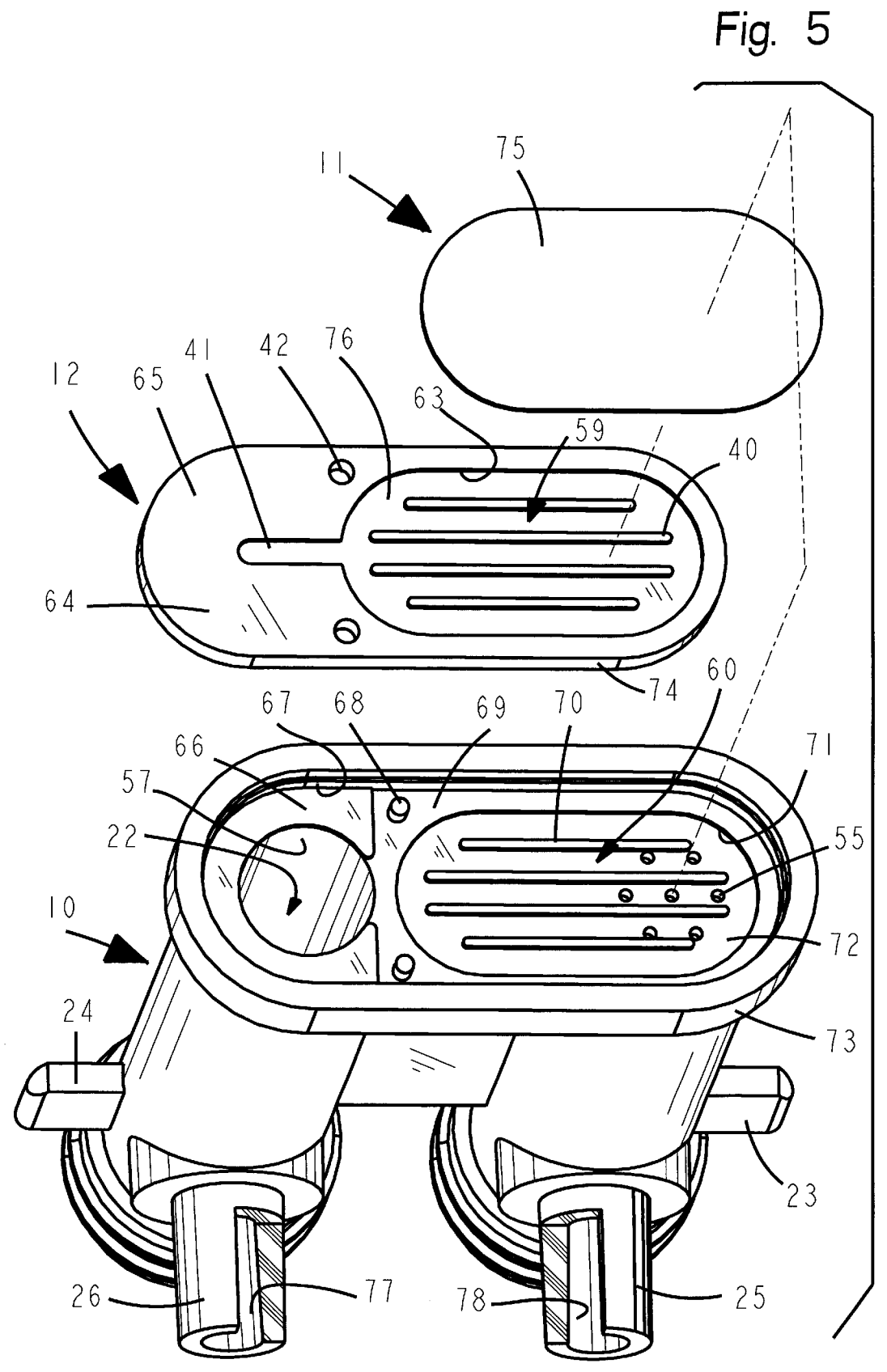

FIG. 4 and FIG. 5 show storage chamber 22 with an open bottom. The bottom of storage chamber 22 could be closed, in which case it would have to contain at least one through hole that would allow fluid flow communication and gas flow communication between storage chamber 22 and channel 41 of bottom cover 12.

Figure 3:
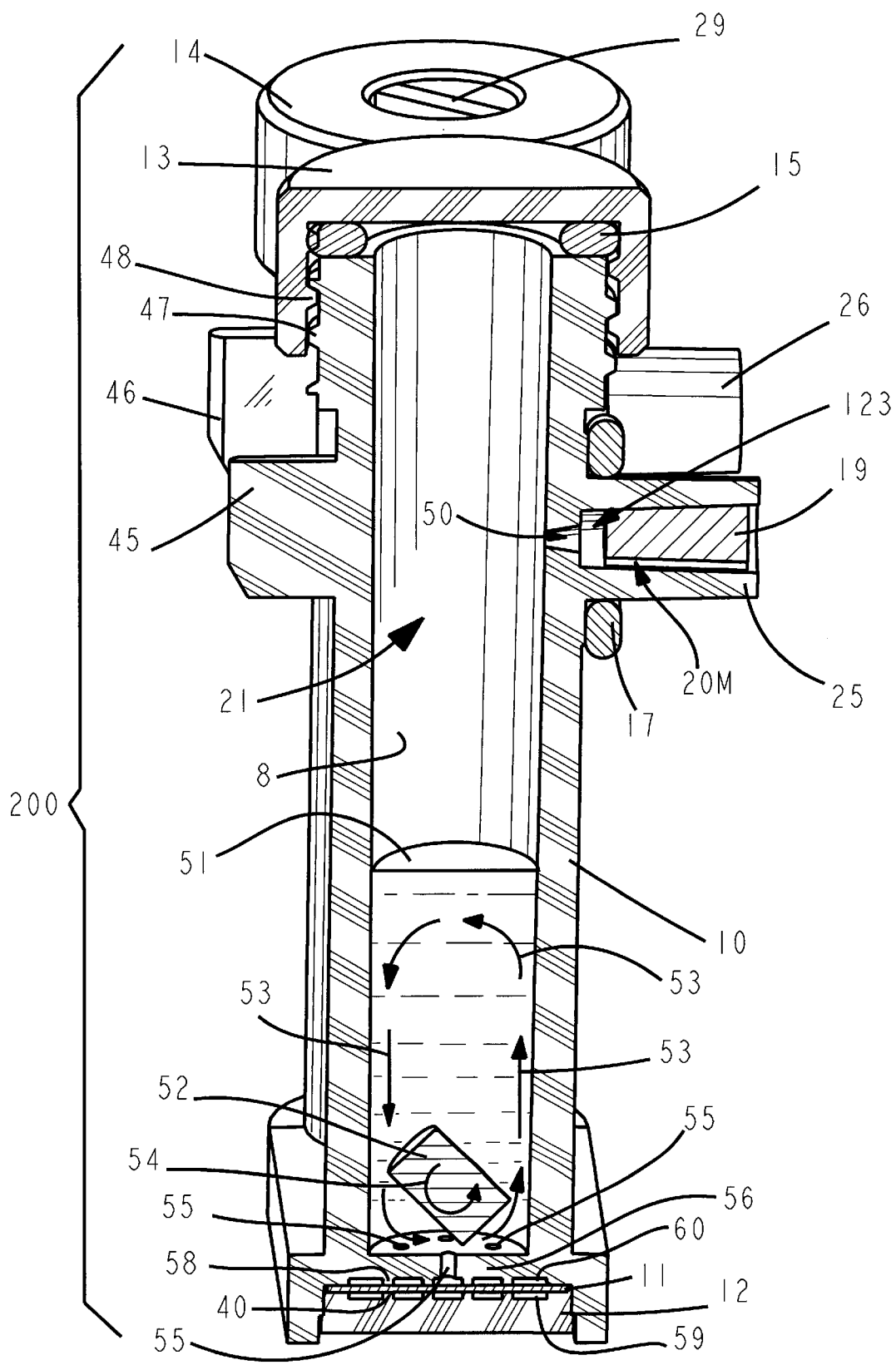
FIG. 3 is an isometric view, having portions thereof removed, of the embodiment of the disposable device depicted in FIG. 2.
Figure 6A:
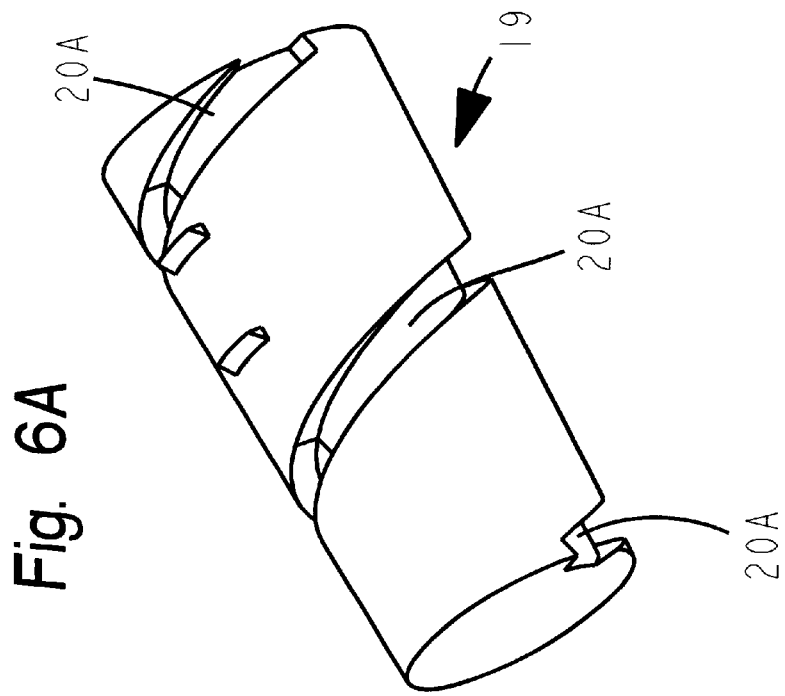
FIG. 6A is an isometric view of an alternate type of gas plug of the embodiment of the disposable device depicted in FIG. 2.
Figure 6:
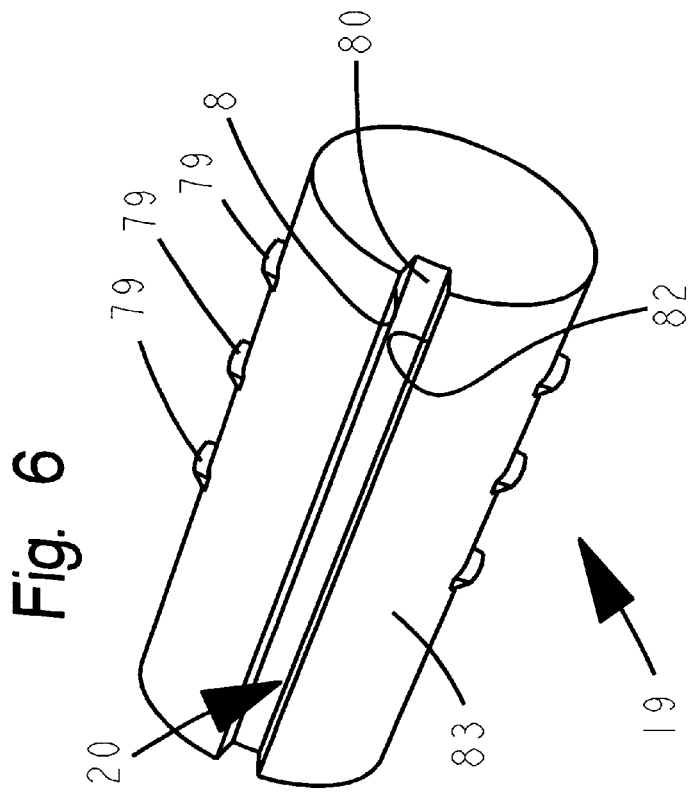
FIG. 6 is an isometric view of the gas plug of the embodiment of the disposable device depicted in FIG. 2.
Figure 19:
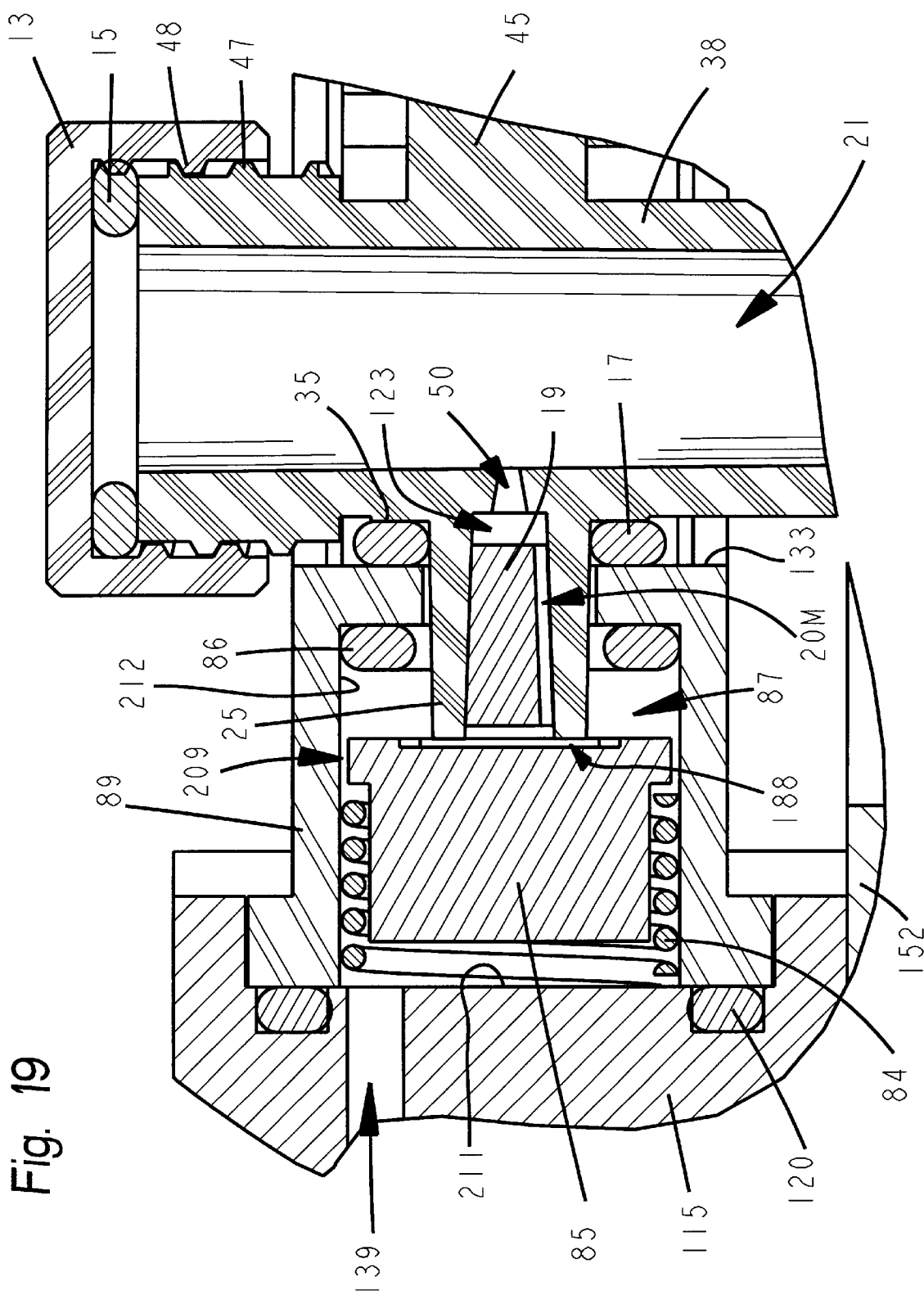
FIG. 19 is a partial cross-sectional view of a portion of the cross sectional view depicted in FIG. 18.

Referring to FIG. 2 through FIG. 6, and to ink FIG. 19, mix cylinder 38 of body 10 contains mix o-ring boss 35, and mix gas tube 25. A gas plug 19 is press fitted into the interior 27 of mix gas tube 25. Barbs 79 of gas plug 19 hold gas plug 19 in place against the interior wall 78 of mix gas tube 25. The gas plug could also be held in place using a heat bond, an ultrasonic bond, a glue bond or any other type of bond. Gas plug 19 contains channel 20, bound by surfaces 80, 81, and 82 of gas plug 19. The height and width of channel 20 should be made very small. The height of channel 20 may be as small as 0.005", and its width may be as small as 0.010". The length of channel 20 is much greater than either its height, or its width. FIG. 6A shows gas plug 19 with a spiral channel 20A. The spiral channel 20A further increases the channel length. Channel 20 could follow other serpentine paths on the outside surface of gas plug 19 so long as the channel creates a flow path from one end of gas plug 19 to its other end. Preferably interior wall 78, of mix gas tube 25 is tapered, and the outside wall 83 of gas plug 19 will have the same taper, so that when outer surface 83 of gas plug 19 is pressed into the interior of mix gas tube 25, against wall 78 of mix gas tube 25, the channel 20 of gas plug 19 will become closed channel 20M as shown in FIG. 3, and FIG. 19. Chamber 123 is also created when gas plug 19 is pressed into the interior 27 of mix gas tube 25. Again referring to FIG. 3, and FIG. 19, there is a flow path from mix chamber 21 through port 50, into chamber 123, through channel 20M, to the exterior of mix chamber 21. The purpose of this flow path will become apparent later.

Referring to FIG. 2, FIG. 3, and to FIG. 19, mix cylinder 38 of body 10 contains external threads 47 at the top of mix cylinder 38. Mix cap 13 contains internal threads 48. Mix cap o-ring 15 fits into mix cap 13, so that when mix cap 13 is screwed onto mix cylinder 38, thus engaging threads 47 of mix cylinder 38, to threads 48 of mix cap 13, o-ring 15 is compressed between mix cap 13, and the top surface 30 of mix cylinder 38, thus sealing the open top of mix cylinder 38 closed.

Figure 20:
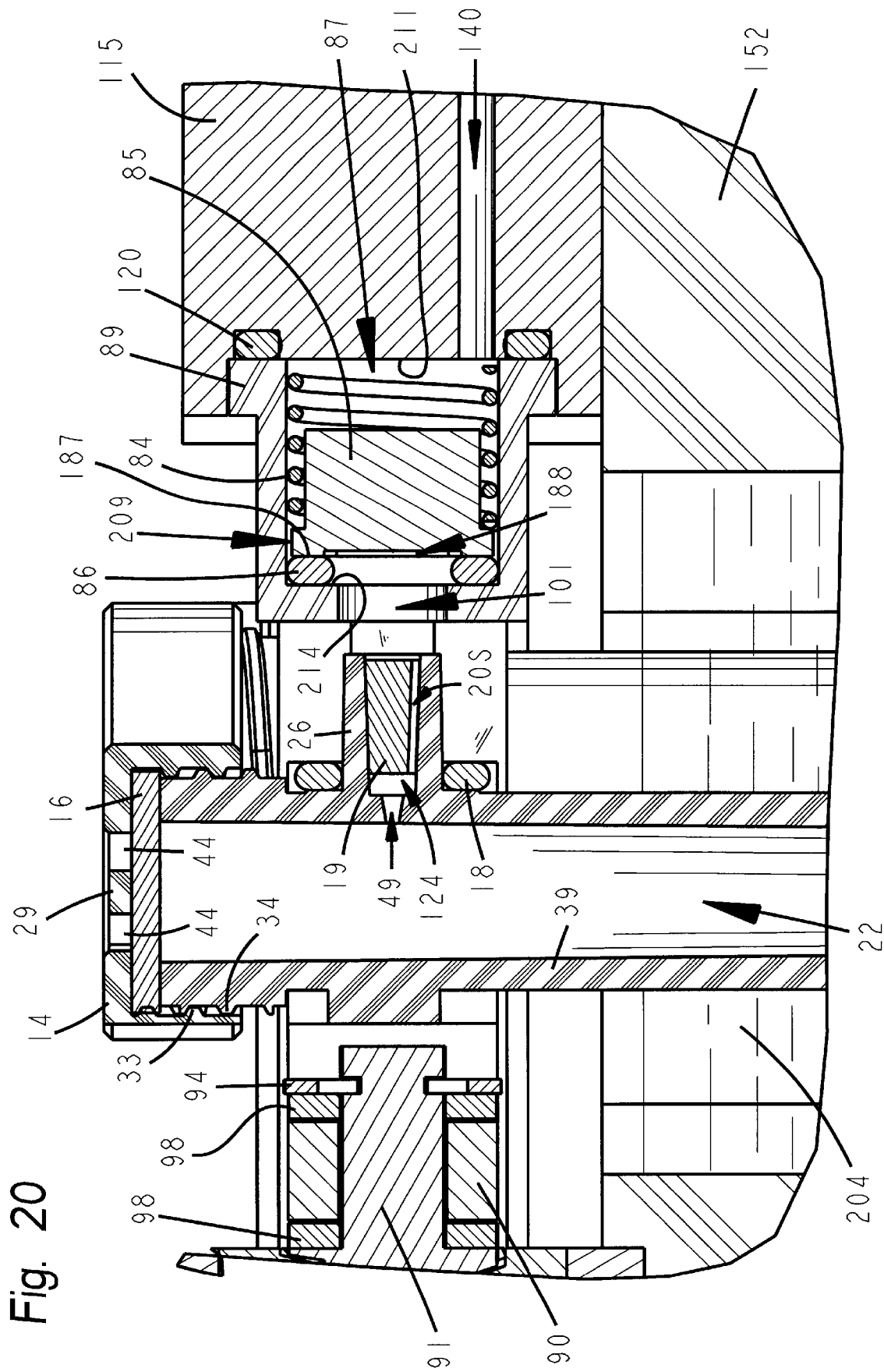
FIG. 20 is a partial cross-sectional view of a portion of the cross sectional view depicted in FIG. 18.

Referring to FIG. 2 through FIG. 6, and to FIG. 20, storage cylinder 39 of body 10 contains storage o-ring boss 36, and storage gas tube 26. A gas plug 19 is press fitted into the interior 28 of storage gas tube 26. Barbs 79 of gas plug 19 hold gas plug 19 in place against the interior wall 77 of storage gas tube 26. The gas plug could also be held in place using a heat bond, an ultrasonic bond, a glue bond or any other type of bond. Gas plug 19 contains channel 20, bound by surfaces 80, 81, and 82 of. The height and width of channel 20 should be made very small. The height of channel 20 may be as small as 0.005", and its width may be as small as 0.010". The length of channel 20 is much greater than either its height, or its width. Preferably interior wall 77, of storage gas tube 26 is tapered, and the outside wall 83 of gas plug 19 will have the same taper, so that when outer surface 83 of gas plug 19 is pressed into the interior of storage gas tube 26, against wall 77 of storage gas tube 26, the channel 20 of gas plug 19 will become closed channel 20S as shown in FIG. 20. Chamber 124 is also created when gas plug 19 is pressed into the interior 28 of storage gas tube 26. Again referring to FIG. 20, there is a flow path from storage chamber 22 through port 49, into chamber 124, through channel 20S, to the exterior of storage chamber 22. The purpose of this flow path will become apparent later.

Referring to FIGS. 2 and FIG. 20, storage cylinder 39 of body 10 contains external threads 34 at the top of storage cylinder 39. Storage cap 14 contains internal threads 33. Storage cap septum 16 fits into storage cap 14, so that when storage cap 14 is screwed onto storage cylinder 39, thus engaging threads 34 of storage cylinder 39, to threads 33 of storage cap 14, storage cap septum 16 is compressed between storage cap 14, and the top surface 31 of storage cylinder 39, thus sealing the open top of storage cylinder 39 closed. Openings 44 of storage cap 14 provide a means to insert a needle through storage cap septum 16, into storage chamber 22 of storage cylinder 39, to remove solution from storage chamber 22. The storage cap septum 16 should be made from a material that is self sealing, so that when the needle is removed the septum will continue to seal the open top of storage cylinder 39 closed. Septum support rib 29 of storage cap 14 provides additional support for storage cap septum 16.

Referring to FIG. 2 and FIG. 3, body 10 contains alignment tabs 23 and 45 attached to mix cylinder 38, and alignment tabs 24 and 46 attached to storage cylinder 39. The purpose of the alignment tabs will become evident later.

Figure 7:
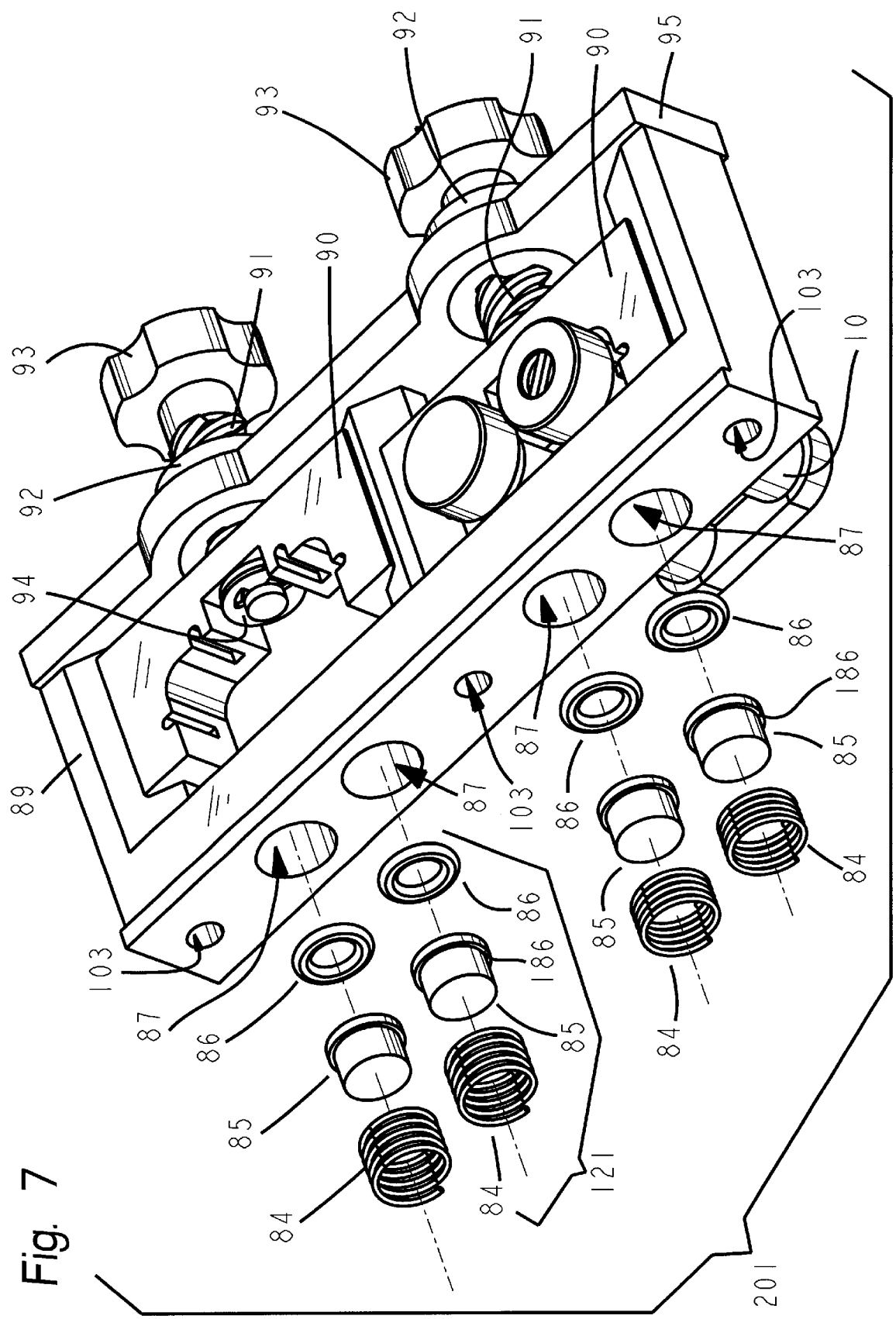
FIG. 7 is a partial exploded view of the nest sub-assembly which is a component of the reusable instrument of the first embodiment of the present invention.
Figure 8:
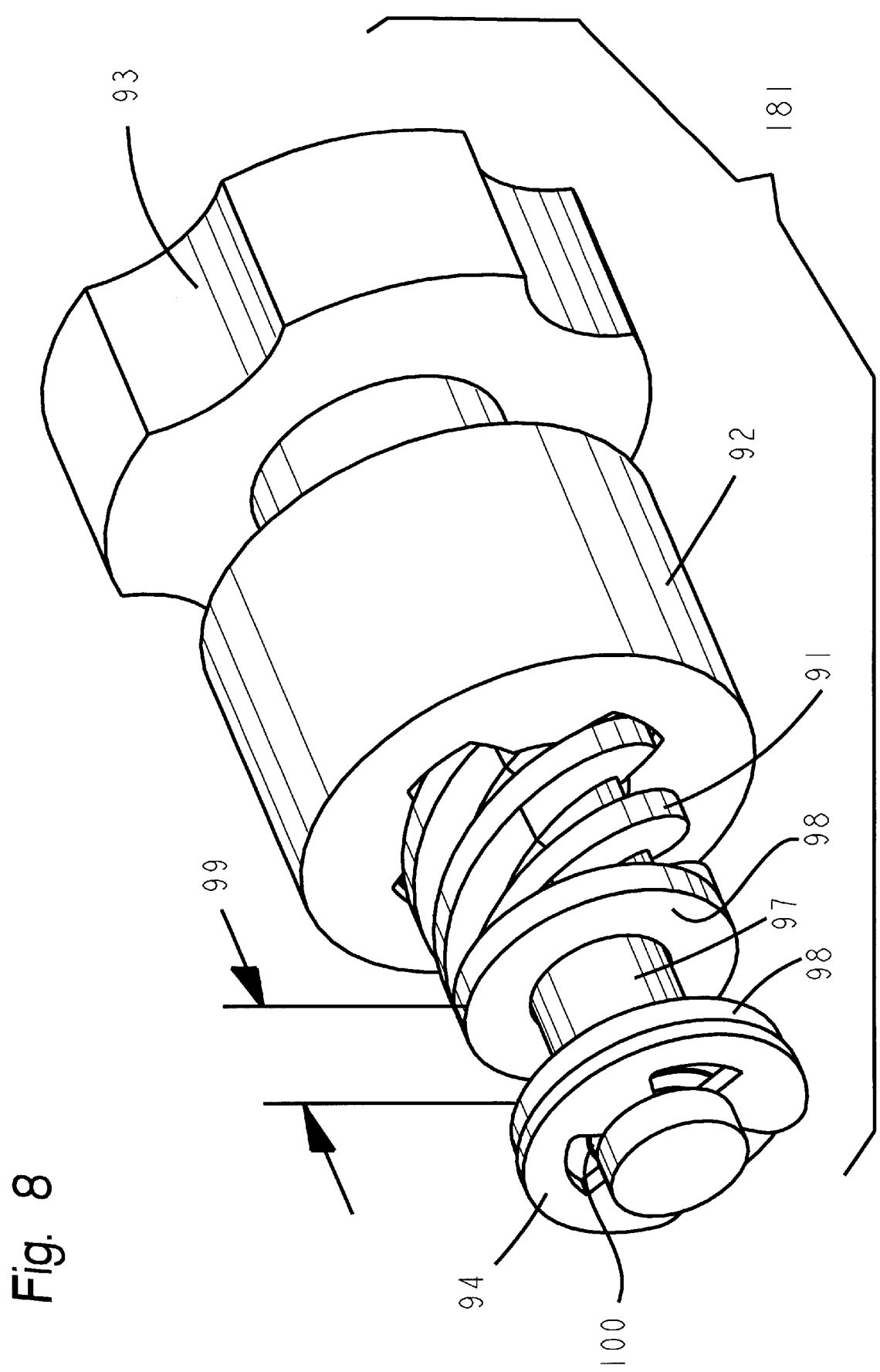
FIG. 8 is an isometric view of the screw sub assembly which is a component of the nest subassembly depicted in FIG. 7.
Figure 9:
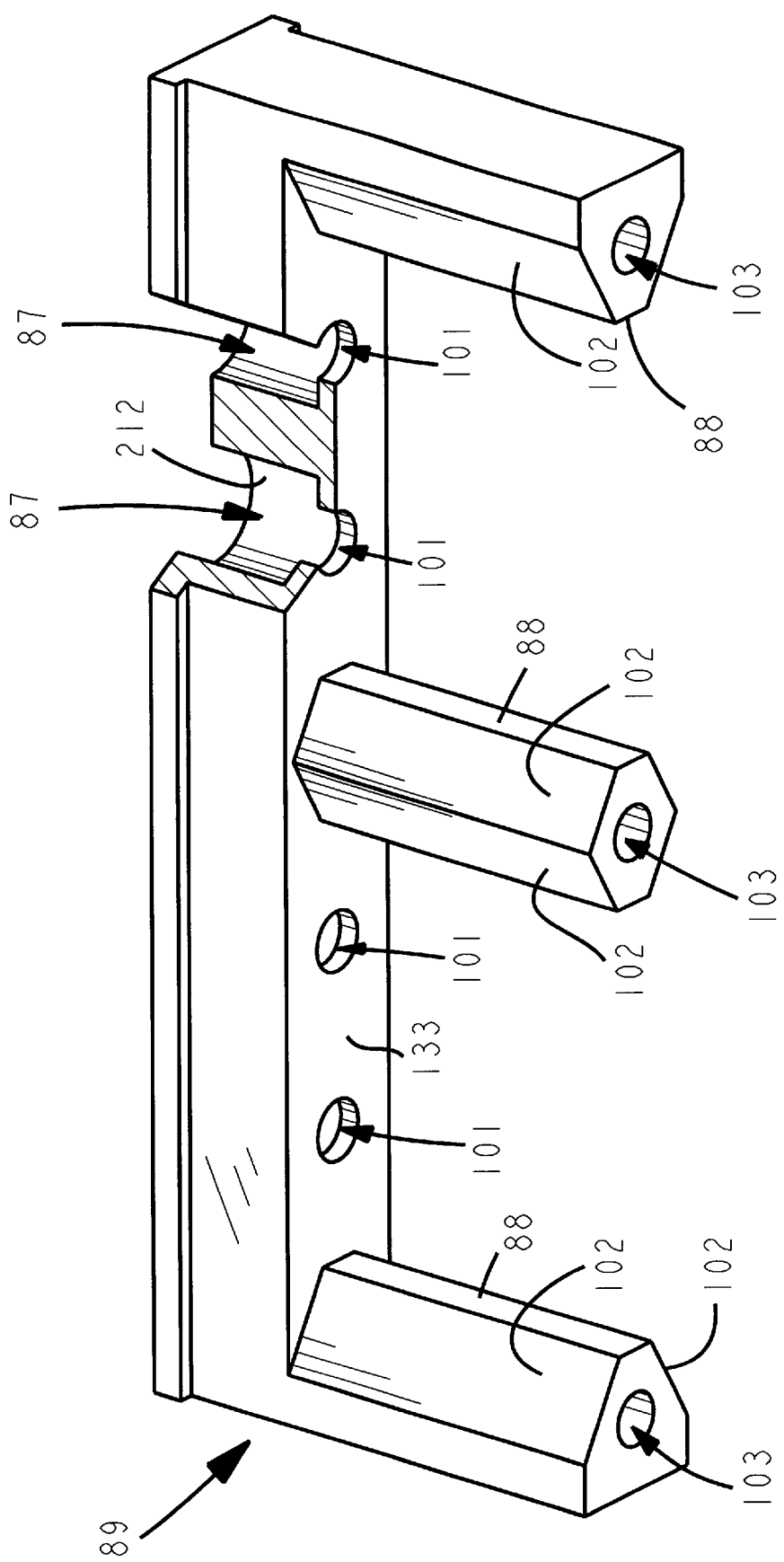
FIG. 9 is an isometric view with portions thereof removed of the nest guide which is a component of the nest sub-assembly depicted in FIG. 7.
Figure 10:
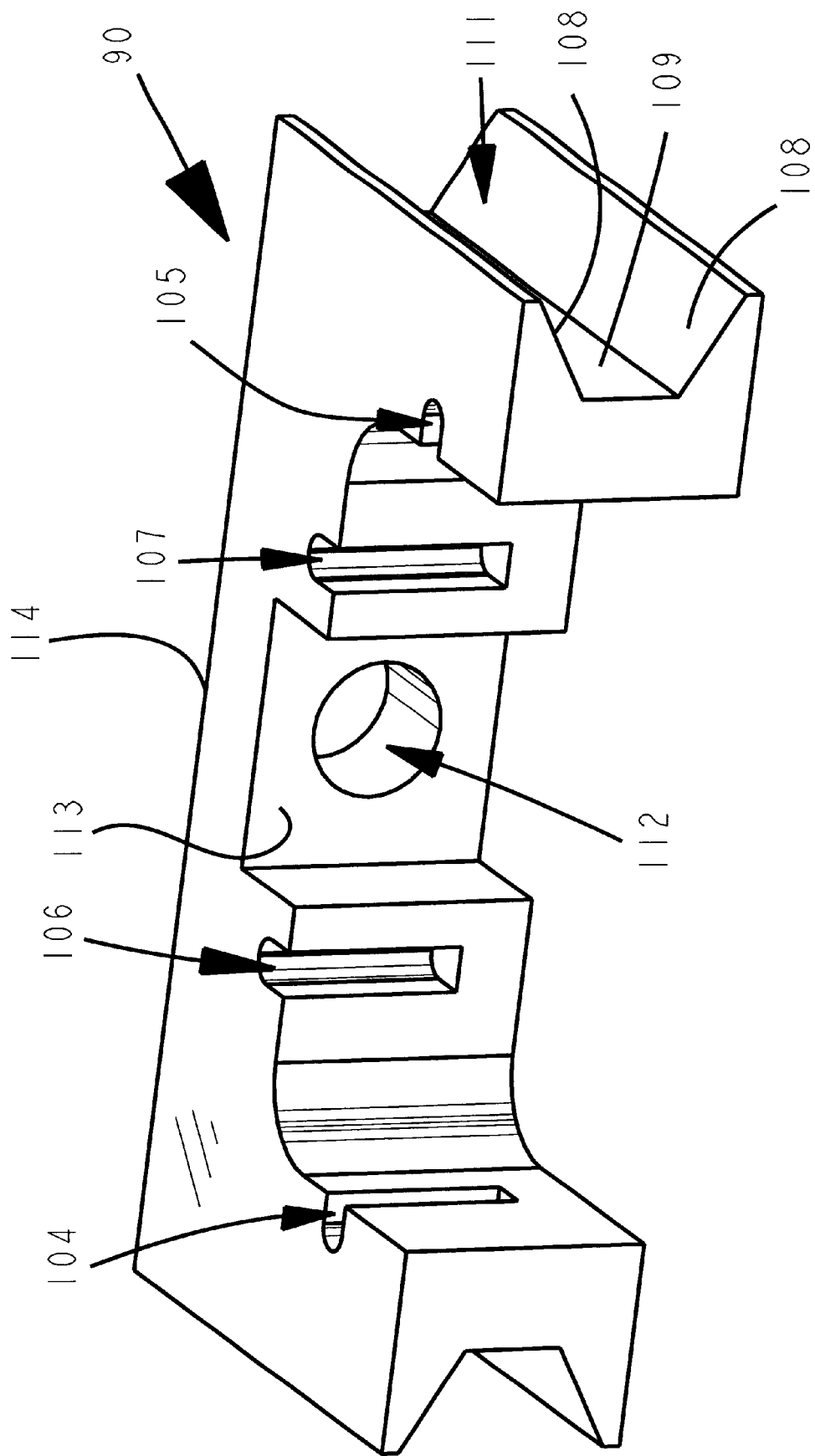
FIG. 10 is an isometric view of the nest which is a component of the nest sub-assembly depicted in FIG. 7.

The nest assembly 201 of the first embodiment of the present invention can be best understood by referring to FIGS. 7 through 10. FIG. 7 is a partially exploded view of a nest assembly 201 containing 2 nests 90. A nest assembly 201 could contain one or more nests 90. The two place nest assembly 201 shown in FIG. 7, is comprised of a nest guide 89, a nest back plate 95, two nests 90, two screw assemblies 181, and a pair of check valve assemblies 121 for each nest. The nest guide 89 contains two truncated v-ways per nest, comprised of nest guide surfaces 88 and 102; two check valve counterbores 87 for each nest; two ports 101 for each nest; and mounting holes 103. Each nest 90 contains a pair of truncated v-grooves 111, comprised of surfaces 108, and 109; four tab slots 104, 105, 106, and 107; and a screw hole 112. Each screw assembly 181 contains, a screw knob 93, attached to the screw 91; a nut 92 containing a internal thread that matches the screw thread, two washers 98, a snap ring 94, a screw shaft extension 97, and a snap ring groove 100. The screw 91 preferably contains a quadruple thread, but could contain any kind of thread.

Figure 15:
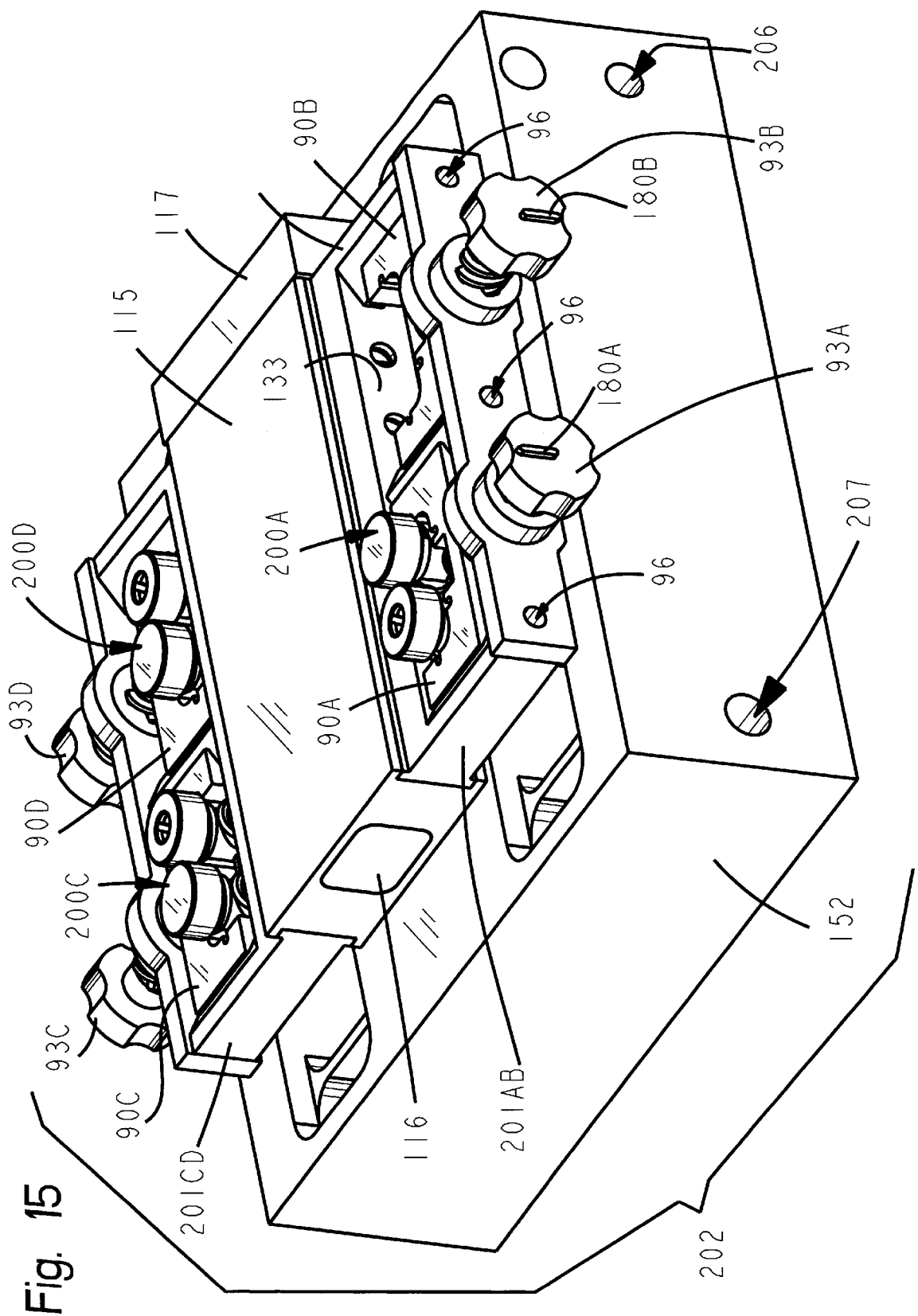
FIG. 15 is an isometric view of the complete apparatus of the first embodiment of the present invention, including the reusable instrument, with two disposable devices in the engaged position, and one disposable device in the disengaged position.

Referring to FIG. 7 through FIG. 10, FIG. 15, and FIGS. 18 through 20, nut 92 of screw—assembly 181 is attached to nest back plate 95, using a press fit, or any other suitable form of attachment. Nest back plate 95 attaches to nest guide 89 with bolts (not shown), that fit through clamp holes 96 of nest back plate 95, and through mounting holes 103 of nest guide 89. As will be shown later the same clamp bolts attach the nest assembly 201 to the manifold 115. The truncated v-grooves 111 of nest 90, slides on the truncated v-ways of nest guide 89. The screw is attached to nest 90 by inserting screw shaft extension 97 of screw 91, through screw hole 112 of nest 90, with a washer 98 on either side of screw hole 112. Snap ring 94 snaps into snap ring groove 100 of screw shaft extension 97, thus attaching nest 90 to screw 91. If screw 91 contains a right hand thread, then the nest 90 will slide in on the truncated v-ways of nest guide 89, away from nest back plate 95, when the screw knob 93 is rotated clockwise. When screw 91 contains a multiple thread such as a quadruple thread, then the nest 90 will travel from its out position to its in position when screw knob 93 is rotated 180°, as shown in FIG. 15.

Referring to FIG. 2, FIG. 3, FIG. 7, and FIG. 10, alignment tabs 23, 24, 45, and 46 of body 10, fit into tab slots 104, 105, 106, and 107 respectively of nest 90, to locate body 10 of disposable device 200 on nest 90.

Referring to FIG. 7, each check valve counterbore 87 of nest guide 89 contains a check valve assembly 121 comprised of an o-ring 86, a check plug 85, and a check spring 84.

Figure 11:
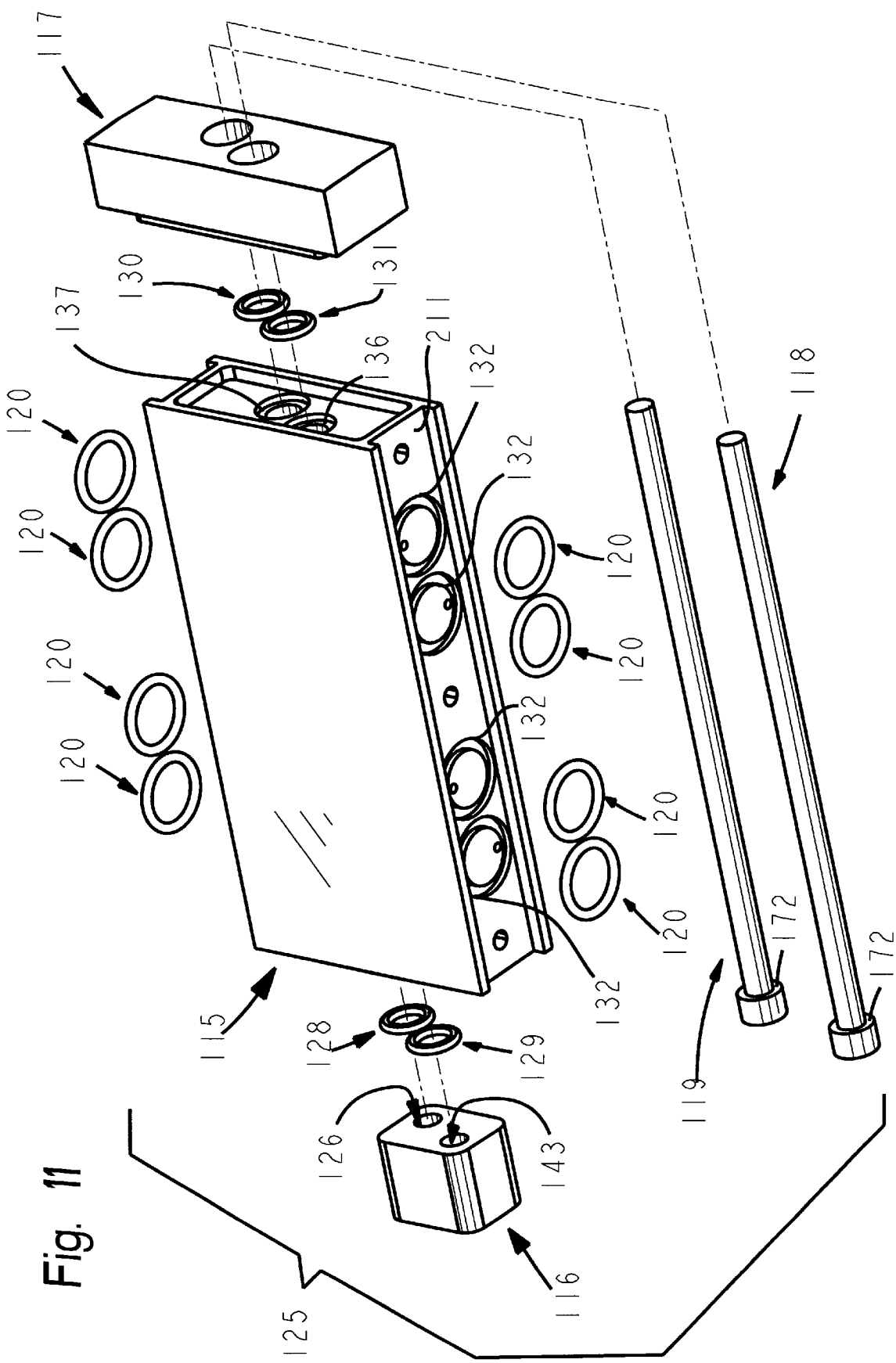
FIG. 11 is an exploded view of the gas manifold sub-assembly of the reusable instrument of the first embodiment of the present invention.
Figure 12:
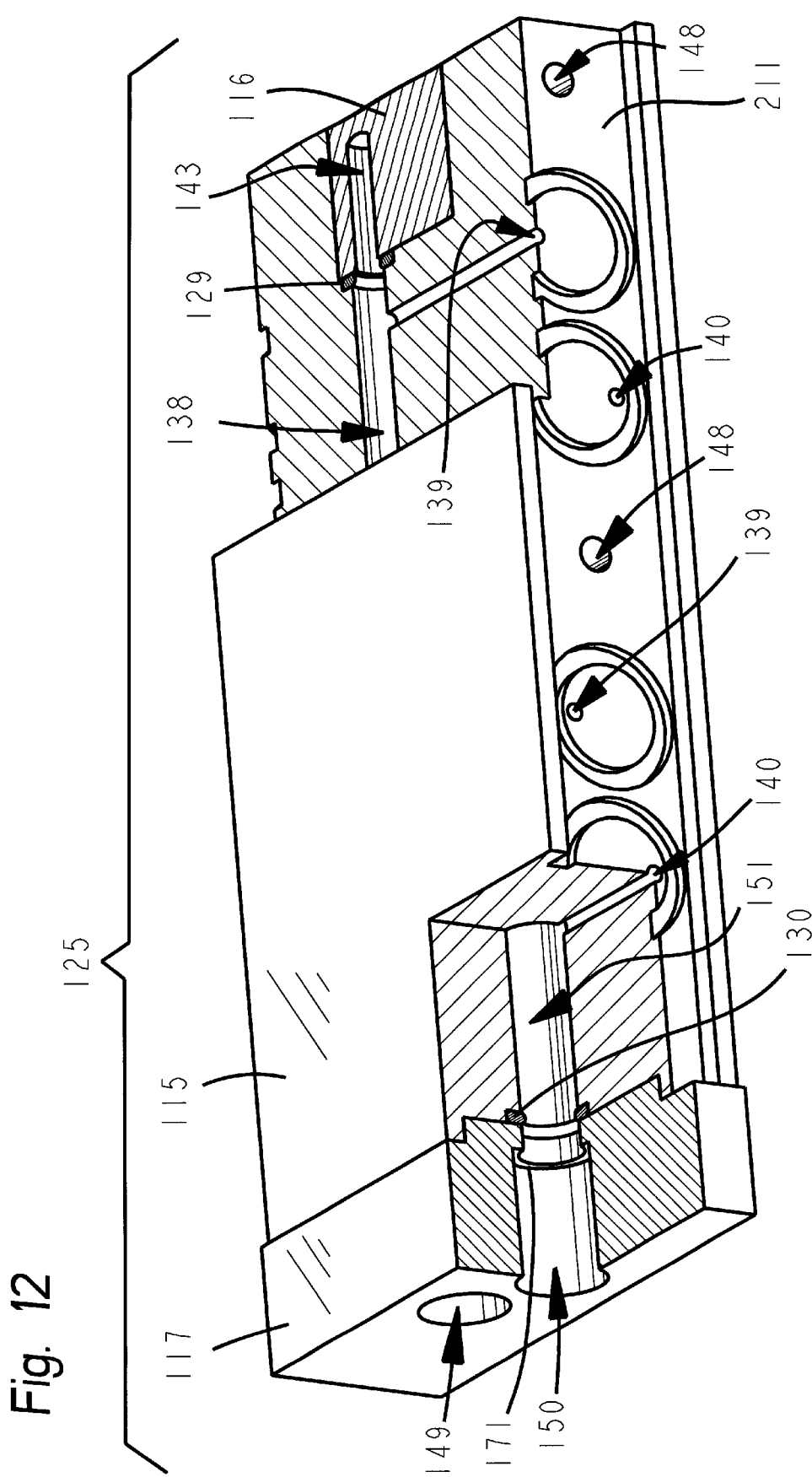
FIG. 12 is an isometric view with portions thereof removed of the manifold sub-assembly depicted in FIG. 11.

FIGS. 11 and FIG. 12, illustrate manifold assembly 125 which is a part of the first embodiment of the present invention. FIG. 11 is an exploded view of the components that comprise the manifold assembly 125. Manifold assembly 125 includes manifold 115, end nut 116, manifold end cap 117, clamp bolts 118, and 119, end nut o-rings 128 and 129, end cap o-rings 130 and 131, and manifold o-rings 120. FIG. 12 shows the manifold assembly 125 in the assembled state, less clamp bolts 118 and 119, and less manifold o-rings 120. Referring to FIG. 7, FIG. 11, FIG. 12, and FIG. 15, a manifold assembly 125 will have one nest assembly 201 attached to either side of manifold 115. Manifold 115 contains through holes 138 and 151. Side ports 139 from both sides of manifold 115 connect to through hole 138 of manifold 115. Side ports 140 from both sides of manifold 115 connect to through hole 151 of manifold 115. Both sides of manifold 115 contain pairs of ports 140 and 139, the number of pairs, equals the number of nests in a nest assembly 201. Referring to FIG. 7, FIG. 9, FIG. 11, FIG. 12, and FIG. 15, clamp bolts (not shown), that go through clamp holes 96 of nest back plate 95, and through mounting holes 103 of nest guide 89, screw into clamp holes 148 of manifold 115, thus attaching nest assembly 201 to manifold 115. When the nest assembly 201 is attached to manifold 115 the ports 139 and 140 of manifold 115 will lie within the circle that defines the edge of cylindrical surface 212 of the corresponding check valve counterbore 87 of nest guide 89, and o-rings 120 of manifold assembly 125 will seal and isolate each check valve counterbore 87 of nest guide 89 to its corresponding port (either a port 140 or a port 139) on manifold 115. The components of manifold assembly 125 are held together by clamp bolt 118 and clamp bolt 119. The head of clamp bolt 119 fits into storage counterbore hole 150 of manifold end cap 117, with face 172 of clamp bolt 119 mating against surface 171 of storage counterbore hole 150. Either surface 172 of clamp bolt 119, or surface 171 of storage counterbore hole 150 should be grooved, or a grooved washer (not shown) should be placed between surface 172 of clamp bolt 119 and surface 171 of storage counterbore hole 150, to allow a passage for gas to flow between surface 172 of clamp bolt 119 and surface 171 of storage counterbore hole 150. The shank of clamp bolt 119 fits loosely into through hole 151 of manifold 115, and the threaded portion of clamp bolt 119 (not shown screws into threaded hole 126 (threads not shown) of end nut 116. O-ring 128 seals threaded hole 126 of end nut 116 to one end of through hole 151 of manifold 115, and o-ring 130 seals the other end of through hole 151 to storage counterbore hole 150 of manifold end cap 117. In a like manner the head of clamp bolt 118 fits into mix counterbore hole 149 of manifold end cap 117, the shank of clamp bolt 118 fits loosely into through hole 138 of manifold 115, the threaded portion of clamp bolt 118 screws into threaded hole 143 of end nut 116, o-ring 129 seals one end of through hole 138 of manifold 115 to threaded hole 143 of end nut 116, and o-ring 131 seals the other end of through hole 138 of manifold 115 to mix counterbore hole 149 of manifold end cap 117. Hence, all of the ports 140 on either side of manifold 115 connect to storage counterbore hole 150, of manifold end cap 117, through hole 151 of manifold 115, and all of the ports 139 on either side of manifold 115 connect to mix counterbore hole 149 of manifold end cap 117 through hole 138 of manifold 115. Alternately the ends of through holes 138 and 150 that mate to threaded holes 126 and 143 of end nut 116 could be dead ended, thus eliminating end nut 116, o-ring 128, and o-ring 129; manifold end cap 117 and clamp bolts 118 and 119 could also be eliminated by adding mix counterbore hole 149 and storage counterbore hole 150 to manifold 115. However by using the manifold with end cap and end nut, with longer clamp bolts, multiple manifolds could be assembled as modules to create a longer manifold.

Figure 13:
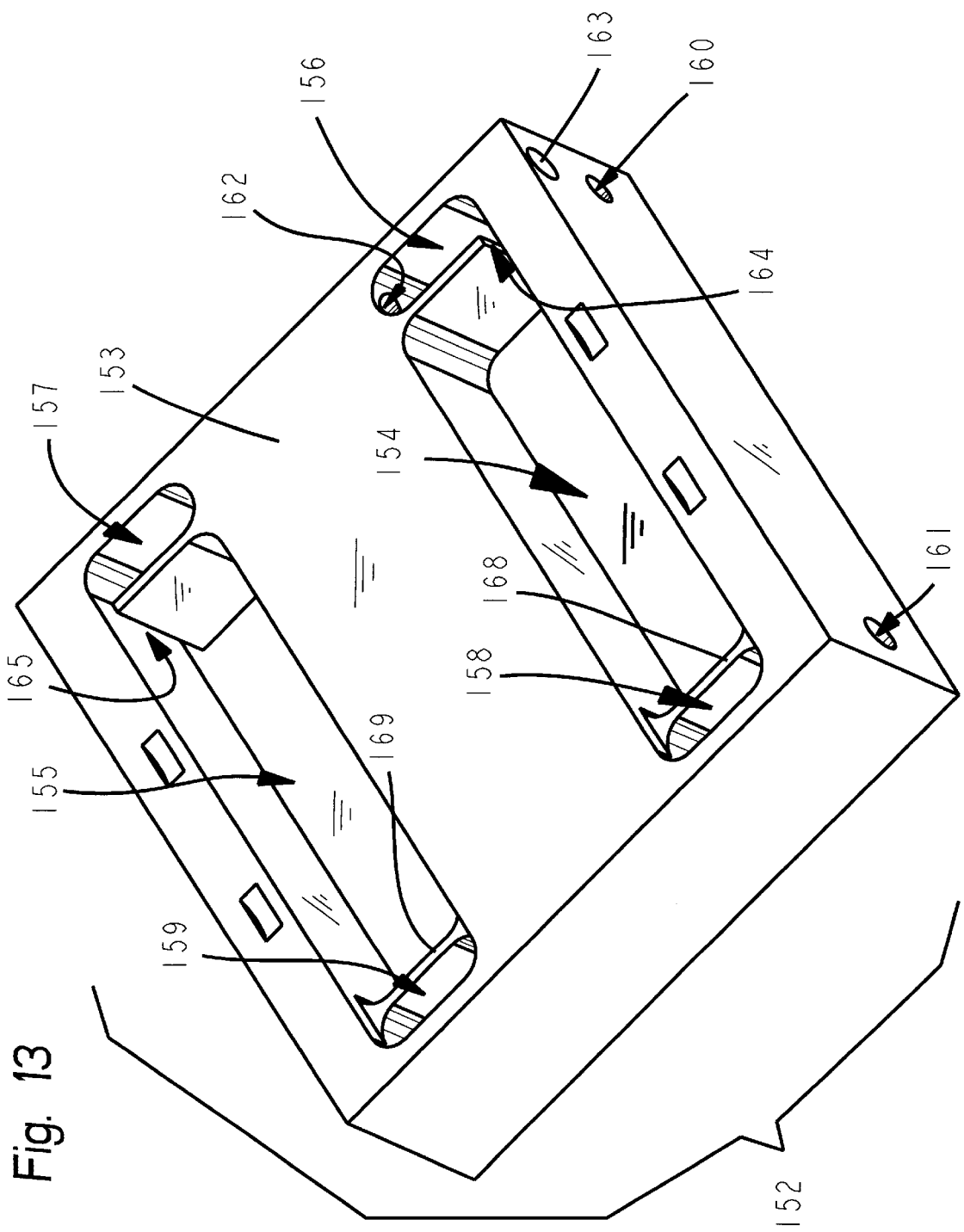
FIG. 13 is an isometric view of the water bath sub-assembly which is a component of the reusable instrument of the first embodiment of the present invention.
Figure 14:
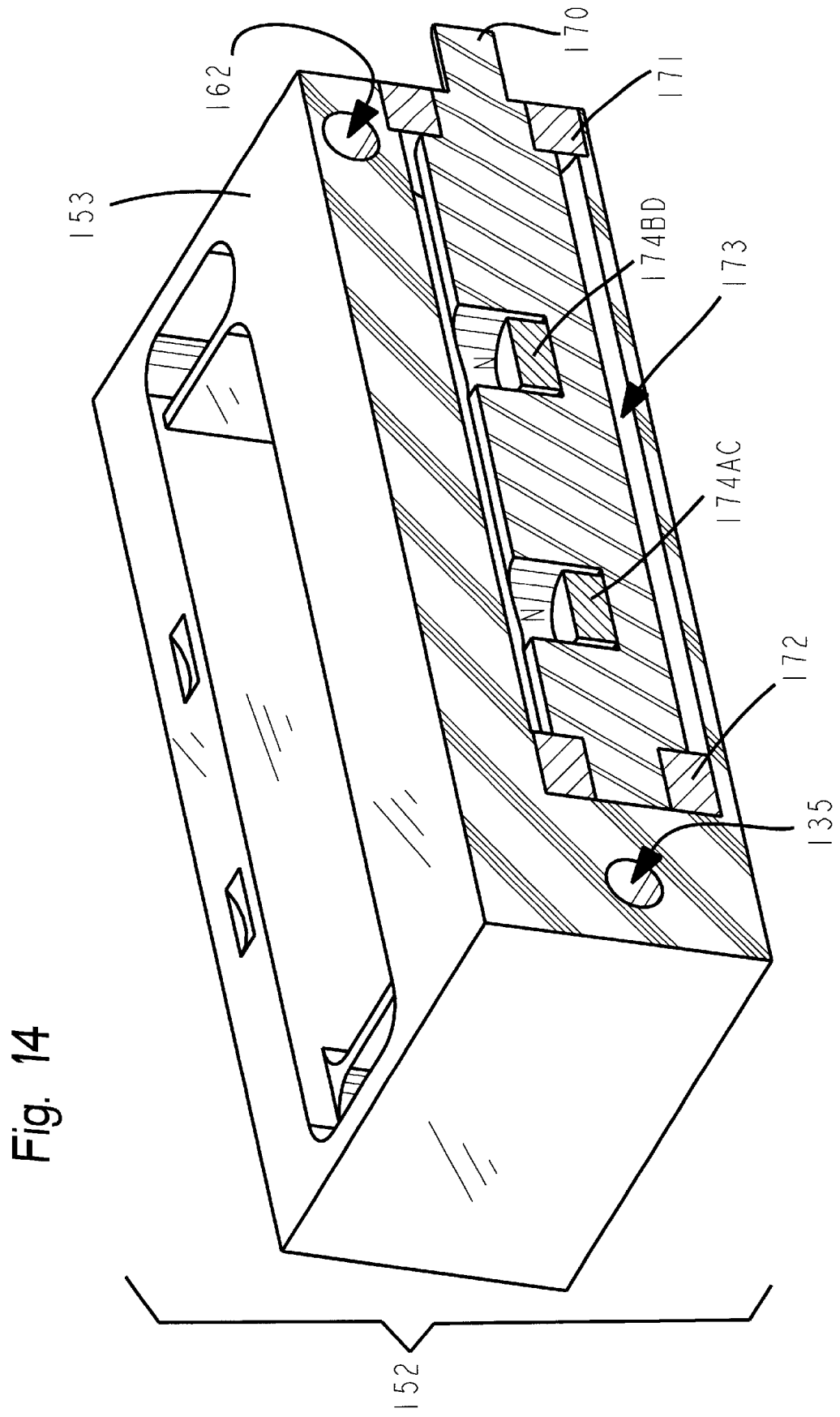
FIG. 14 is an isometric view with portions thereof removed of the water bath sub-assembly depicted in FIG. 13.

FIG. 13 and FIG. 14 illustrate the water bath assembly 152 of the first embodiment of the present invention. Water bath assembly 152 contains water bath body 153. Water bath body 153 contains, trough 154 and trough 155, inlet chamber 156 and inlet chamber 157, dam 168 and dam 169, outlet chamber 158 and outlet chamber 159, inlet port 160, outlet port 161, inlet link hole 162, gap 164 and gap 165, and plugged hole 163. Constant temperature water enters inlet port 160, and then flows from inlet port 160 to inlet chamber 156. The constant temperature water then flows through gap 164 into trough 154. When the constant temperature water level in trough 154 reaches the top of dam 168 it will flow over dam 168 into outlet chamber 158, and exit the water bath through outlet port 161. Therefore, the water level in trough 154 will be determined by the height of dam 168. When the water level in inlet chamber 156 reaches the level of the bottom of inlet link hole 162, it will flow through inlet link hole 162 into inlet chamber 157, and then through gap 165 into trough 155, where the water level will rise until it reaches the top of dam 169, and then flow over dam 169 into outlet chamber 159, through outlet link hole 135, into outlet chamber 158, and then out through outlet port 161. Blind hole 173 of water bath body 153, contains a magnetic driveshaft assembly that contains inner bearing 172, outer bearing 171, driveshaft 170, and permanent drive magnet 174AC and permanent drive magnet 174BD. Permanent drive magnets 174AC and 174BD are preferably high energy rare earth magnets such as Neodymium 27 magnets, but can be any type of permanent magnet with a strong enough magnetic field to drive the follower magnets as described at the beginning of this section, and as will be described below. An electric motor, or air motor, or any other source of rotational power (not shown), is used to rotate drive shaft 170, and hence rotate permanent drive magnets 174AC and 174BD about the centerline of driveshaft 170. Inlet link hole 162 is elevated above inlet port 160, to avoid drive shaft 170 and outer bearing 171. The centerline of plugged hole 163 is coincident with the center line of inlet link hole 162. Plugged hole 163 is used to create inlet link hole 162. Once inlet link hole 162 is created, plugged hole 163 is plugged.

Figure 16:
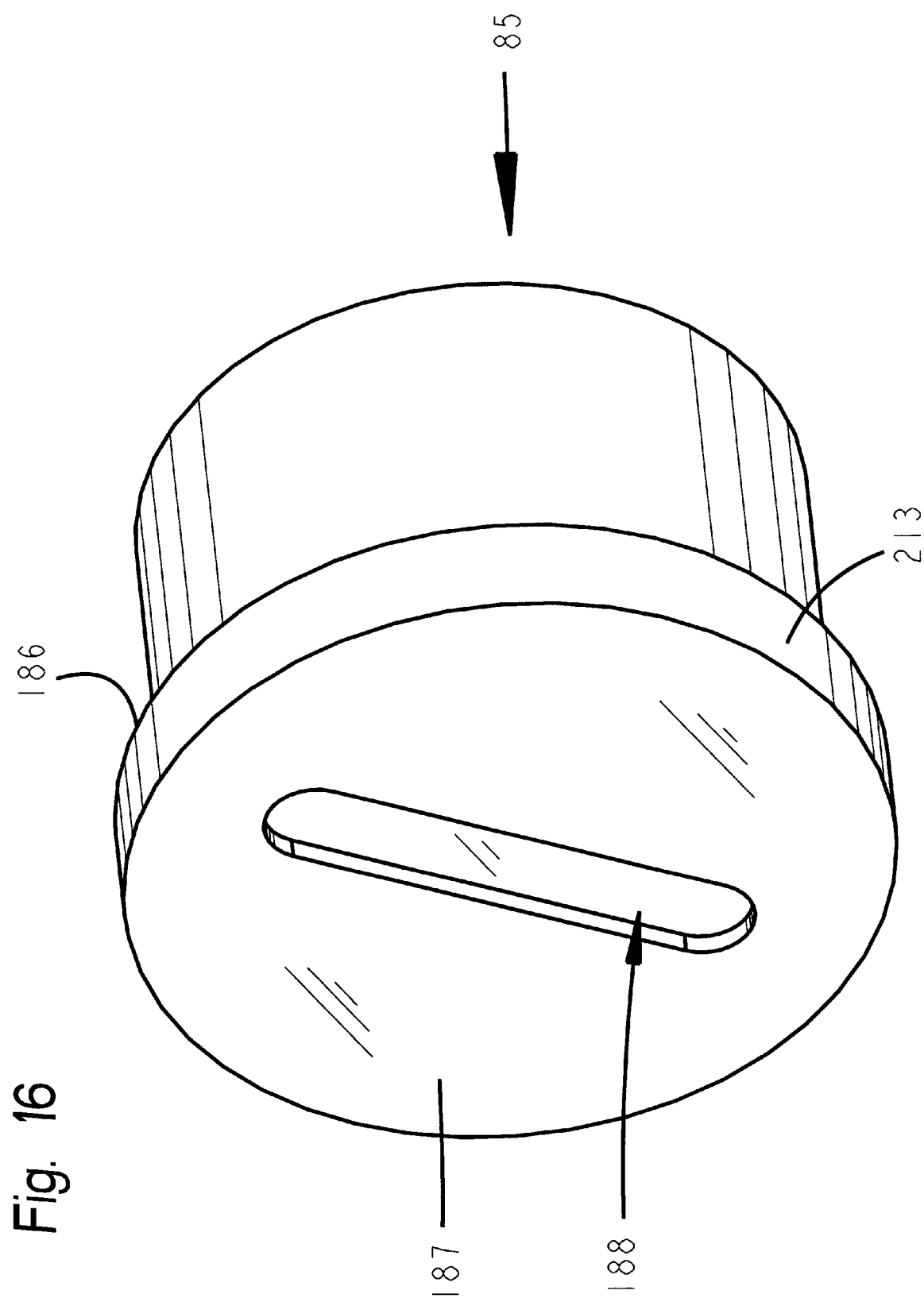
FIG. 16 is an isometric view of a check valve plug, which is a component of the nest sub-assembly depicted in FIG. 7.
Figure 17:
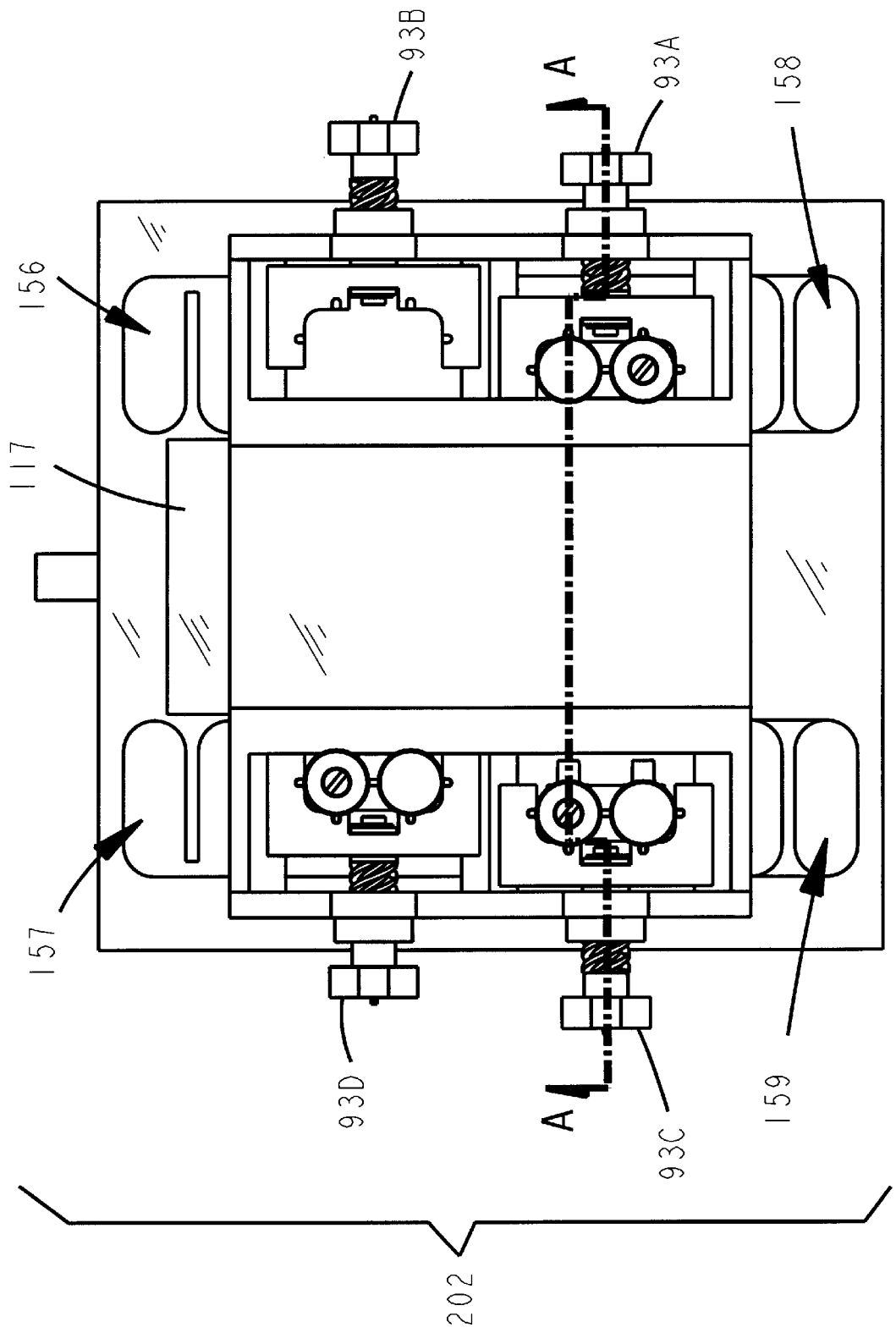
FIG. 17 is a top view of the complete apparatus of the first embodiment of the present invention, including the reusable instrument, with three disposable devices, depicted in FIG. 15.

Referring to FIGS. 15 through 20, a complete constant temperature mixing and storage apparatus 202 of the first embodiment of the present invention containing all of the above mentioned components can be understood. FIG. 15 shows a constant temperature mixing and storage apparatus 202, comprised of a water bath assembly 152 as described above, a manifold assembly 125 as described above, and two nest assemblies 201 as described above, the nest assemblies 201 being mounted on either side of the manifold assembly 125. The constant temperature mixing and storage apparatus 202 shown in FIG. 15 and FIG. 17 contains four nests, nest 90A, nest 90B, nest 90C, and nest 90D. Nest 90A and nest 90D contain disposable devices 200A and 200D respectively, and are shown in the operational or in position. Nest 90B and nest 90C are shown in the out or non operational position. Nest 90C contains disposable device 200C, and nest 90B is empty (i.e. does not contain a disposable device. All of the components assembled as shown in FIG. 15 and FIG. 17 excluding disposable devices 200A, 200C, and 200D, comprise a reusable instrument. Referring to FIG. 2, FIG. 3, FIG. 7, FIG. 10, FIG. 15, and FIG. 17, a disposable device 200 is positioned in a nest by inserting the disposable device 200 into a nest 90 so that alignment tabs 23, 24, 45, and 46 of disposable device 200 are inserted into tab slots 104, 105, 106, and 107 respectively, of nest 90. When the tabs are inserted into their respective slots the disposable device 200 will be correctly positioned in the X, Y, and Z directions. This alignment method allows for the disposable device 200 to be quickly and accurately inserted into a nest 90, and also allows for quick and easy removal of the disposable device 200 from nest 90, without connecting and disconnecting gas tubing to gas tubes 25 and 26 of disposable device 200.

Figure 18:
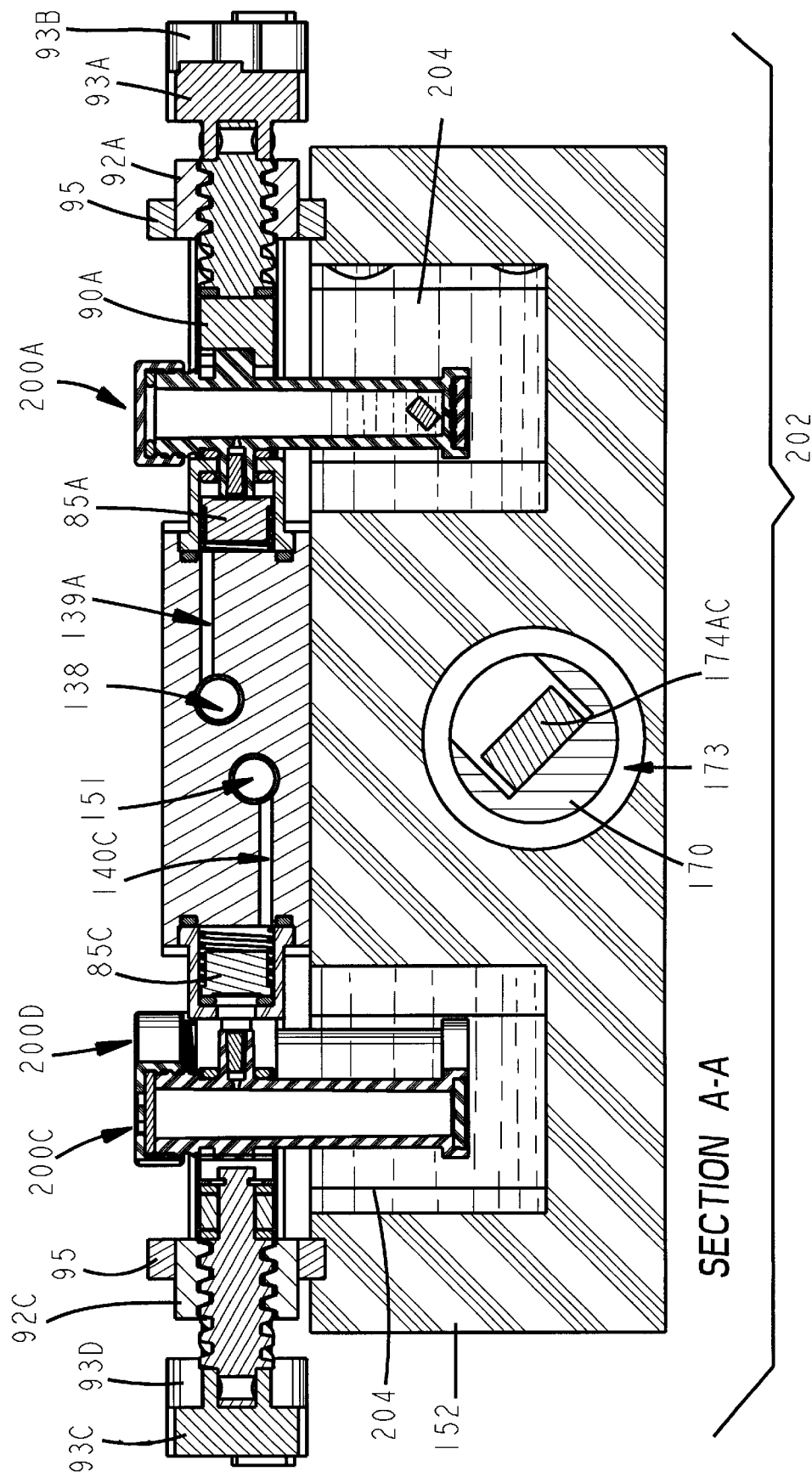
FIG. 18 is a cross-sectional view of the apparatus depicted in FIG. 15, and FIG. 17, taken through section A—A of FIG. 17.

FIG. 18 shows cross-section AA, taken through offset cross-section line AA shown in FIG. 17. FIG. 19 shows in greater detail the portion of offset cross-section AA through the centerline of the mix cylinder portion of disposable device 200A. FIG. 19 depicts a typical cross-section through any mix cylinder in any nest, hence generic numbers are used to represent the various details (for example the generic number 21 is used and not 21A).

Referring to FIG. 2, FIG. 3, FIG. 9, FIG. 12, FIG. 15, FIG. 16, FIG. 17, FIG. 18, and FIG. 19, one can see how the constant temperature mixing and storage apparatus 202, provides a gas source to both the mix gas tube 25 and storage gas tube 26 of all of the disposable devices 200 that are inserted in nests, positioned in the operational or in position, by automatically opening a pair of check valves for each disposable device 200 in the operational position, and how the check valves automatically close when a disposable device 200 is not in the operational position. When the disposable device 200 is in the in position, mix gas o-ring 17 is compressed between mix o-ring boss 35 of disposable device 200, and surface 133 of nest guide 89, effectively sealing mix o-ring boss 35 of disposable device 200 to surface 133 of nest guide 89. When the disposable device 200 is in the in position as shown in FIG. 19, mix gas tube 25 will be inserted into its mating port 101 of nest guide 89, with the end surface 210 of mix gas tube 25 pressing against surface 187 of check plug 85, thus pushing surface 187 of check plug 85 away from check o-ring 86, and further compressing check spring 84 between surface 186 of check plug 85, and surface 211 of manifold 115. Surface 187 of check plug 85 contains channel 188, which prevents the interior 27 of mix gas tube 25 from being blocked off when the end surface 210 of mix gas tube 25 presses against surface 187 of check plug 85. A gap 209 exists between surface 212 of check valve counterbore 87 and surface 213 of check plug 85, and between surface 212 of check valve counterbore 87 and check spring 84. Hence whenever a disposable device 200 is in the operational or in position as shown in FIG. 19, a flow path will exist from mix chamber 21 of disposable device 200, through port 50 of disposable device 200, through chamber 123 of disposable device 200, through channel 20M of disposable device 200, through channel 188 of check plug 85, through gap 209 in check valve counterbore 87, through port 139 of manifold 115, through hole 138 of manifold 115, into mix counterbore hole 149 of manifold end cap 117. Mix counterbore hole 149 of manifold end cap 117 is connected to a gas source, either through a manual valve (not shown), or through an automatic valve (not shown). Therefore, mix chamber 21 of disposable device 200 will be placed in gas flow communication with mix counterbore hole 149 of manifold end cap 117, of manifold assembly 125 of constant temperature mixing and storage apparatus 202, when the disposable device 200 is in the operational or in position. This will be the case for all disposable devices in nests that are in the operational or in position. Hence, referring to FIG. 12, FIG. 15, and FIG. 17, the disposable devices 200A and 200D, in nests 90A and 90D, would have their mix chamber 21 in gas flow communication with mix counterbore hole 149 of manifold end cap 117.

FIG. 20 shows in greater detail the portion of offset cross-section AA through the centerline of the storage cylinder portion of disposable device 200C. FIG. 20 depicts a typical cross-section through any storage cylinder in any nest, hence generic numbers are used to represent the various details (for example the generic number 22 is used and not 22C). FIG. 20 depicts in cross-section the storage chamber of a typical disposable device in the out position. Referring to FIG. 2, FIG. 9, FIG. 12, FIG. 16, and FIG. 20, if the storage cylinder 39 were in the operational or in position (not shown), storage gas tube 26 would be inserted into its corresponding port 101 of nest guide 89, so that storage gas o-ring 18 would be compressed between storage o-ring boss 36 of disposable device 200, and surface 133 of nest guide 89, effectively sealing storage o-ring boss 36 of disposable device 200 to surface 133 of nest guide 89. When the disposable device 200 is in the in position, storage gas tube 26 will be inserted into its mating port 101 of nest guide 89, with the end surface 211 of storage gas tube 26 pressing against surface 187 of check plug 85, thus pushing surface 187 of check plug 85 away from check o-ring 86, and further compressing check spring 84 between surface 186 of check plug 85, and surface 211 of manifold 115. Surface 187 of check plug 85 contains channel 188, which prevents the interior 28 of storage gas tube 26 from being blocked off when the end surface 211 of storage gas tube 26 presses against surface 187 of check plug 85, when disposable device 200 is in the in position. A gap 209 exists between surface 212 of check valve counterbore 87 and surface 213 of check plug 85, and between surface 212 of check valve counterbore 87 and check spring 84. Hence whenever a disposable device 200 is in the operational or in position, a flow path will exist from storage chamber 22 of disposable device 200, through port 49 of disposable device 200, through chamber 124 of disposable device 200, through channel 20S of disposable device 200, through channel 188 of check plug 85, through gap 209 in check valve counter-bore 87, through port 140 of manifold 115, through hole 151 of manifold 115, into storage counterbore hole 150 of manifold end cap 117. Storage counterbore hole 150 of manifold end cap 117 is connected to a gas source, either through a manual valve (not shown), or through an automatic valve (not shown). Therefore, storage chamber 22 of disposable device 200 will be placed in gas flow communication with storage counterbore hole 150 of manifold end cap 117, of manifold assembly 125, when the disposable device is in the operational or in position. This will be the case for all disposable devices in nests that are in the operational or in position. Hence referring to FIG. 12, FIG. 15, and FIG. 17, the disposable devices in nests 90A and 90D, would have it their storage chamber 22 in gas flow communication with storage counterbore hole 150 of manifold end cap 117.

FIG. 20 shows a cross-section through the center of a typical storage cylinder 39 in the out position. Referring to FIG. 12, FIG. 16, and FIG. 20, with storage cylinder 39 in the out position check spring 84 forces check plug 85 to compress check o-ring 86 between surface 214 of check valve counterbore 87, and surface 187 of check plug 85, placing the check valve in the closed state, therefore blocking flow in either direction in the corresponding port 140 of manifold 115. Whenever a disposable device 200 is in the out position its mix cylinder 38 will also be in the out position, and the mix gas tube 25 will also be withdrawn from its port 101 of nest guide 89, and its check valve will also be in the closed state, thus flow will be blocked in either direction in its corresponding port 139 of manifold 115.

Referring to FIG. 2, FIG. 3, FIG. 5, FIG. 6, FIG. 7, FIG. 9, FIG. 12, FIG. 14, FIG. 15, FIG. 16, FIG. 17, FIG. 18, and FIG. 19, one can see how a disposable device 200, and the constant temperature mixing and storage apparatus 202 can be used to test a compound for solubility. The user can use the constant temperature mixing and storage apparatus 202, with as few as one disposable device 200, or as many as the number of nests available on the constant temperature mixing and storage apparatus 202. The following explanation of the process refers to a single disposable device 200, but the same principles will apply when more than one disposable device 200 is used with the constant temperature mixing and storage apparatus 202 The process starts with a nest in the out position as shown in FIG. 15, nest 90B. The screw is as far out as it can go with the knob pointer 180B pointing down. The user will purchase the disposable device assembled. The user will remove the mix cap 13 from the disposable device 200, and place a quantity of compound to be tested (i.e. solute) into the mix chamber 21, then place a follower magnet 52 into the mix chamber 21, and then replace the mix cap 13, making sure that the mix cap 13 is screwed on firmly to create a leak tight seal between mix cap o-ring 15 and the top surface 30 of mix cylinder 38, and between mix cap o-ring 15 and the inside top surface of mix cap 13. The user then removes the storage cap 14, with septum 16, and places a quantity of solvent (a volume greater than or equal to 40 $\mu$l) into the storage chamber 22, and then replaces the storage cap 14 with septum 16, making sure that the storage cap is screwed on firmly so as to create a leak tight seal between the septum 16 and the top surface 31 of storage cylinder 39. The user will then place the disposable device containing solute, solvent, and a follower magnet into the nest, so that the tabs of the disposable device 200 are inserted into the tab slots of the nest 90 as described above, and as shown in FIG. 15, nest 90C containing disposable device 200C. The operator then turns the screw knob 180° clockwise, as shown in FIG. 15, nest 90A, so that the knob pointer 180A points up. The nest with its disposable device will now be in the in or operational position, and as described above the mix cylinder check valve, and storage cylinder check valve will both be in the open position, thus providing a communication path between mix counterbore hole 149 of manifold end cap 117 and mix chamber 21, and between storage counterbore hole 150 of manifold end cap 117 and storage chamber 22. A gas source (i.e. such as filtered compressed air, or dry nitrogen not shown) will be connected to mix counterbore hole 149, and to storage counterbore hole 150, through either manual or automated valves (not shown). The process starts by applying a low gas pressure to storage counterbore hole 150, and thus to storage chamber 22 via the flow path described above. At the same time mix counterbore hole 149 will be vented to atmosphere. This action will cause the solvent in the storage chamber 22 to be forced from storage chamber 22, through channel 41 of bottom cover 12, into chamber 59 of bottom cover 12, through filter element 11, into chamber 60 of body 10, through one or more holes 55 of body 10, into mix chamber 21 of body 10. This action of forcing the solvent through the filter wets the pores of the filter, hence flow will stop after storage chamber 22, channel 41, and chamber 59 have been emptied of solvent, as long as the applied gas pressure in the storage chamber 22 is less than the bubble point pressure of the filter for the type of solvent being used. Disposable devices that have been tested using water as the solvent, and a 0.45 μm pore size filter element, with a bubble point pressure of approximately 30 p.s.i., required less than 2 p.s.i. to transfer water from the storage chamber, through a 0.45 μm pore size filter into the mix chamber, or vice versa. The motor (not shown) that rotates drive shaft 170 of water bath assembly 152, can be either turned on at this point to rotate drive shaft 170 at a predetermined rotational speed, or the motor could have been turned on prior to this time. The one or more drive magnets 174, attached to drive shaft 170 will rotate with driveshaft 170. The appropriate rotating drive magnet 174 will cause the follower magnet 52 in the mix chamber 21 of disposable 200 to rotate with a tumbling action about an axis parallel to the central axis of driveshaft 170, at the "rotational speed the rotating driveshaft 170", as previously described. Referring to FIG. 3, follower magnet 52 rotates with a tumbling action in the direction of arrow 54, causing the solution and excess solute in mix chamber 21 to flow in the direction illustrated by arrows 53. This causes the solution and excess solute to be thoroughly mixed throughout the entire solution, thus causing the solute to dissolve into solution very rapidly. Evaporation of the solution in the mix chamber 21 is minimized by making the cross-section of channel 20 in gas plug 19 as small as possible. Since mix chamber 21 is a sealed chamber except for the opening through channel 20M (shown in FIG. 19) of gas plug 19, making channel 20 of gas plug 19 very small will reduce the evaporation rate in the mix chamber 21 to an acceptable level. Furthermore, evaporation is a function of time, and since the mixing action of the tumbling magnet minimizes the time needed to saturate the solution with solute, evaporation is further reduced by reducing the time required to reach saturation.

At a pre determined time interval, determined by the user from experience, gas pressure (below the bubble point of the filter element 11) will be applied to the mix counterbore hole 149 of manifold end cap 117, and storage counterbore hole 150 of manifold end cap 117 will be vented to atmosphere. This will force the solution in mix chamber 21 to flow through the one or more holes 55, into chamber 60 of body 10, through filter element 11, into chamber 59 of bottom cover 12, through channel 41 of bottom cover 12, into storage chamber 22. If the pore size of filter element 11 is less than the minimum particle size of the solute, all of the excess solute will be left behind in mix chamber 21. The user can then take a sample of the solution by inserting a needle attached to a syringe (not shown)., through opening 44 of storage cap 14 and through septum 16, into storage chamber 22, and withdrawing the required volume of solution for analysis, using standard solubility analysis techniques, which are not a part of the present invention. Septum support rib 29 of storage cap 14 provides additional support for septum 16 while storage chamber 22 is pressurized. Instead of using a manual syringe and needle, an automated robotic system could be used to take samples of solution.

After the sample has been taken from storage chamber 22, the gas pressure will be reversed by applying the gas pressure to storage counterbore hole 150, and venting mix counterbore hole 149, both of manifold end cap 117. This will cause the solution to be forced through channel 41 of bottom cover 12, into chamber 59 of bottom cover 12, through filter element 11, into chamber 60 of body 10, through the one or more holes 55, back into mix chamber 21, where the solution will continue to mix with the excess solute.

The process of mixing in the mix chamber, and taking samples for analysis from the storage chamber will continue until the user determines that enough samples have been taken, or until all of the solution has been removed. FIG. 18 shows that the bottom portion of all of the disposable devices inserted in nests of the constant temperature mixing and storage apparatus 202 will be immersed in a re-circulating constant temperature solution 204, in water bath 152, thus keeping the temperature of the solution in the mix, and storage chambers constant. Once the process is complete the user will remove the disposable device 200 from the constant temperature mixing and storage apparatus 202 by turning the screw knob 93 counterclockwise 180°. This action will cause the nest 90 to move to the out position, thus placing disposable device 200 in the out position, which in turn causes the corresponding mix check valve, and the storage check valve to automatically close.

Referring to FIG. 2, FIG. 3, FIG. 5, FIG. 12, and FIG. 15, an alternate way to begin the process would be to have the user add the solute and follower magnet to mix chamber 21 of disposable device 200, and then insert disposable device 200 into a nest of constant temperature mixing and storage apparatus 202, and then place the nest in the in position as described above, and either manually or automatically apply pressurized nitrogen to either the mix counterbore hole 149, or the storage counterbore hole 150, and vent the unpressurized counterbore hole, so as to purge the interior of manifold assembly 125, and the interior of any disposable devices 200 attached to the constant temperature mixing and storage apparatus 202 with nitrogen. Once purged, the nitrogen pressure in the manifold will be reduced to a very low value, or to 0 p.s.i. The valves (not shown) connected to both mix counterbore hole 149, and storage counterbore hole 150, would be closed to keep the interior of manifold assembly 125, and interior of the disposable devices 200 filled with nitrogen. The solvent could then be dispensed either manually using a syringe with needle, or automatically using a robot with needle, through septum 16, into the storage chamber 22 of disposable device 200. The process would then continue as described above with the exception that after completing a cycle where the solution is either forced from the storage chamber 22, through the filter element 11, into the mix chamber 21, or vice versa, the valve attached to the vented counterbore hole of manifold end cap 117 would be closed to maintain a nitrogen atmosphere in the interior of manifold assembly 125, and in the interior of the disposable devices 200 plugged into constant temperature mixing and storage apparatus 202.

If keeping an inert atmosphere inside the system is not necessary, an alternate way for the user to take samples for analysis would be to remove storage cap 14 each time a sample is required. This method would, however increase evaporation which is undesirable.

The disposable device could also be used without the reusable apparatus by connecting mix gas tube 25 to a gas source with a length of tubing, and by connecting storage gas tube 26 to a gas source with a second length of tubing. The disposable device could then be placed in a constant temperature water bath, with a rotating magnet disposed below the water bath. The process described above of alternate mixing and sample taking could then be performed, although it would be more difficult and messy.

In summary the first embodiment of the present invention provides an apparatus consisting of a disposable device, and a reusable instrument. This apparatus allows a user to easily and quickly mix a solvent and solute, to create a solution, and provides a means to separate the solution form excess solute, and provides a means to sample the solution less excess solute, and provides a means to perform the process at a constant temperature. The user need only load the necessary solute and solvent with a follower magnet into the disposable device, and then insert the device into the reusable instrument, without connecting or disconnecting any tubing, and then remove the required samples from the disposable device for analysis. The loading of solvent and removal of samples can also be automated.

Figure 21:
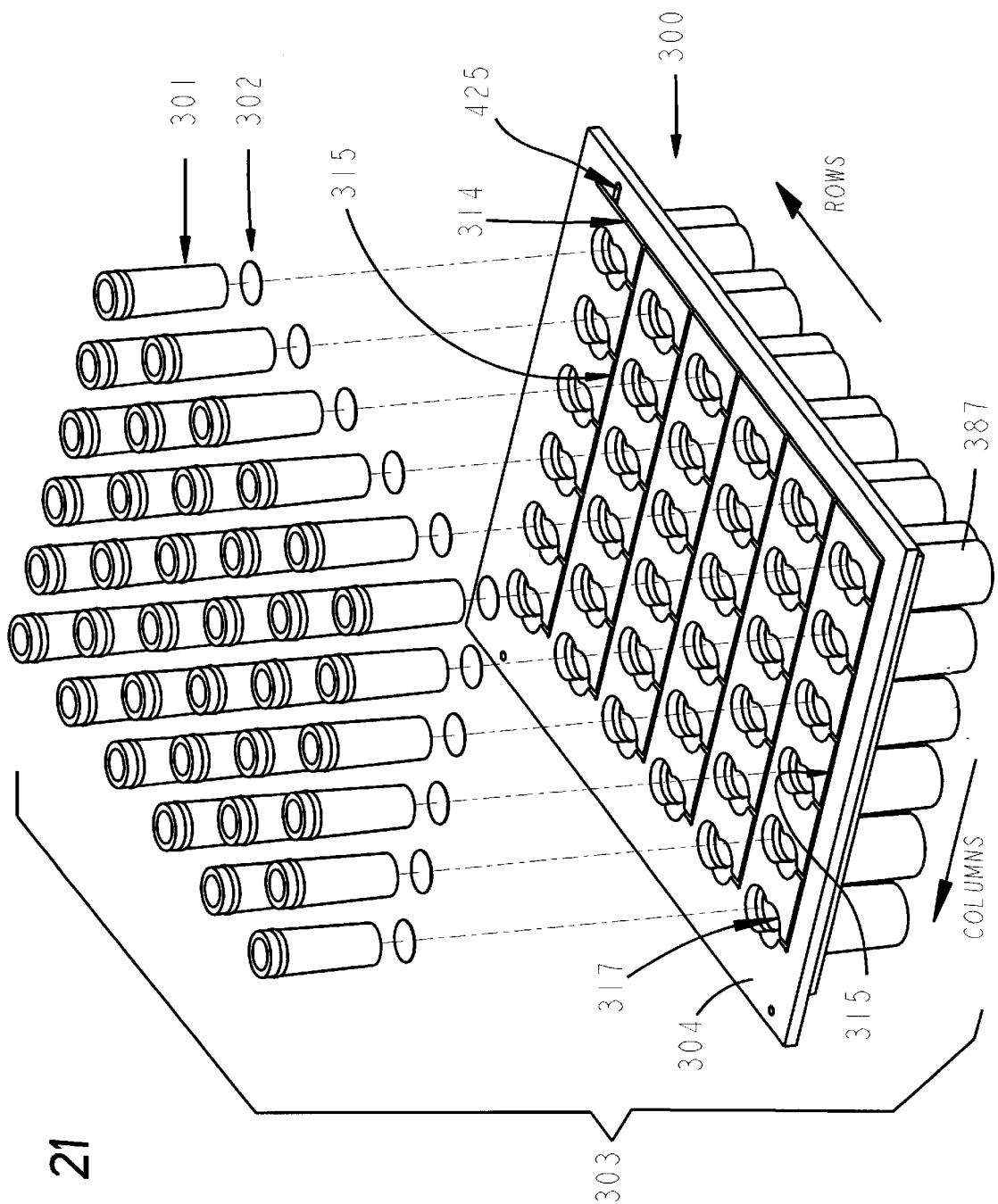
FIG. 21 is an exploded isometric view showing the components of the disposable device of the second embodiment of the present invention.
Figure 22:
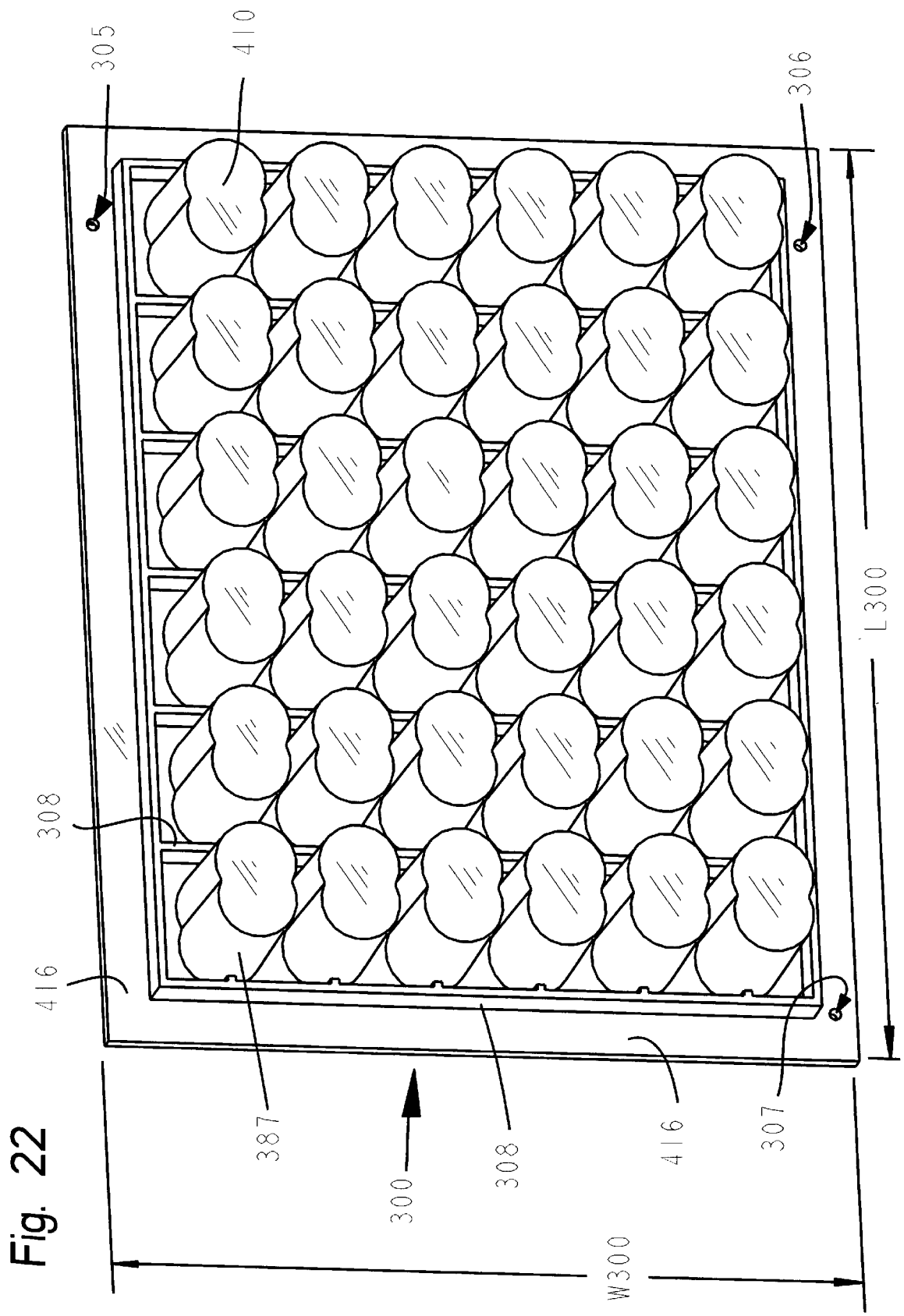
FIG. 22 is a bottom isometric view of the well plate which is a component of the disposable device depicted in FIG. 21.
Figure 23:
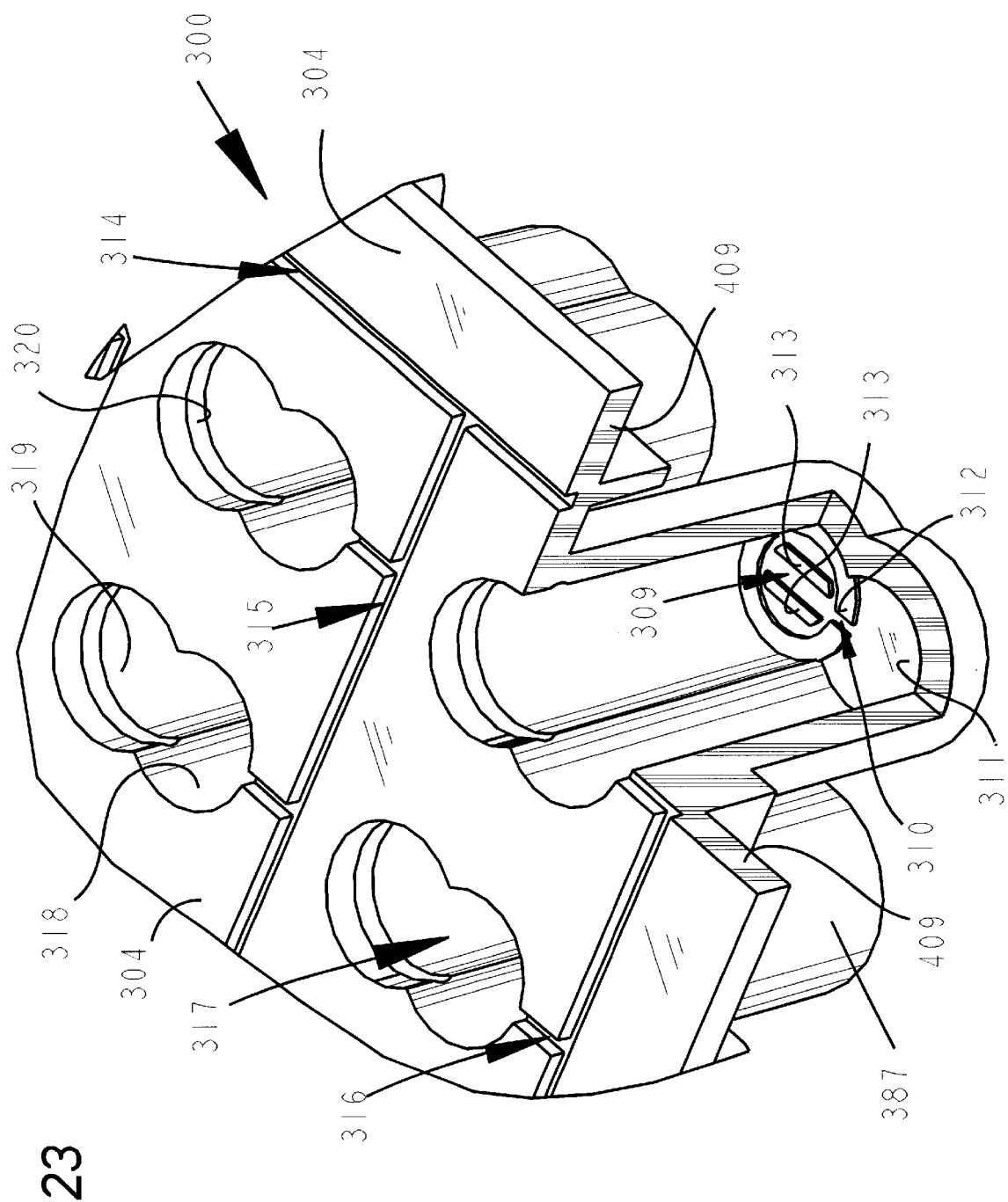
FIG. 23 is a partial isometric view, with portions thereof removed, of the well plate depicted in FIG. 22.

FIGS. 21 through 26, and FIG. 38 show the disposable device 303 of a second embodiment of the present invention. Disposable device 303 is comprised of well plate 300, containing one or more wells 317, one or more cups 301, the number of cups 301 being equal to the number of wells 317 in well plate 300, and one or more filter elements 302, the number of filter elements 302 being equal to the number of cups 301. The interior profile of each well being formed by the non-overlapping portions of two overlapping closed planar curves. In FIG. 23 each well 317 has a profile in the shape of a figure eight, with the two overlapping closed planar curves taking the form of two overlapping circles, with the distance between the centers of the two circles being less than the sum of the radii of the two circles. Well 317 is formed by cylindrically shaped side wall 318, cylindrically shaped side wall 319, and bottom wall 311. Side walls 318 and 319 should contain a slight taper for ease in molding. Filter support ribs 313, and filter support rib 312 protrude from bottom surface 311. Chamber 309 is formed inside of filter support rib 312, and around filter support ribs 313. Filter support rib 312 contains slot 310. Side wall 319 contains groove 320. Filter support rib 312 and filter support ribs 313. 0.025", preferably not more than 0.005" so as to minimize the volume of chamber 309. Cup 301 contains storage chamber 328 in the interior of cup 301, formed by side wall 331, which is cylindrical in shape, but that should contain a slight taper for ease in molding, and bottom wall 330, which may be conical in shape as shown. Bottom wall 330 contains port 329. The outside of cup 301 is formed by side wall 391, which is cylindrical in shape, but that should contain a taper equal to the taper of side wall 319 of well 317, of well plate 300, and by a bottom wall that contains filter sealing surface 326, filter support ribs 324 and 327, circular grooves 322 and 325, and slot 323 which provides a flow path between the circular grooves. Ring 321 protrudes from side wall 391 of cup 301. Filter element 302 is sealed to surface 326 (shown cross-hatched in FIG. 25) on the bottom of cup 301. Alternately cup 301 could have an open bottom thus eliminating filter support ribs 324 and 327 and circular grooves 322 and 325, and slot 323, with filter element 302 sealed to surface 326 (shown cross-hatched in FIG. 25) on the bottom of cup 301. Another alternative would be to have a plurality of holes in the bottom of cup 301 with or without filter support ribs 324 and 327, circular grooves 322 and 325, and slot 323, with filter element 302 sealed to surface 326 (shown cross-hatched in FIG. 25) on the bottom of cup 301. A sub-assembly composed of cup 301 and filter element 302 is inserted into the portion of each well 317 containing groove 320, so that ring 321 of cup 301 snaps into groove 320 of well 317 of well plate 300. When cup 301 is snapped into position in well 317, the top surface 392 of cup 301 will be flush with top surface 304 of well plate 300, and filter element 302 sealed to the bottom of cup 301 will rest against or very close to filter support rib 312 and filter support ribs 313.

Figure 38:
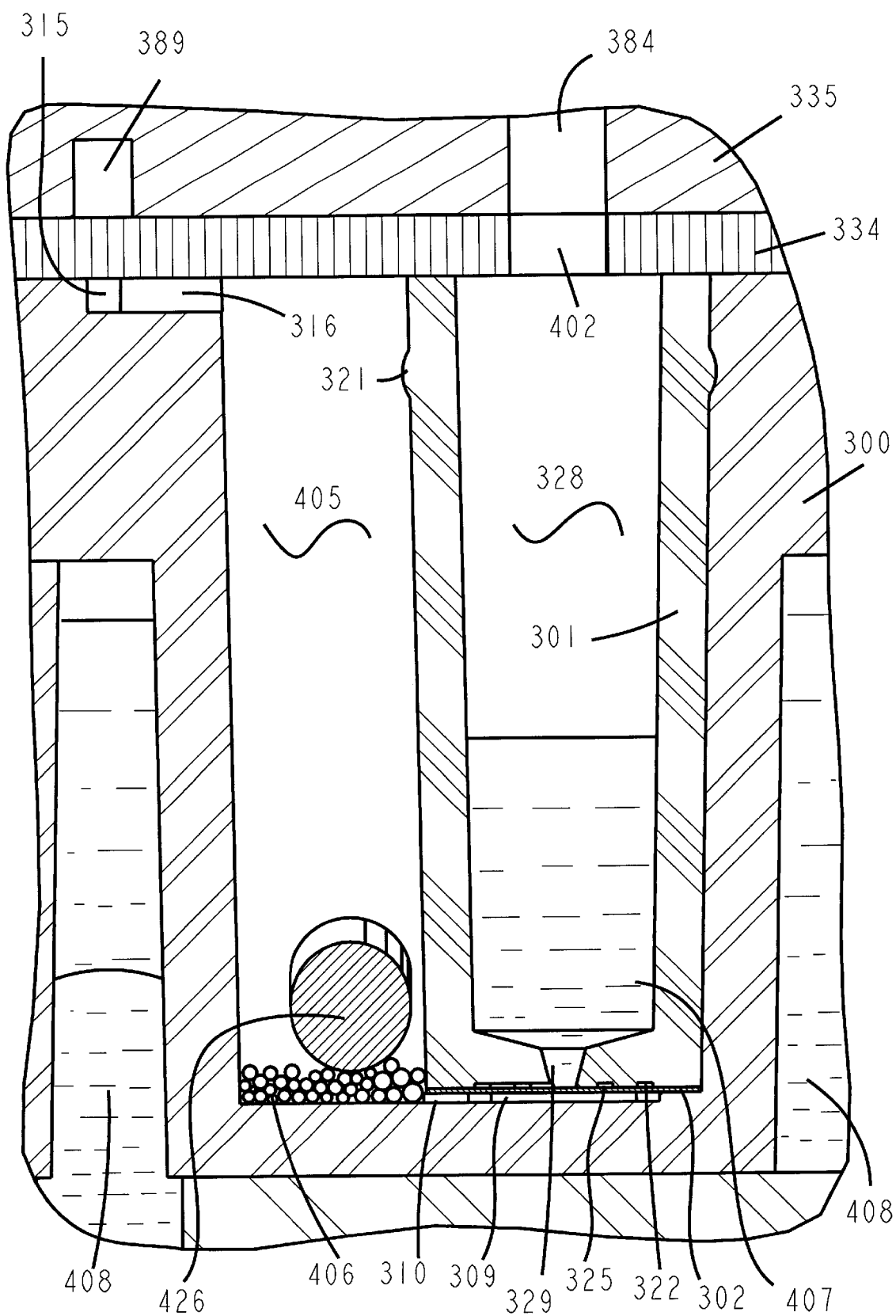
FIG. 38 shows in greater detail, a cross-section through a typical pair of chambers depicted in FIG. 37.

With cup 301 snapped into place in well 317, well 317 is divided into a first chamber and a second chamber FIG. 38 shows the second chamber as mix chamber 405, and the first chamber as storage chamber 328, separated by filter element 302 as shown in FIG. 38. Well plate 300 contains main gas channel 314, gas channels 315, and well gas channels 316, all of which are interconnected. Main gas channel 314 feeds gas channels 315, which in turn feed well gas channels 316. Well plate 300 contains one gas channel 315 for each column of wells 317 (as shown in FIG. 21), and one well gas channel 316 for each well 317. Well plate 300 has a flange 409 around its outer periphery. A grid of stiffening ribs 308 protrude from the bottom of well plate 300, to keep the top surface 304 of well plate 300 flat. If wells 317 protrude below the bottom surface of flange 409 they will contain outer side wall 309, and outer bottom wall 410 flange 409 of multi-well plate 300.

Figure 27:
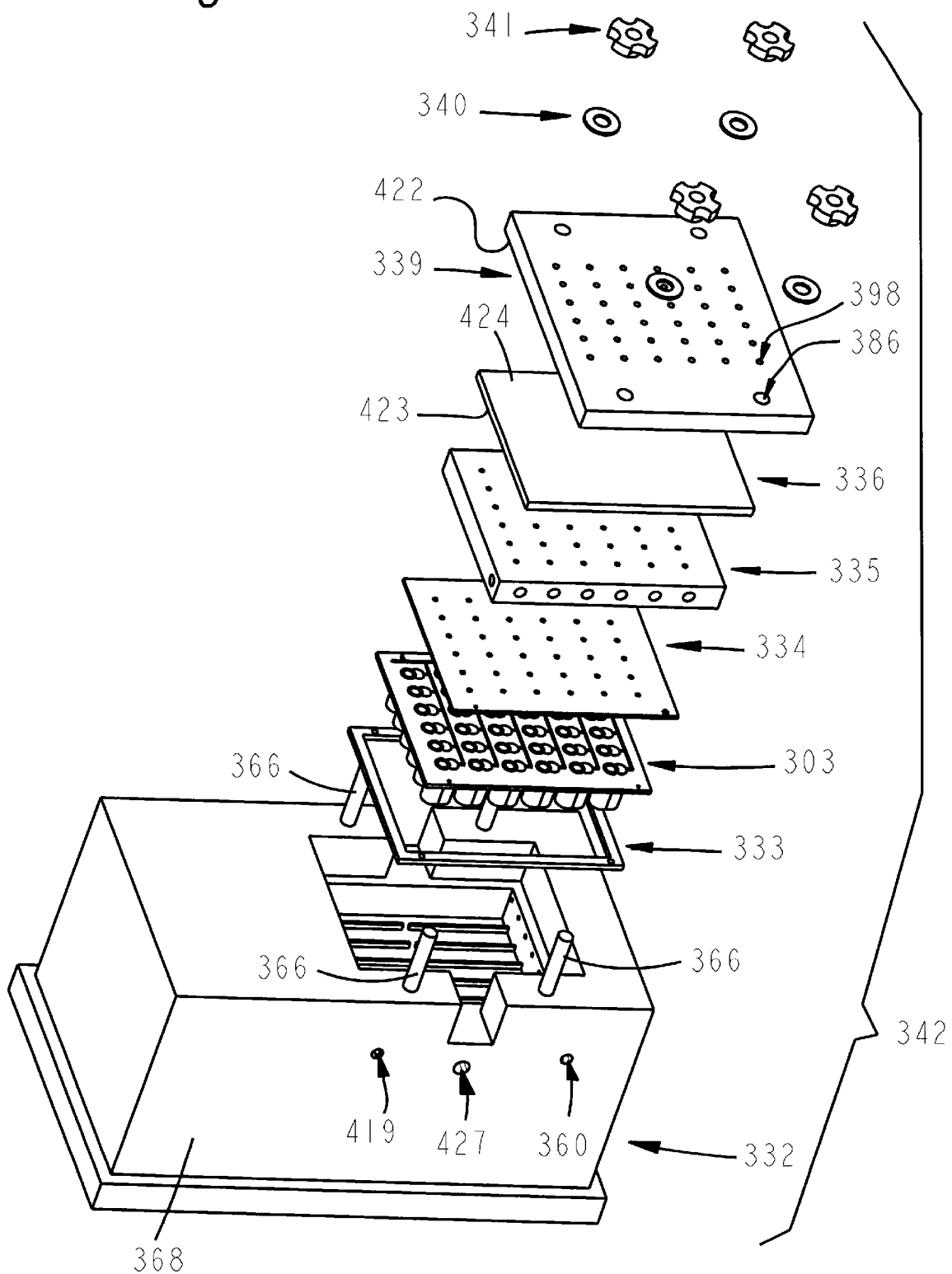
FIG. 27 is an exploded isometric view of the second embodiment of the present invention, showing most of its components.
Figure 28:
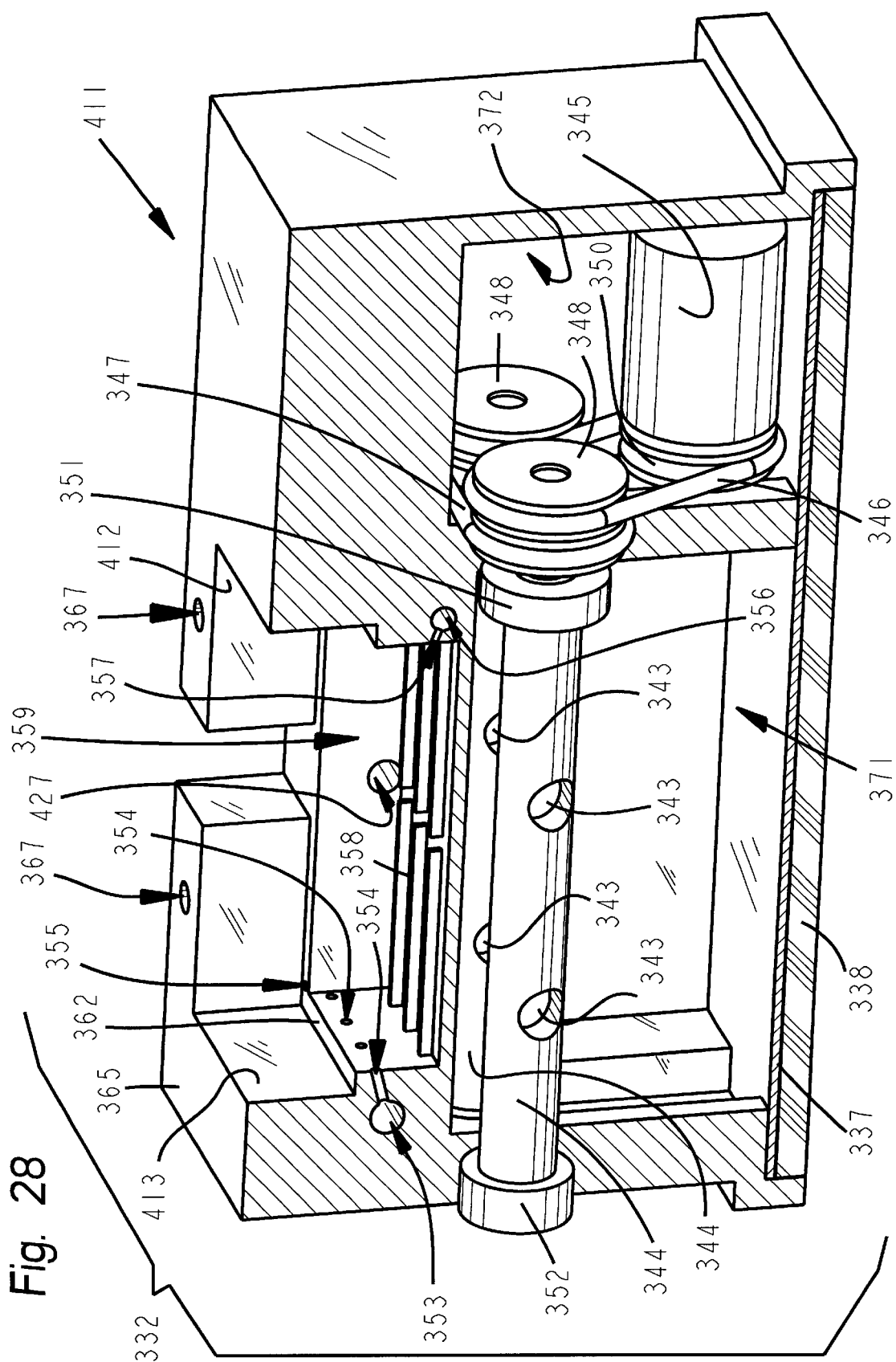
FIG. 28 is an isometric view with portions thereof removed, of the water bath assembly depicted in FIG. 27.
Figure 29:
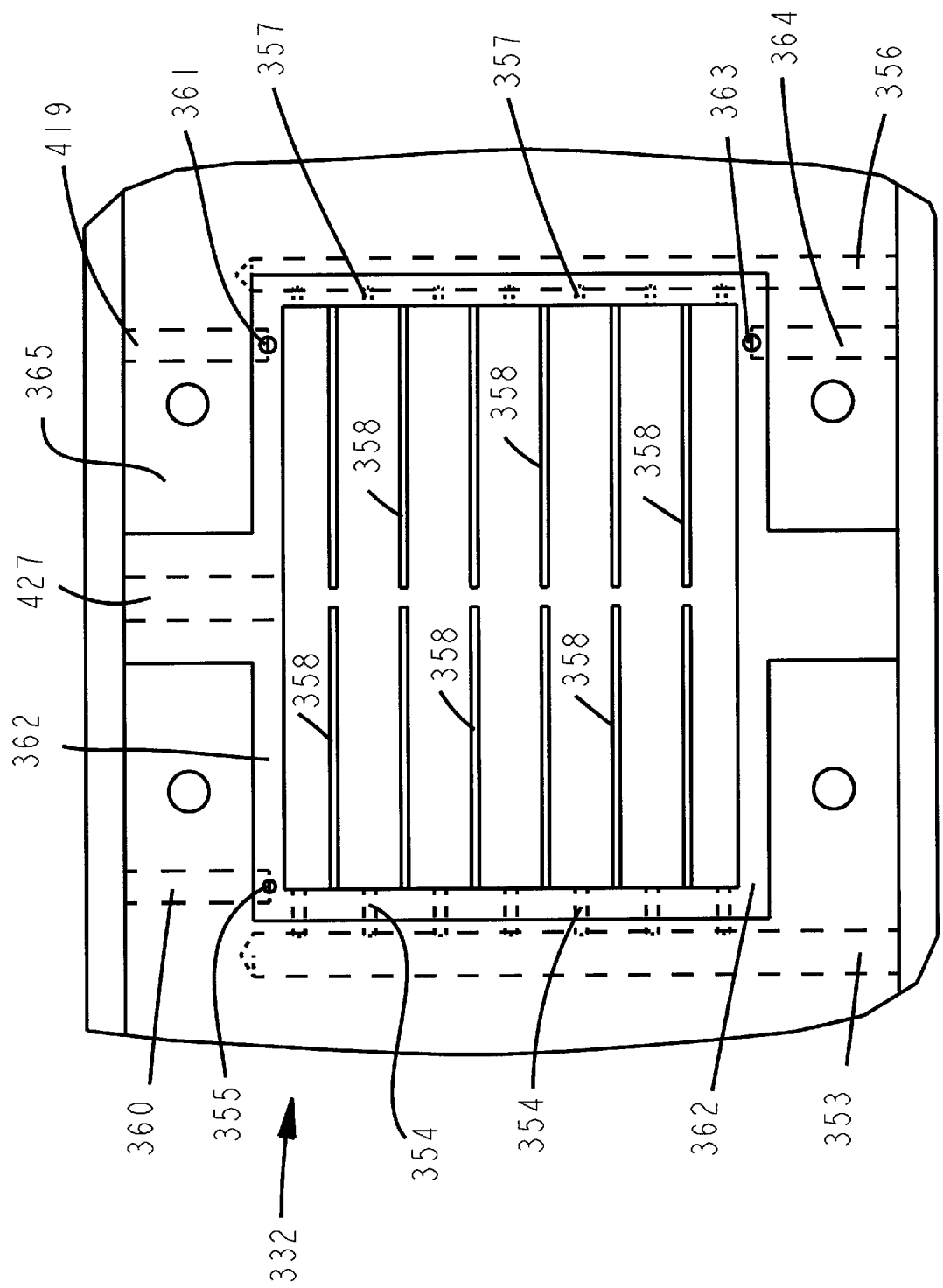
FIG. 29 is a partial top view of the water bath assembly depicted in FIG. 28.
Figure 30:
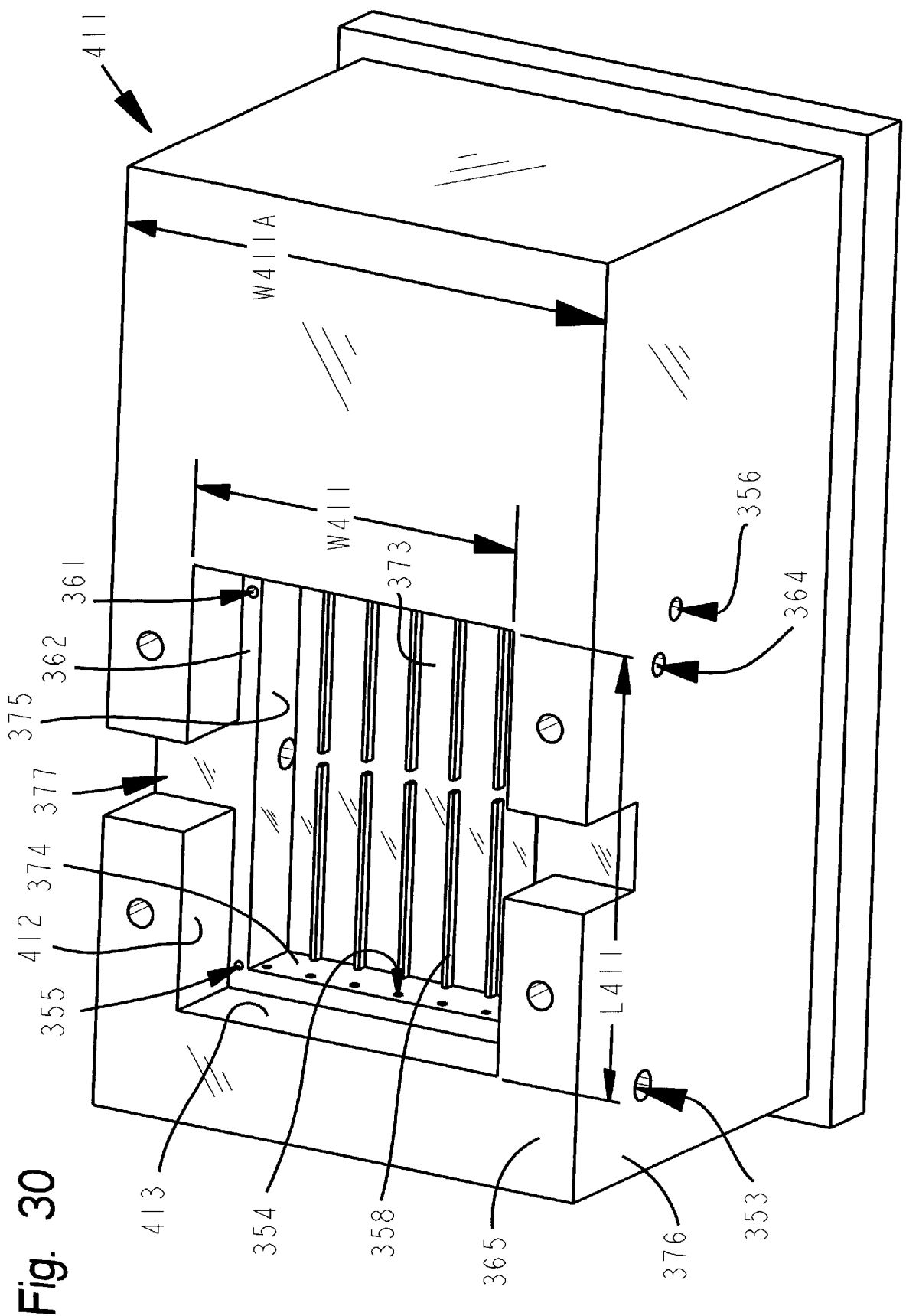
FIG. 30 is an isometric view of the water bath assembly depicted in FIG. 28.
Figure 31:
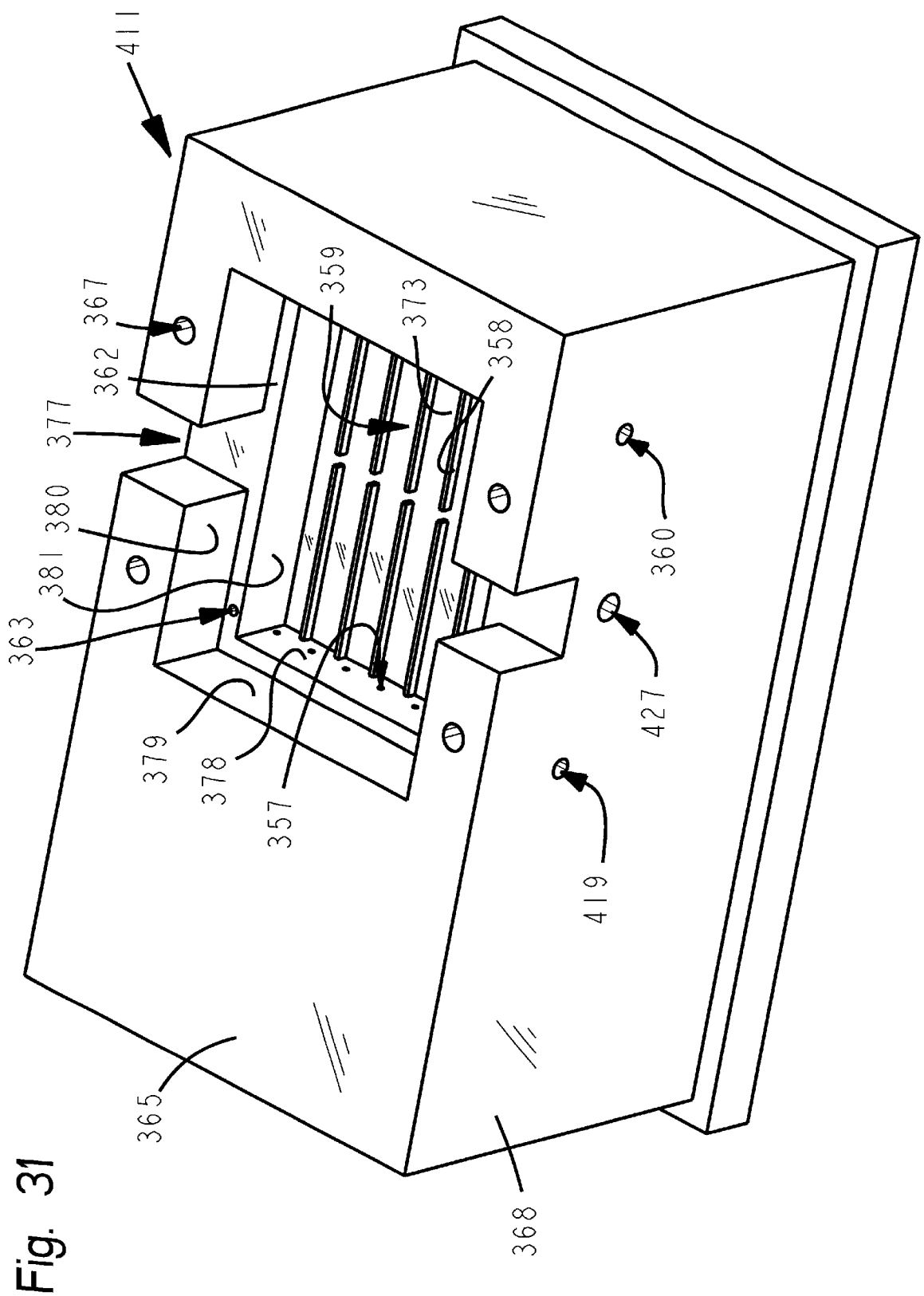
FIG. 31 is an isometric view of the water bath assembly depicted in FIG. 28, rotated 180° form the view shown in FIG. 30.
Figure 32:
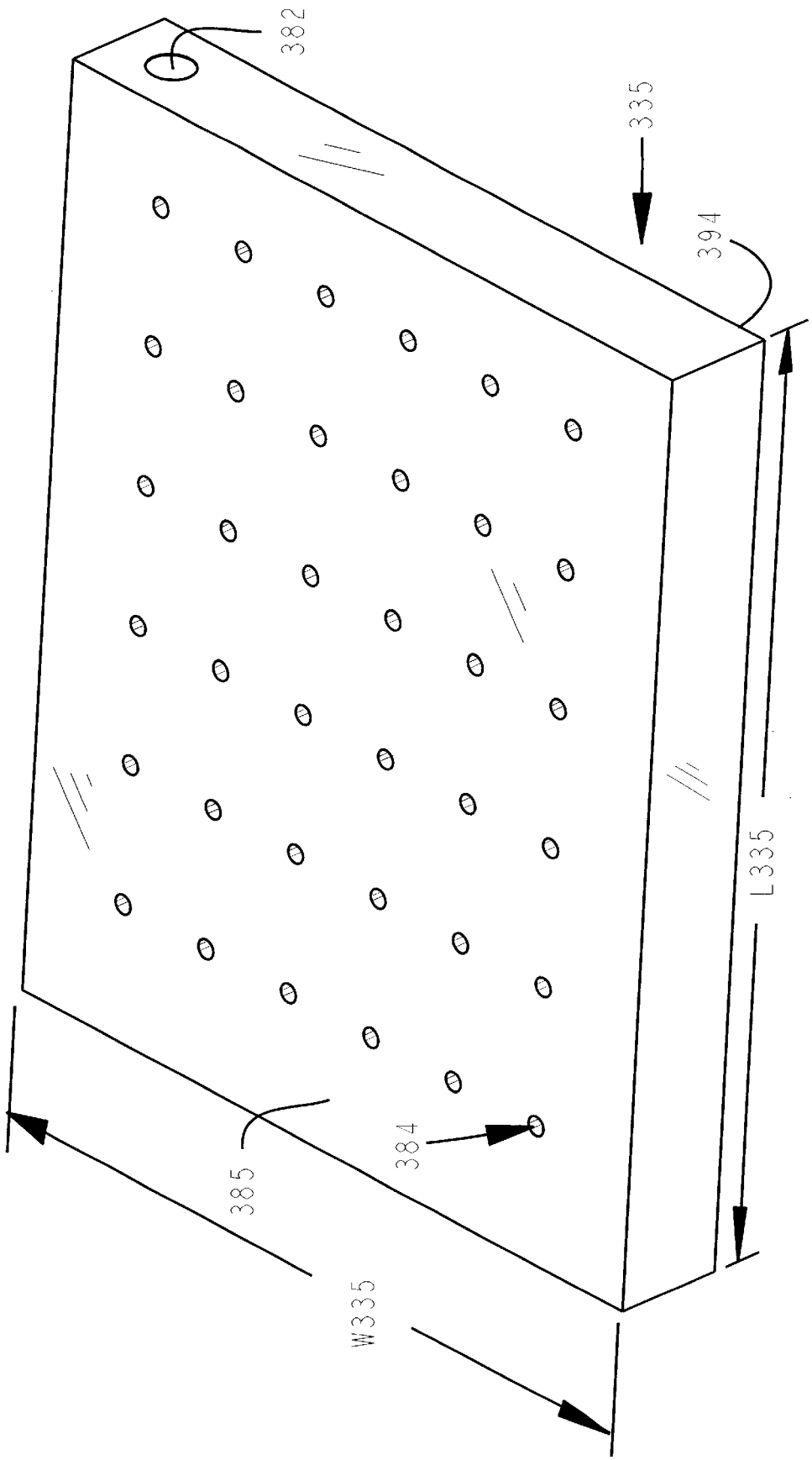
FIG. 32 is an isometric view of the gas manifold depicted in FIG. 27.
Figure 33:
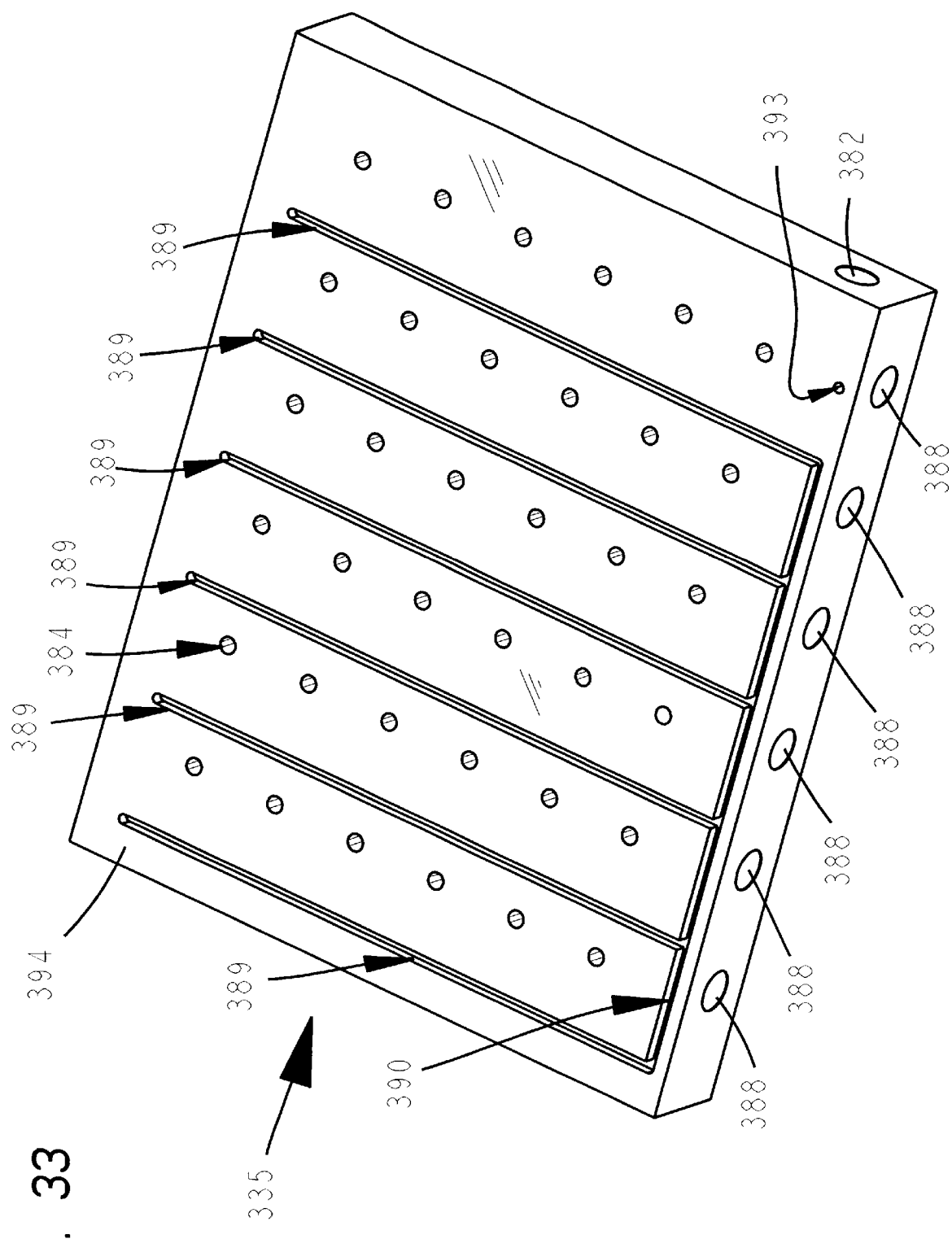
FIG. 33 is a bottom isometric view of the gas manifold depicted in FIG. 32.
Figure 34:
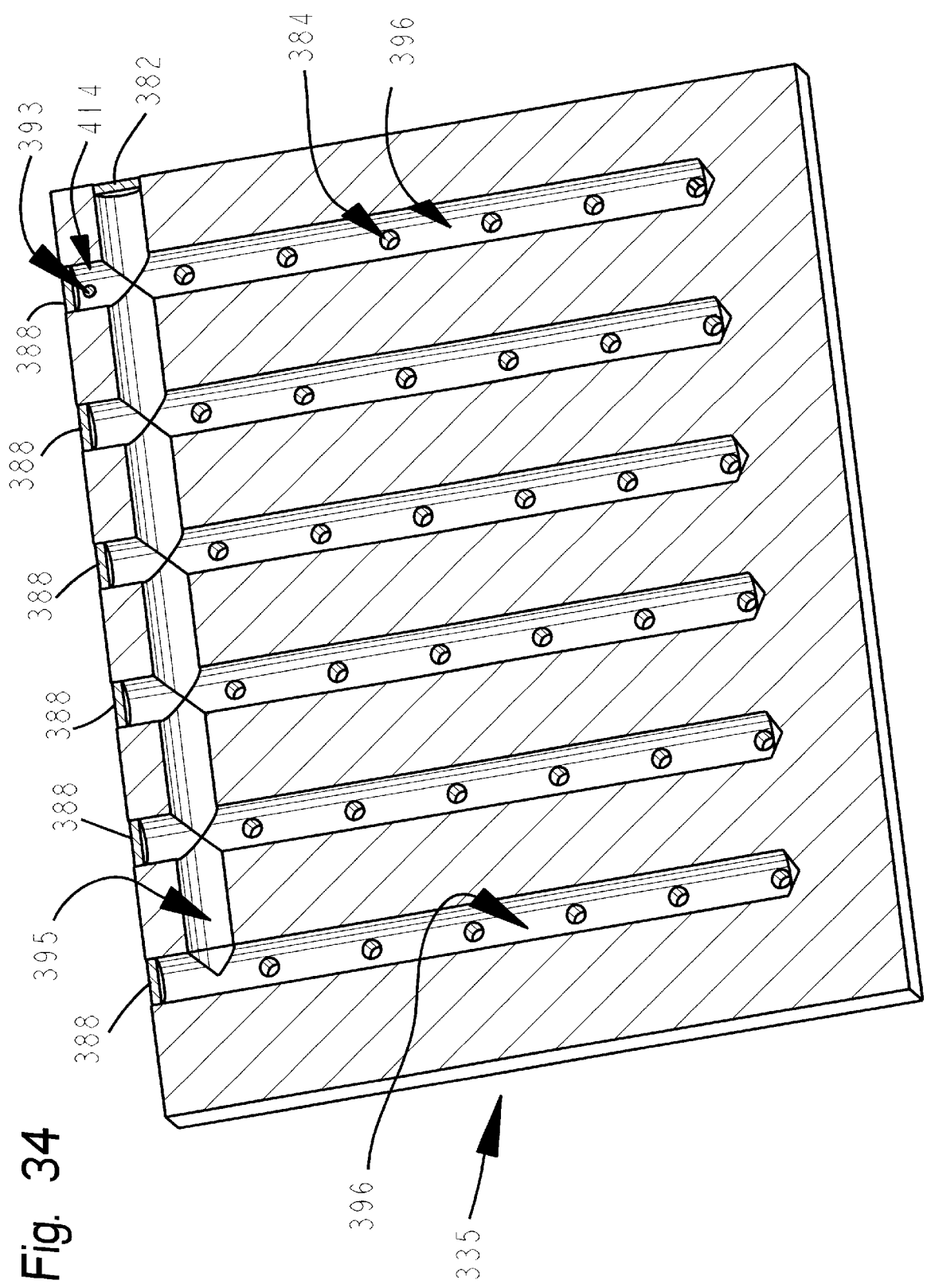
FIG. 34 is an isometric view with portions thereof removed of the gas manifold depicted in FIG. 32.

FIG. 27 shows an exploded view of the components that comprise constant temperature mixing and storage apparatus 342 of the second embodiment of the present invention. The components include, water bath assembly 332, lower gasket 333, disposable device 303, upper gasket 334, manifold 335, septum 336, top plate 339, clamp washers 340, and clamp knobs 341.

Referring to FIG. 22 FIG. 23, and FIG. 27 through FIG. 31 water bath assembly 332 contains water bath housing 411, one or more magnet drive shafts 344, one front bearing 352 and one rear bearing 351 for each magnet drive shaft 344, one pulley 348 for each magnet drive shaft 344, magnet drive motor 345, motor pulley 350, motor belt 346, magnet driveshaft belt 347 (when more than one magnet drive shafts 344 are used), bottom gasket 337, and bottom cover 338. To keep the magnet drive shafts 344, and thus permanent drive magnets 343 synchronized, magnet driveshaft belt 347 should be a timing belt, and pulleys 348 should be timing pulleys. The front bearing 352 and rear bearing 351 of magnet driveshaft 344 fit into bearing retainers (not shown), which are a part of water bath housing 411. Each magnet driveshaft 344 contains one or more permanent drive magnets 343. Permanent drive magnets 343 are preferably high energy rare earth magnets such as Neodymium 27 magnets, but can be any type of permanent magnet with a strong enough magnetic field to drive the follower magnets as described above, and as will be described below. The disposable device 303 shown in FIG. 27, and used to describe the second embodiment of the present invention contains an array of 36 wells 317, and the water bath assembly 332 shown in FIG. 28 contains two magnet drive shafts 344, with two permanent drive magnets 343 in each magnet driveshaft. However as described above, the disposable device 303 can contain one or more wells 317, and the water bath assembly can contain one or more magnet drive shafts 344, with one or more permanent drive magnets 343 per magnet driveshaft 344. The number of magnet drive shafts 344, and the number of permanent drive magnets 343 per magnet driveshaft will depend on the strength of the permanent drive magnets 343, and upon the number of wells in disposable device 303, and upon the layout of the wells 317 in disposable device 303 (i.e. the number of rows and columns). Water bath housing 411 contains well 359 which is divided into two parts, a lower part for containing a temperature controlled solution, said lower part defined by side wall 375, side wall 381, end wall 374, end wall 378, and bottom wall 373; and an upper part for aligning other components of constant temperature mixing and storage apparatus 342, said upper part defined by surface 362, side wall 380, side wall 412, end wall 379, and end wall 413. Side walls 380 and 412 contain cutouts 377 which facilitate the placement of other components into, and the removal of other components from the upper part of well 359. The width W411 of the upper part of well 359 should be slightly larger (i.e. about 0.020" larger) than the width W300 of well plate 300, and the length L411 of the upper part of well 359 should be slightly larger (i.e. about 0.020" larger) than the length L300 of well plate 300. The lower part of well 359 contains ribs 358 which protrude from bottom wall 373, constant temperature water drain holes 354, and constant temperature water feed holes 357. Outer wall 376 of water bath housing 411 contains constant temperature water inlet hole 356, and constant temperature outlet hole 353. Constant temperature water feed holes 357 extend through end wall 378 into constant temperature water inlet hole 356, and constant temperature water drain holes 354 extend through end wall 374 into constant temperature water outlet hole 353. Outer side wall 376 also contains mix gas inlet hole 364, which extends into outer wall 376. Port 363 extends from surface 362 into mix gas inlet hole 364. Outer wall 368 of water bath housing 411 contains storage gas inlet hole 419 which extends into outer wall 368, and valve gas inlet hole 360 which also extends into outer wall 368. Port 355 extends from surface 362 into valve gas inlet hole 360, and port 361 extends from surface 362 into storage gas inlet hole 419. Holes 367 contain clamp bolts 366. Water bath housing 411 should be made from a non magnetic material such as cast epoxy, plastic or anodized aluminum.

Referring to FIG. 21, FIG. 22, and FIG. 32 through FIG. 34, manifold 335 is rectangular in shape, with an overall length L335, equal to the overall length L300, of well plate 300, and with an overall width W335, equal to the overall width W300, of well plate 300. Manifold 335 contains blind holes 396, the outer ends of which are capped with plugs 388. The number of blind holes 396 in manifold 335, equals the number of columns of wells 317, in well plate 300. Manifold 335 also contains blind hole 395 the outer end of which is capped with plug 382. Blind hole 395 intersects blind holes 396, and acts as a feed hole for blind holes 396. Storage chamber feed holes 384 of manifold 335 extend from top surface 385 to bottom surface 394, and extend through the center of their corresponding blind hole 396. Storage gas feed hole 393 extends from bottom surface 394 of manifold 335, into the end segment 414 of the end blind hole 396. Bottom surface 394 of manifold 335 contains valve gas feed channel 390, and valve gas channels 389. The number of valve gas channels 389 in manifold 335 equals the number of columns of wells 317 in well plate 300. Manifold 335 should be made from a non-magnetic material such as non-magnetic stainless steel, hard coat anodized aluminum, or a plastic or epoxy material. Both the top and bottom surfaces of manifold 335 must be made flat and parallel to assure a uniform compression of the septum and gaskets used in constant temperature mixing and storage apparatus 342.

An alternate way to construct manifold 335 (not shown) would be to eliminate blind holes 396, blind hole 395, plugs 388, and plug 382. Storage chamber feed holes 384 could be connected in parallel on top surface 385 of manifold 335 using a series of channels similar to channels 314, 315, and 316 on the top surface of well plate 300.

Figure 35:
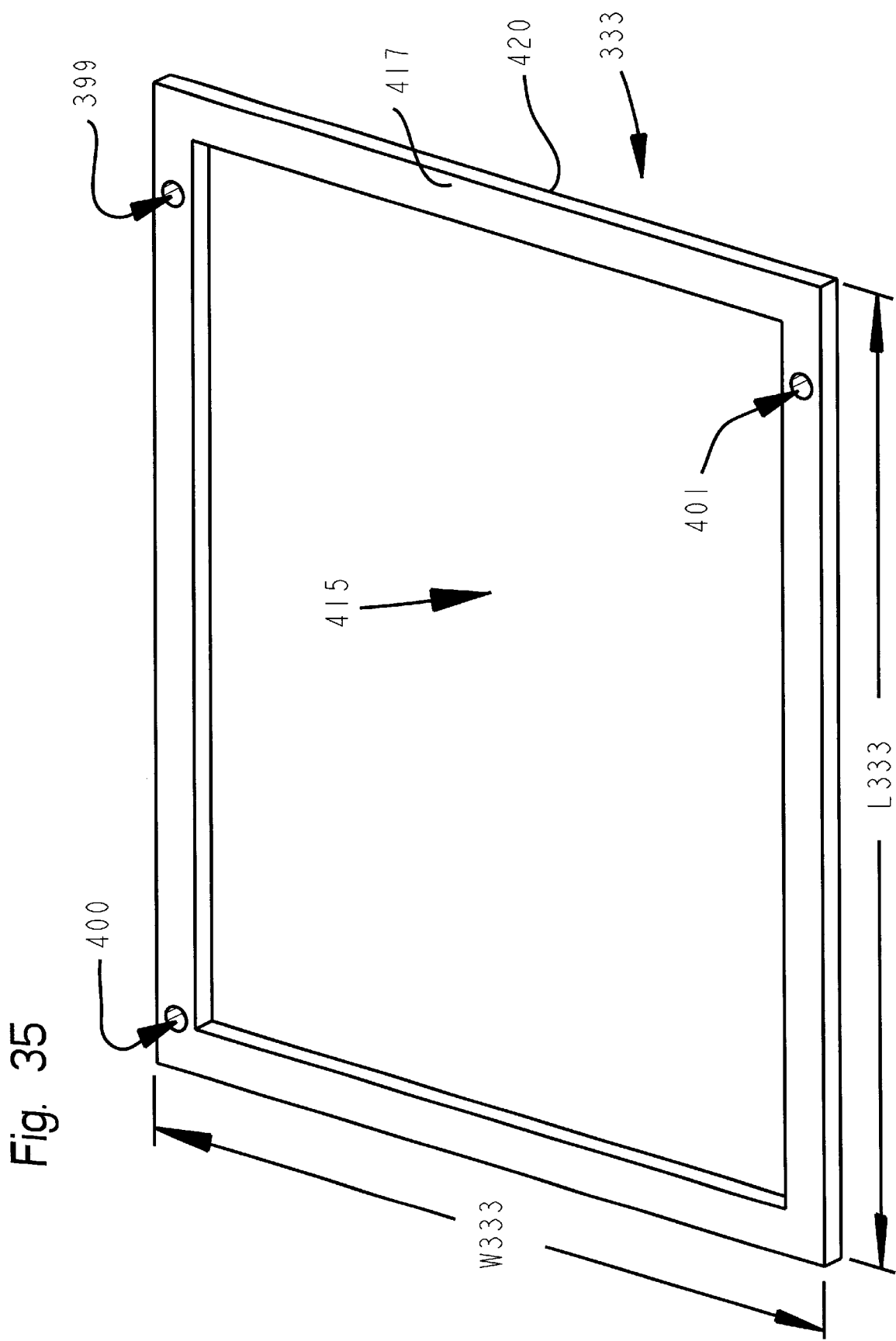
FIG. 35 is an isometric view of the well plate bottom gasket depicted in FIG. 27.

Referring to FIG. 22 and FIG. 35, lower gasket 333 is rectangular in shape, with an overall length L333, equal to the overall length L300, of well plate 300, and with an overall width W333, equal to the overall width W300, of well plate 300. Lower gasket 333 contains center rectangular hole 415, the dimensions of which equal the outside dimensions of the grid of stiffening ribs 308 on the bottom of well plate 300. Lower gasket 333 contains port 399, port 400, and port 401, all of which extend through the thickness of lower gasket 333. When top surface 417 of lower gasket 333 is in contact with bottom surface 416 of well plate 300, so that the grid of stiffening ribs 308 of well plate 300 fits inside of center hole 415 of lower gasket 333, port 399 of lower gasket 333 will align with storage gas port 306 of well plate 300, port 400 of lower gasket 333 will align with valve gas port 307 of well plate 300, and port 401 of lower gasket 333 will align with mix gas port 305 of well plate 300.

Figure 36:
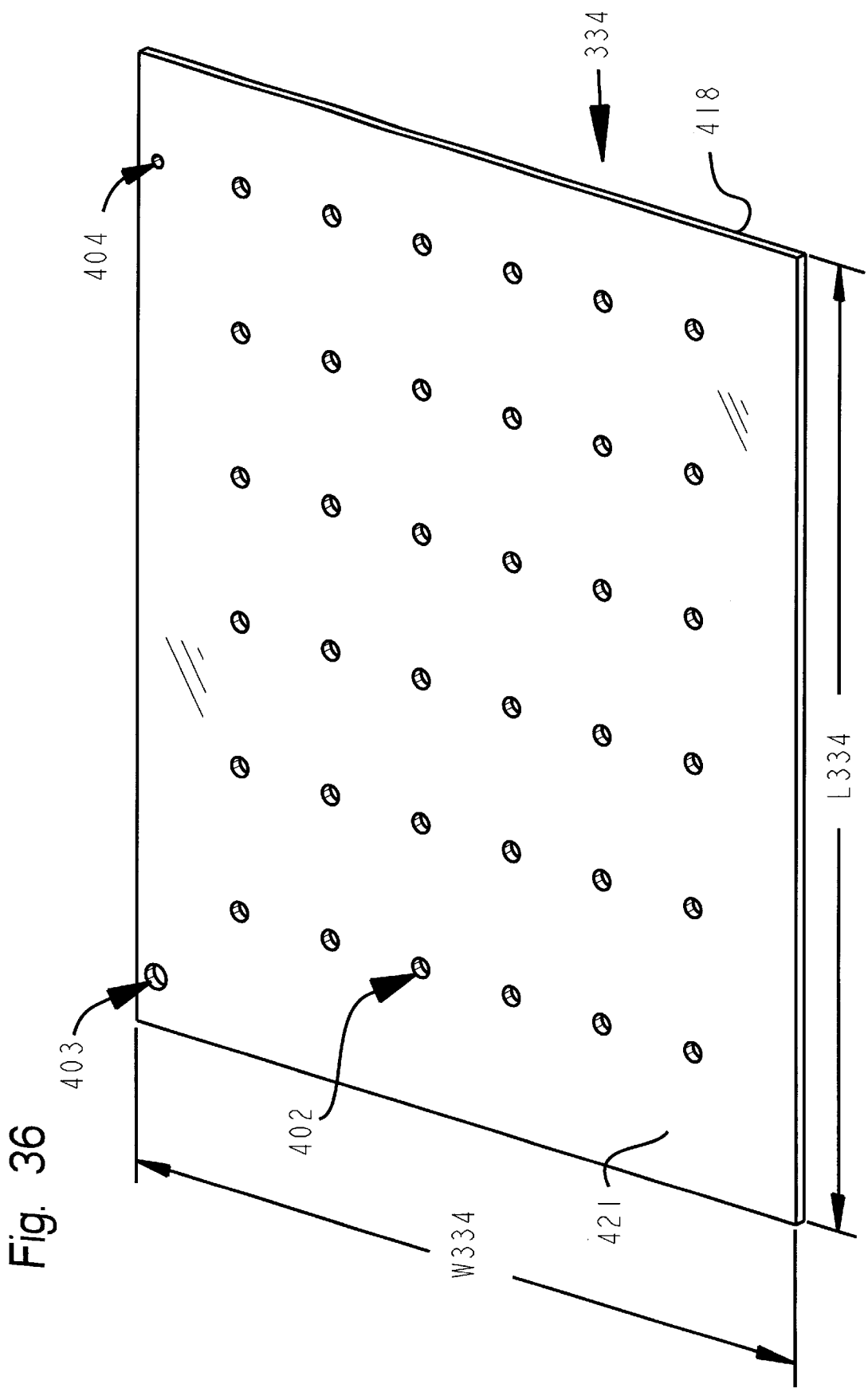
FIG. 36 is an isometric view of the well plate top gasket depicted in FIG. 27.
Figure 37:
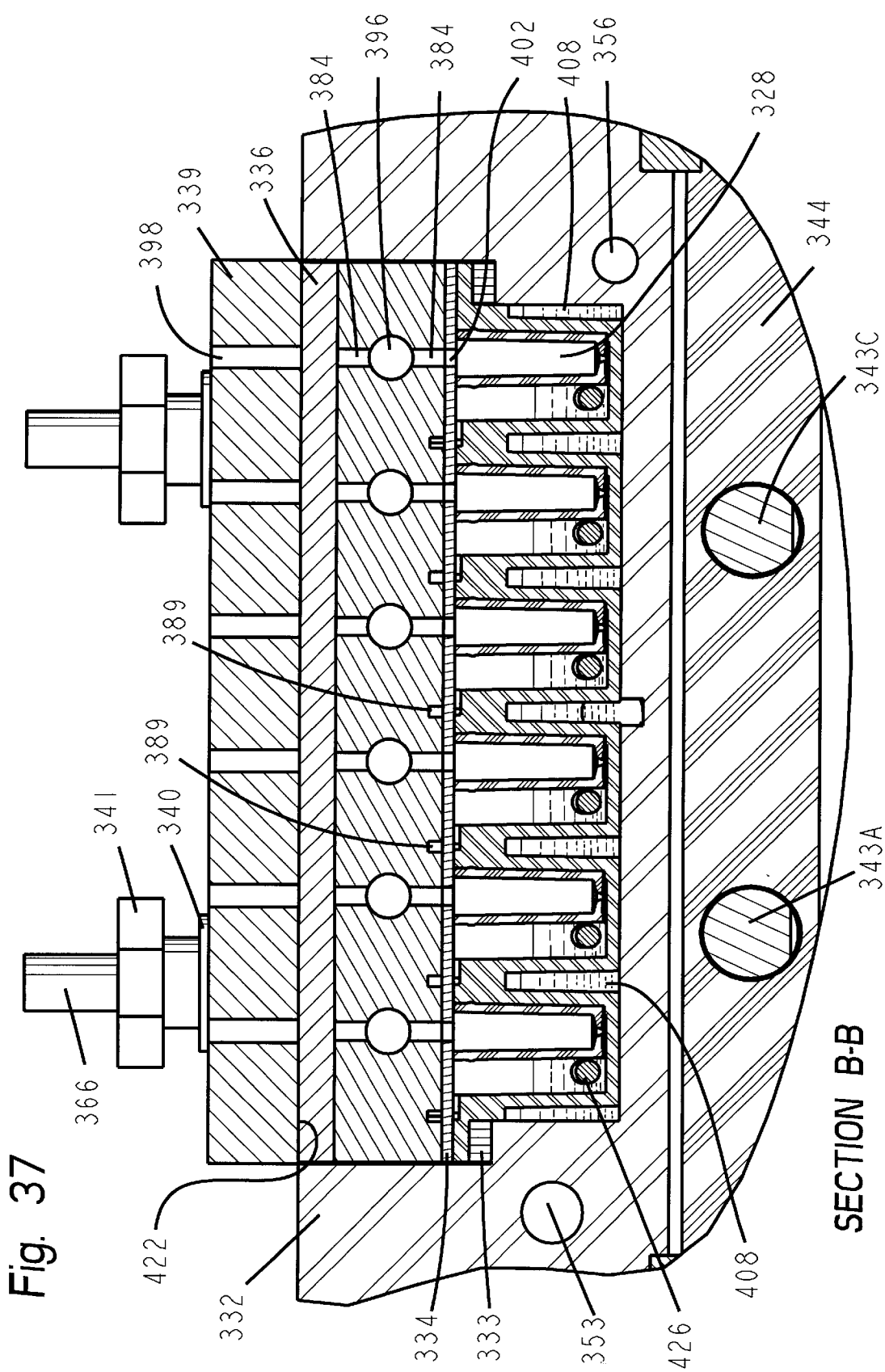
FIG. 37 is a partial cross-sectional view of the assembled components depicted in FIG. 27. The cross-section is taken through plane BB shown in FIG. 40.

Referring to FIG. 21, FIG. 22, and FIG. 36, upper gasket 334 is rectangular in shape, with an overall length L334, equal to the overall length L300, of well plate 300, and with an overall width W334, equal to the overall width W300, of well plate 300. Upper gasket 334 contains port 403, port 404, and an array of ports.402, all of which extend through the thickness of upper gasket 334. The number of ports 402 in upper gasket 334 is equal to the number of wells 317 in well plate 300. When bottom surface 418 of upper gasket 334 is in contact with top surface 304 of well plate 300, so that the outer edges of upper gasket 334 align with the outer edges of the top surface 304 of well plate 300, port 404 of upper gasket 334 will align with storage gas port 306 of well plate 300, port 403 of upper gasket 334 will align with valve gas port 307 of well plate 300, and ports 402 will align with the center of their respective storage chambers (i.e. the centers of cups 301) of disposable device 303.

Figure 39:
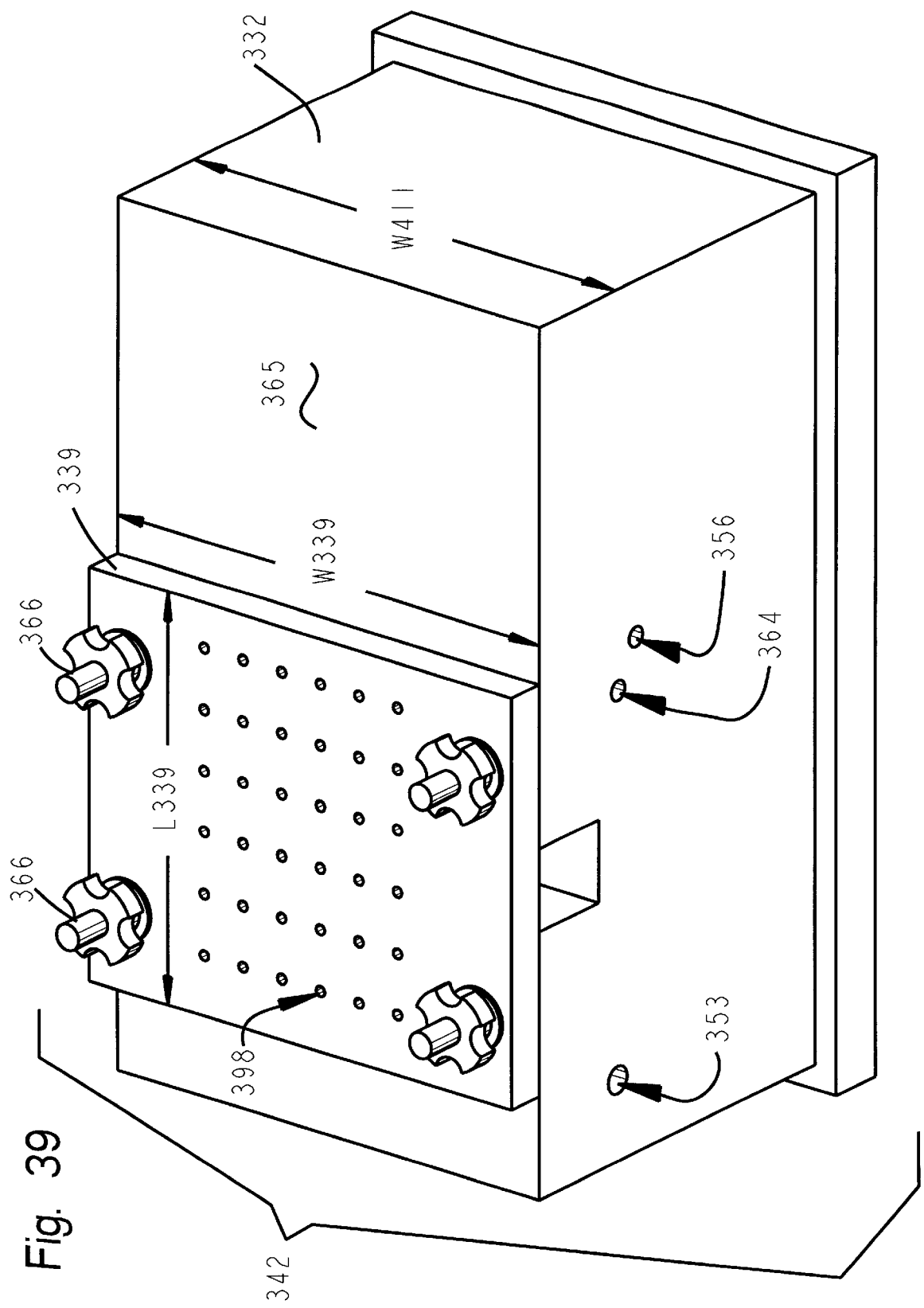
FIG. 39 is an isometric view of the components depicted in FIG. 27, in an assembled state.
Figure 40:
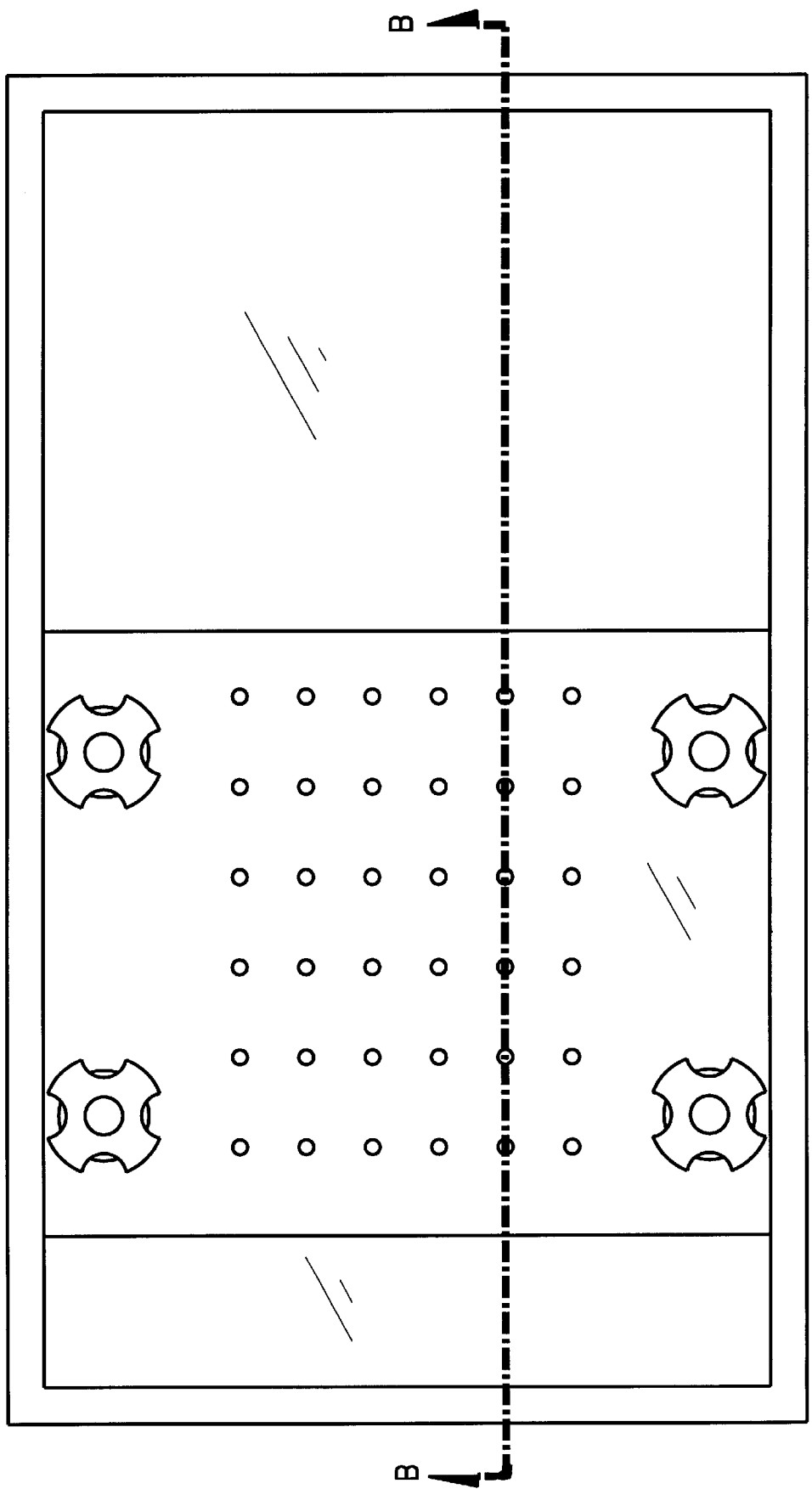
FIG. 40 is a top view of the assembly shown in FIG. 39, showing the cutting plane and direction of cross-section BB.

Referring to FIG. 22, FIG. 27, and FIG. 39, top plate 339 is rectangular in shape, with an overall length L339, equal to or greater than the overall length L300, of well plate 300, and with an overall width W339, equal to the overall width W411A of water bath housing 411. Top plate 339 contains an array of through holes 398, all of which extend through the thickness of top plate 339. The number of through holes 398 in top plate 339 is equal to the number of wells 317 in well plate 300. Top plate 339 also contains four clamp holes 386, that align with clamp bolts 366 of water bath assembly 332. When top plate 339 is located on water bath assembly 332, so that clamp bolts 366 protrude through clamp holes 386 of top plate 339, as shown in FIG. 39, and disposable device 303 is positioned in the upper part of well 359 of water bath housing 411 (as described below), through holes 398 of top plate 339 will align with the center of their respective storage chambers (i.e. the center of cups 301) in disposable device 303. Top plate 339 should be made from a non-magnetic material such as non-magnetic stainless steel, hard coat anodized aluminum, or a plastic or epoxy material. The top and bottom surfaces of top plate 339 should be made flat and parallel to assure a uniform compression of the septum and gaskets used in constant temperature mixing and storage apparatus 342.

In the following discussion of the operation of the constant temperature mixing and storage apparatus 342, the means (i.e. manual or automatic valve means) by which a temperature controlled solution (said solution may be temperature controlled water) is applied to constant temperature water inlet hole 356, or the means by which gas is applied to mix gas inlet hole 364, storage gas inlet hole 419, or valve gas inlet hole 360, (all of said ports being of water bath assembly 332), will not be discussed.

Referring to FIG. 27, constant temperature mixing and storage apparatus 342 contains a disposable device 303, and a reusable instrument comprised of water bath assembly 332, manifold 335, top plate 339, clamp washers 340, clamp knobs 341, and any associated valves. Lower gasket 333, and upper gasket 334 may be used more than once, and are semi-disposable. Septum 336 should be replaced with each new disposable device 303.

Referring to FIG. 21, FIG. 22, FIG. 27, FIG. 30, FIG. 31, FIG. 32, FIG. 33, and to FIG. 35 through FIG. 40, the constant temperature mixing and storage apparatus 342 is assembled by the user for use as follows. The water bath assembly 332 will have a source of constant temperature water connected to constant temperature water inlet hole 356 through a valve (not shown), a drain line will be connected to constant temperature water outlet hole 353, a gas source (compressed air, or compressed nitrogen, or any other pressurized gas source the user chooses) and a venting means will be connected through either manual or automatic valves (not shown), to mix gas inlet hole 364, storage gas inlet hole 419, and valve gas inlet hole 360. The user will purchase the disposable device 303 assembled. To use the constant temperature mixing and storage apparatus 342 for solubility testing the user will place a quantity of compound to be tested for solubility into each mix chamber 405 of disposable device 303. Each mix chamber 405 may contain a different type of compound. The user then will place a lower gasket 333 into the upper part of well 359 of water bath housing 411, of water bath assembly 332 with bottom surface 420 of lower gasket 333 resting on surface 362 of water bath housing 411, with port 400 of lower gasket aligning with port 355 of water bath housing 411, with port 399 of lower gasket 333 aligned with port 361 of water bath housing 411, and with port 401 of lower gasket 333 aligned with port 363 of water bath housing 411. The user then places disposable device 303 into the upper part of well 359 of water bath housing 411 with bottom surface 416 of flange 409 of disposable device 303 resting on top surface 417 of lower gasket 333, with mix gas port 305 of disposable device 303 aligned with port 401 of lower gasket 333, with storage gas port 306 of disposable device 303 aligned with port 399 of lower gasket 333, and with valve gas port 307 of disposable device 303 aligned with port 400 of lower gasket 333. The user then places upper gasket 334 into the upper part of well 359 of water bath housing 411 with bottom surface 418 of upper gasket 334 resting on top surface 304 of disposable device 303, with port 403 of upper gasket 334 aligned with valve gas port 307 of disposable device 303, and with port 404 of storage gas port 306 of disposable device 303. This alignment of upper gasket 334 will align the array of ports 402 of upper gasket 334, so that each port 402 will be aligned over the center of its corresponding storage chamber 328, of disposable device 303. Next the user will place manifold 335 into the upper part of well 359 of water bath housing 411 with bottom surface 394 of manifold 335 resting on top surface 421 of upper gasket 334, with storage gas feed hole 393 of manifold 335 aligned with port 404 of upper gasket 334, and with valve gas feed channel 390 of manifold 335 aligned over port 403 of upper gasket 334. This alignment of manifold 335 aligns storage chamber feed holes 384 of manifold 335 with their corresponding port 402 of upper gasket 334, and aligns valve gas channels 389 over gas channels 315 of disposable device 303. Next the user places septum 336 into the upper part of well 359 of water bath housing 411 so that either face of septum 336 rests on top surface 385 of manifold 335, and so that the outer edges of septum 336 align with the outer edges of manifold 335. The user then places top plate 339 onto water bath assembly 332 with clamp bolts 366 of water bath assembly 332 protruding through clamp holes 386 of top plate 339, and with top plate 339 resting on top of septum 336. The array of through holes 398 in top plate 339 is symmetrical, hence either face of top plate 339 may face down. Through holes 398 of top plate 339 will now be aligned over the center of their corresponding storage chambers of disposable device 303. Next the user places one washer 340 onto each clamp bolt 366, and then screws a clamp knob 341 onto each clamp bolt 366, uniformly tightening the clamp knobs 341 until the bottom surface of top plate 339 is flush with top surface 365 of water bath assembly 332. The constant temperature mixing and storage apparatus 342 is now assembled and ready for use.

Referring to FIG. 21, FIG. 22, FIG. 27, FIG. 28, FIG. 29, FIG. 35, FIG. 37, and FIG. 38, with the constant temperature mixing and storage apparatus 342 in the assembled state as described above, bottom surface 416 of flange of flange 409, of disposable device 303, is sealed to top surface 417 of lower gasket 333; and bottom surface 420 of lower gasket 333 is sealed to surface 362, of well 359, of water bath assembly 332. Therefore, the lower part of well 359 of water bath assembly 332 becomes a sealed chamber, capped by bottom surface 416 of disposable device 303, and with outer side wall 387, and outer bottom walls 410 of wells 317 of disposable device 303 sealed within this chamber, and with outer bottom walls 410 in contact with ribs 358 of the lower part of well 359 of water bath assembly 332. Once constant temperature mixing and storage apparatus 342 is in the assembled state, the user will make sure that the valve (not shown, and used to drain the lower part of well 359) connected to drain hole 427 of water bath assembly 332 is closed, and then apply a pressurized temperature controlled solution (preferably water) to constant temperature water inlet hole 356 of water bath assembly 332. The temperature controlled solution will flow through constant temperature water inlet hole 356 of water bath assembly 332, exiting through the parallel constant temperature water feed holes 357 of water bath assembly 332, into the sealed lower part of well 359, flowing around the outer side wall 387 and outer bottom walls 410 of disposable device 303, then through parallel constant temperature water drain holes 354 of water bath assembly 332, through constant temperature water outlet hole 353 of water bath assembly 332, back to the source of the temperature controlled solution. The re-circulating temperature controlled solution will keep the outer side wall 387 and outer bottom walls 410 of wells 317 of disposable device 303 at a constant temperature, and therefore also keep the mix chamber 405 and storage chamber 328, and their contents at a constant temperature. Because the wall thickness of well plate 300 and cups 301 of disposable device 303 can be molded thin (i.e. with a thickness of between 0.035" and 0.1"), the thermal response time (i.e. the time required to bring the contents of the mix chamber and storage chamber to the regulated temperature) will be short. The flow of temperature controlled solution through the lower part of well 359 will be maintained throughout the process.

Referring to FIG. 21, FIG. 22, FIG. 23, FIG. 27, FIG. 29, FIG. 32, FIG. 33, FIG. 34, FIG. 35, FIG. 36, FIG. 37, and FIG. 38, with constant temperature mixing and storage apparatus 342 in the assembled state, top surface 304 of wall plate 300 will be sealed to bottom surface 418 of upper gasket 334; top surface 421 of upper gasket 334 will be sealed to bottom surface 394 of manifold 335; top surface 385 of manifold 335 will be sealed to bottom surface 423 of septum 336; and U top surface 424 of septum 336 will be sealed to bottom surface 422 of top plate 339. Therefore, with the previously discussed port alignments, there will be a gas flow path through valve gas inlet hole 360 of water bath assembly 332, through port 355 of water bath assembly 332, through port 400 of lower gasket 333, through valve gas port 307 of disposable device 303, through port 403 of upper gasket 334, through valve gas feed channel 390 of manifold 335, into valve gas channels 389 of manifold 335. Hence valve gas channels 389 of manifold 335 will be in gas flow communication with valve gas inlet 360 of water bath assembly 332. There will also be a flow path through storage gas inlet hole 419 of water bath assembly 332, through port 361 of water bath assembly 332, through port 399 of lower gasket 333, through storage gas port 306 of disposable device 303, through port 404 of upper gasket 334, through storage gas feed hole 393 of manifold 335, through end segment 414 of the end blind hole 396 of manifold 335, through blind hole 395 of manifold 335, through blind holes 396 of manifold 335 (all of which are connected in parallel by blind hole 395), through storage chamber feed holes 384 of manifold 335 (all of which are connected in parallel by blind hole 395 and blind holes 396), into storage chambers 328 of disposable device 303. Hence storage gas inlet hole 419 of water bath assembly 332 is in gas flow communication with all of the storage chambers 328 of disposable device 303. There is a third flow path through mix gas inlet hole 364 of water bath assembly 332, through port 363 of water bath assembly 332, through port 401 of lower gasket 333, through mix gas port 305 of disposable device 303, through mix gas link channel 425 of disposable device 303, through main gas channel 314 of disposable device 303, through gas channels 315 (all of which are connected in parallel by main gas channel 314) of disposable device 303, through well gas channels 316 of disposable device 303 (all of which are connected in parallel by gas channels 315 and main gas channel 314), into the mix chambers 405 of disposable device 303 (all of which are connected in parallel by well gas channels 316, gas channels 315, and main gas channel 314). Hence mix gas inlet hole 364 of water bath assembly 332 is in gas flow communication with the mix chambers 405 of disposable device 303. As described above, valve gas channels 389 of manifold 335 will be aligned over gas channels 315 of disposable device 303. Hence, if mix gas inlet hole 364 of water bath assembly 332 is vented to atmosphere, or a low gas pressure is applied to mix gas inlet hole 364, and if a higher gas pressure is applied to valve gas inlet 360 of water bath assembly 332, the higher gas pressure will also be applied to valve gas channels 389 of manifold 335, said higher gas pressure in valve gas channels 389 of manifold 335 will deform the portions of upper gasket 334 below valve gas channels 389 of manifold 335 into gas channels 315 of disposable device 303, thus closing gas channels 315 of disposable device 303, and isolating the mix chambers 405 of disposable device 303 from each other, and from mix gas inlet hole 364. This will prevent evaporation of solution in mix chambers 405. Alternately the entire flow path between valve gas inlet hole 360 of water bath assembly 332 and valve gas channels 389 of manifold 335 may be eliminated, and evaporation from mix chambers 405 can be minimized by making well gas channels 316 of disposable device 303 very small in cross-section. For example well gas channels could be made as small as 0.010" wide X 0.010" high. In this case the Durometer of upper gasket 334 should be high enough so that upper gasket 334 does not extrude into well gas channels 316 when upper gasket 334 is in the compressed state.

Referring to FIG. 23, FIG. 25, FIG. 27, FIG. 28, FIG. 37, FIG. 38, FIG. 39, and FIG. 40, with the constant temperature mixing and storage apparatus 342 in the assembled state, with a sample of compound (i.e. solute) to be tested in each mix chamber 405 of disposable device 303, as described above, the user will proceed as follows to test the samples of compound for solubility. To purge the mix chambers 405, and storage chambers 328 of disposable device 303, and the mix gas flow path, and storage gas flow path as described above with dry nitrogen (or any other gas), the user will apply pressurized gas (such as dry nitrogen or air) to mix gas inlet hole 364 of water bath assembly 332, and vent storage gas inlet hole 419 of water bath assembly 332. Valve gas inlet hole 360 of water bath assembly 332 should also be vented. Once the flow paths are purged, the user will either reduce the gas pressure applied to the mix gas inlet hole 364 to a very low value (i.e. below 1 p.s.i.) or shut off the source of pressurized gas to the mix gas inlet hole 364, leaving the storage gas inlet hole 419 vented. A quantity of solvent (i.e. 40 μl or greater) is then added to each storage chamber by inserting a needle through each hole 398 of top plate 339, through septum 336 (by piercing septum 336), through the corresponding storage chamber feed hole 384 of manifold 335, through the corresponding port 402 of upper gasket 334 into storage chamber 328. The needle (not shown) that delivers the solvent can either be connected to a manual syringe, or to an automated dispensing apparatus. After adding the solvent to the storage chamber, the needle is withdrawn, resealing the septum (i.e. the septum is made from a self sealing material such as Teflon coated gum rubber). Pressurized gas is now applied to storage gas inlet hole 419 of water bath assembly 332, mix gas inlet hole 364 and valve gas inlet hole 360 of water bath assembly 332 are both vented. Therefore the storage chambers 328 of disposable device 303 become pressurized, thus forcing the solvent through port 329 of disposable device 303, into circular grooves 322 and 325 of disposable device 303, through filter element 302, into chamber 309 of disposable device 303, through slot 310 of disposable device 303, into mix chamber 405 of disposable device 303. As the solvent passes through filter element 302, the filter element will become wetted with the solvent, therefore, the applied gas pressure should be less than the bubble point pressure of the filter, for the solvent being used, to prevent the pressurized gas in storage chamber 328 from passing through filter element 302. Once the solvent has been forced from storage chambers 328, into mix chambers 405, pressurized gas is applied to valve gas inlet hole 360 of water bath assembly 332, thus closing gas channels 315 of disposable device 303, as described above, thus isolating mix chambers 405, and thus preventing evaporation from mix chambers 405. The magnet drive motor 345 of water bath assembly 332 is now turned on, causing the one or more magnet drive shafts 344 of water bath assembly 332 to rotate synchronously in the same direction, thus causing the one or more permanent drive magnets 343 of the magnet drive shafts 344 to rotate about a driver axis coincident with the central axis of their corresponding magnet drive shaft 344. The rotating permanent drive magnets 343 cause the follower magnets 426 in mix chambers 405 of disposable device 303 to rotate with a tumbling motion about a follower axis parallel to the central axis of said magnet drive shafts, as previously described. The tumbling rotation of the follower magnets in the mix chambers causes the solvent to rapidly mix with the solute in the mix chambers to form a solution. After a predetermined time interval, the user will stop the magnet drive motor 345 of water bath assembly 382 thus stopping the rotation of the permanent drive magnets 343, thus stopping the rotation of the follower magnets 426 in mix chambers 405 of disposable device 303 (optionally the user may choose not to turn the motor off at this point). The user will then vent valve gas inlet hole 360 of water bath assembly 332, vent storage gas inlet hole of water bath assembly 332 and apply pressurized gas (with a pressure less than the bubble point pressure for the solvent being used) to mix gas inlet hole 364 of water bath assembly 332. Hence, pressurized gas will be applied to the mix chambers 405 of disposable device 303, and storage chambers 328 of disposable device 303 will be vented, said pressurized gas in mix chambers 405 will force the solution from mix chamber 405, through slot 310 of disposable device 303, into chamber 309 of disposable device 303, through filter element 302, into circular grooves 322 and 325 of disposable device 303, through port 329 of disposable device 303, into storage chamber 328 of disposable device 303. By making the pore size of filter element 302 smaller than the minimum particle size of the solute, the excess solute in mix chamber 405 will remain in chamber 405, since it can not pass through the filter element. The user will then insert a needle through hole 398 of top plate 339, through septum 336 (by piercing septum 336), through the corresponding storage chamber feed hole 384 of manifold 335, through the corresponding port 402 of upper gasket 334 into the corresponding storage chamber 328. The needle (not shown) can be connected to a manual syringe, or to an automated aspirating apparatus. A sample of solution will be withdrawn from the storage chamber 328 into the needle. The needle with solution sample is then withdrawn, resealing the septum (i.e. the septum is made from a self sealing material such as Teflon coated gum rubber). The sample is then transferred from the needle to a storage vial, or to an instrument known in the art, for solubility analysis of the sample. The process is then reversed, forcing the remaining solution from the storage chamber, through the filter element, into the mix chamber, where it is again mixed with the remaining solute, as described above. After a second mixing time period (determined by the user), the solution less excess solute is again forced from the mix chamber, through the filter element, into the storage chamber, where a second sample is taken for analysis as described above. This process is continued until the required number of samples (determined by the user) are taken, or until all of the solution has been removed for testing. It should be noted that the operation takes place with the constant temperature mixing and storage apparatus 342 resting stationary on a work bench, as opposed to the use of a vortex stirrer which would move the apparatus in a orbital motion, and which would provide less efficient mixing, which would in turn require a longer time period to obtain complete mixing of the solvent and solute.

Once the process is complete, mix gas inlet hole 364, storage gas inlet hole 419, and valve gas inlet hole 360, of water bath assembly 332 are vented, the source of temperature controlled solution applied to constant temperature water inlet hole 356 of water bath assembly 332 is turned off, and the lower part of well 359 of water bath assembly 332 can be drained of temperature controlled solution, by opening a drain valve (not shown) connected to drain hole 427 of water bath assembly 332. The clamp knobs 341 of constant temperature mixing and storage apparatus 342 are then unscrewed, and the components of the constant temperature mixing and storage apparatus 342 (i.e. top plate 339, septum 336, manifold 335, upper gasket 334, disposable device 303, and lower gasket 333) are removed from the water bath assembly 332. The mix chambers 405 of disposable device 303 can then be inspected to make sure that some solute remains in each mix chamber. If any of the mix chambers 405 are void of excess solute, the user can either add more solute to those mix chambers, and then re-assemble the constant temperature mixing and storage apparatus 342, and continue the process with the remaining solution in the storage chambers; or the user can run the test over again with a new disposable device, this time adding more solute to the mix well.

With the process just described, the user can quickly, and easily check many compounds for solubility using a single disposable device. The tests are run at a constant temperature, in an inert atmosphere; and the solution in each mix chamber is mixed rapidly, using individual mix chamber magnets, while the constant temperature mixing and storage apparatus rests stationary on the bench top.

Referring to FIG. 23, FIG. 25, FIG. 27, FIG. 28, FIG. 37, FIG. 38, FIG. 39, and FIG. 40, constant temperature mixing and storage apparatus 342 can be used as a multi-well reaction block to synthesize compounds using solid phase chemistry. To use the constant temperature mixing and storage apparatus 342 for this purpose the user starts by adding a quantity of resin 406 (the amount and type of resin to be determined by the user) to each mix chamber 405 of a new disposable device 303. A follower magnet 426 is then added to each mix chamber. The components of the constant temperature mixing and storage apparatus 342 (i.e. lower gasket 333, disposable device 303, upper gasket 334, manifold 335, septum 336, top plate 339, clamp washers 340, and clamp knobs 341) are then assembled to water bath assembly 332, as described above. The user then applies a source of temperature controlled solution to constant temperature water inlet hole 356 of water bath assembly 332, as described above, to regulate the temperature of the mix chambers 405, and storage chambers 328, of disposable device 303 as described above. The gas flow paths are then purged with an inert gas (chosen by the user) by applying pressurized inert gas, to mix gas inlet hole 364 of water bath assembly 332; and by venting storage gas inlet hole 419 and valve gas inlet hole 360, both of water bath assembly 332, as described above. A quantity of solution (the type and amount of solution to be determined by the user) is then added to each storage chamber by inserting a needle through hole 398 of top plate 339, through septum 336 (by piercing septum 336), through corresponding storage chamber feed hole 384 of manifold 335, through corresponding port 402 of upper gasket 334 into corresponding storage chamber 328. The needle (not shown) that delivers the solution can either be connected to a manual syringe, or to an automated dispensing apparatus. After adding the solution to the storage chamber, the needle is withdrawn, resealing the septum (i.e. the septum is made from a self sealing material such as Teflon coated gum rubber). Pressurized inert gas is now applied to storage gas inlet hole 419 of water bath assembly 332, while mix gas inlet hole 364 and valve gas inlet hole 360 of water bath assembly 332 are vented. Therefore, the storage chambers 328 of disposable device 303 become pressurized, thus forcing the solution through port 329 of disposable device 303, into circular grooves 322 and 325 of disposable device 303, through filter element 302 of disposable device 303, into chamber 309 of disposable device 303, through slot 310 of disposable device 303, into mix chamber 405 of disposable device 303. As the solution passes through filter element 302, the filter element will become wetted with the solution, therefore, the applied gas pressure should be less than the bubble point pressure of the filter for the solution being used. Once the solution has been forced from storage chambers 328, into mix chambers 405, the user may or may not apply pressurized gas to valve gas inlet hole 360 of water bath assembly 332, to close gas channels 315 of disposable device 303, as described above, thus isolating mix chambers 405, and thus preventing evaporation from the mix chambers. The magnet drive motor 345 of water bath assembly 332 is now turned on, causing the one or more magnet drive shafts 344 of water bath assembly 332 to rotate synchronously in the same direction, thus causing the one or more permanent drive magnets 343 of the magnet drive shafts 344 to rotate about the central axis of their corresponding magnet drive shaft 344. The rotating permanent drive magnets 343 cause the follower magnets 426 in mix chambers 405 of disposable device 303 to rotate with a tumbling motion about an axis parallel to the central axis of said magnet drive shafts, as previously described. The tumbling rotation of the follower magnets in the mix chambers causes the solution to rapidly mix with the resin in the mix chambers. After a predetermined time interval, the user will stop the magnet drive motor 345 of water bath assembly 332, thus stopping the rotation of the permanent drive magnets 343, thus stopping the rotation of the follower magnets 426 in mix chambers 405 of disposable device 303. The user will then vent valve gas inlet hole 360 of water bath assembly 332, vent storage gas inlet hole 419 of water bath assembly 332, and apply pressurized inert gas (with a pressure less than the bubble point pressure for the solution being used) to mix gas inlet hole 364 of water bath assembly 332. Hence, pressurized inert gas will be applied to the mix chambers 405 of disposable device 303, and storage chambers 328 of disposable device 303 will be vented, said pressurized inert gas in mix chambers 405 will force the solution from mix chamber 405, through slot 310 of disposable device 303, into chamber 309 of disposable device 303, through filter element 302 of disposable device 303, into circular grooves 322 and 325 of disposable device 303, through port 329 of disposable device 303, into storage chamber 328 of disposable device 303. By making the pore size of filter element 302 smaller than the particle size of the resin, the resin in mix chamber 405 will remain in chamber 405, since it can not pass through the filter element. The user will then insert a needle through hole 398 of top plate 339, through septum 336 (by piercing septum 336), through corresponding storage chamber feed hole 384 of manifold 335, through corresponding port 402 of upper gasket 334, into corresponding storage chamber 328. The needle (not shown) can be connected to a manual syringe, or to an automated aspirating apparatus. The solution will be withdrawn from the storage chamber 328 into the needle. The needle with solution is then withdrawn, resealing the septum (i.e. the septum is made from a self sealing material such as Teflon coated gum rubber). The solution is discarded in an appropriate manner. The process just described will be repeated with rinse solutions, and additional reaction solutions, until the desired compound is obtained on the resin. The process will then be repeated once more with a cleavage solution. When this solution is withdrawn from the storage chamber it will be saved and further processed (by for example, evaporating the solvent to obtain the solute) by the user to obtain the final product. It should be noted that the operation takes place with the constant temperature mixing and storage apparatus 342 resting stationary on a work bench, as opposed to the use of a vortex stirrer which would move the apparatus in a orbital motion, and which would provide less efficient mixing, which would in turn require a longer time period to obtain complete mixing of the solvent and resin. It should also be noted that temperature of the mix chambers and storage chambers are controlled throughout the entire process.

Figure 41:
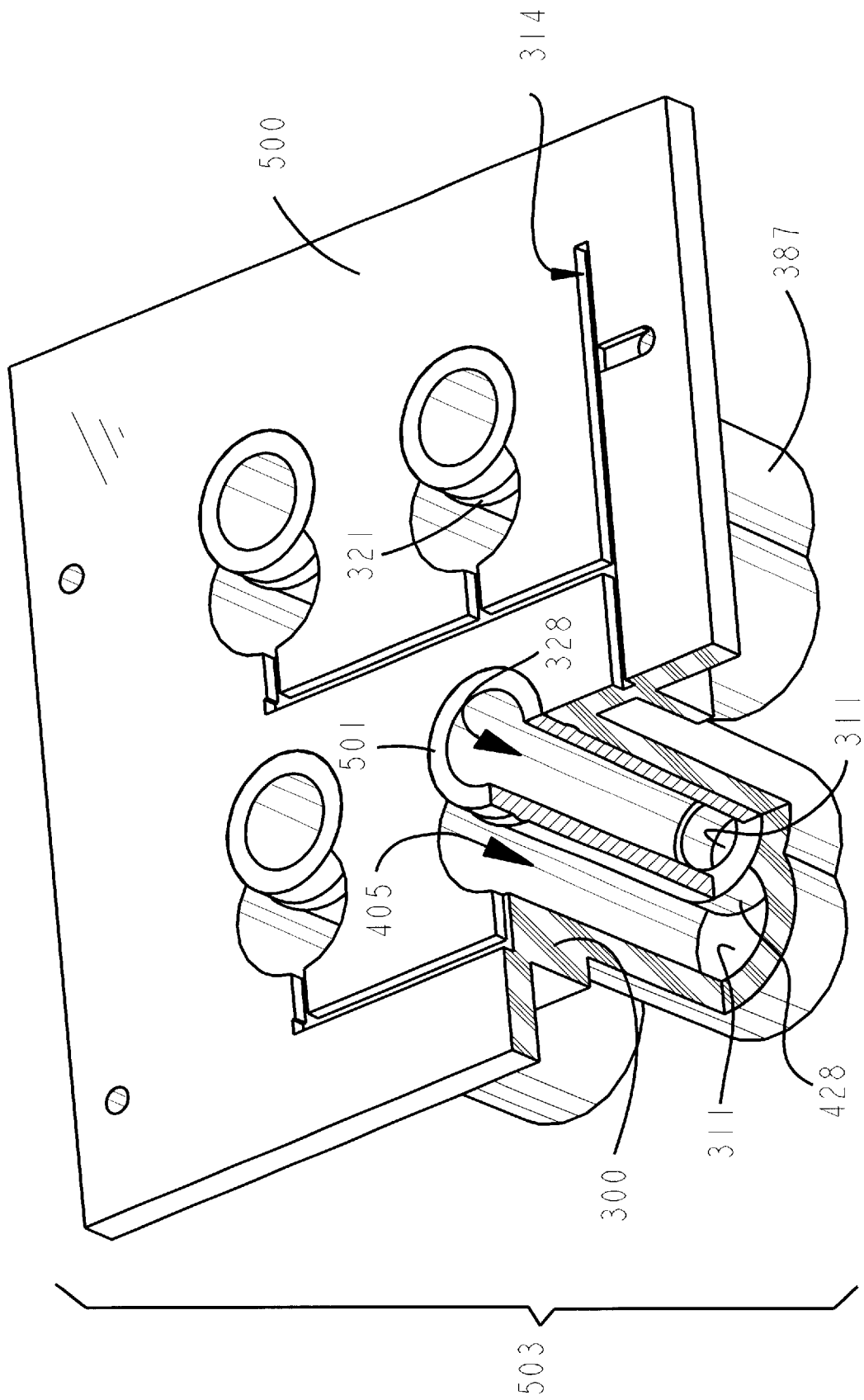
FIG. 41 is an isometric view with portions thereof removed of a multi-well plate of a third embodiment of the present invention.

A second embodiment of disposable device 303 is shown in FIG. 41 as disposable device 503. In this embodiment bottom wall 330, port 329, and filter support ribs 324 and 327 (shown in FIG. 25 and FIG. 26) of cup 301, are eliminated, and cup 301 is replaced with cup 501. Cup 501 has a through interior hole, as shown in FIG. 41. Filter element 302 (shown in FIG. 38) is replaced with a toroidal shaped filter frit 428, shown in FIG. 41. The toroid being formed by rotating a rectangle about the central axis of said toroid, so that the toroid has a flat top surface and flat bottom surface, and the inside and outside walls are cylindrical in shape, as shown in FIG. 41. Well plate 300 is replaced with well plate 500. Well plate 500 is the same as well plate 300 except that filter support rib 312 and filter support ribs 313, 312 and 313, which protrude from bottom wall 311 of well 317 (shown in FIG. 23). The bottom surface 311 of well 317 of well plate 500 is flat and does not contain any filter support protrusions as shown in FIG. 41. The top and bottom surfaces of toroidal filter frit 428 are compressed between bottom wall 311 of well 317 of well plate 500, and the bottom surface of cup 501, providing a leak tight seal, as shown in FIG. 41. Ring 321 of cup 501, snaps into groove 320 of well 317 of well plate 500, as described above, thus securing cup 501 to well plate 500. Because the components of disposable device 503 (i.e. well plate 500, cup 501, and filter frit 428) of this embodiment, are assembled using a snap fit between ring 321 of cup 501, and groove 320 of well 317 of well plate 500, and no glue bonds, solvent bonds, ultrasonic bonds, heat bonds, or any other kind of bond is needed to assemble this embodiment of disposable device 503, the components can easily be made of chemically resistant materials such as Teflon, polypropylene, or polyethylene, which are difficult to bond.

Disposable device 503 shown in FIG. 41, is assembled into constant temperature mixing and storage apparatus 342, as described above. However, because the toroidal filter frit is sealed between the bottom of cup 501, and bottom wall 311 of well 317, all of the resin in mix chamber 405 will remain in chamber 405, and will be easy to recover, if desired, when the process is complete, and constant temperature mixing and storage apparatus 342 is disassembled. In the previous embodiment, some of the resin may get trapped in chamber 309 (see FIG. 23) of disposable device 303, and this quantity will be difficult to recover. When the disposable device 503 shown in FIG. 41, is used in constant temperature mixing and storage apparatus 342, solution will flow from storage chamber 328, through filter frit 428, into mix chamber 405, or vise versa. Otherwise constant temperature mixing and storage apparatus 342 operates with disposable device 503 shown in FIG. 41, the same as it would with disposable device 303, shown in FIG. 21. The advantage of the disposable device 503 shown in FIG. 41, is that it is easier to assemble, and it can be fabricated from materials that are difficult to bond together. In the embodiment shown in FIG. 41, toroidal filter frit 428 could be replaced with cylindrical filter frit 433 shown in FIG. 42, or it could be replaced with a filter element 302 (shown in FIG. 21), sealed to the bottom of cup 501, in which case a gap should exist between the bottom surface of the filter element and bottom wall 311 of well 317.

Figure 42:
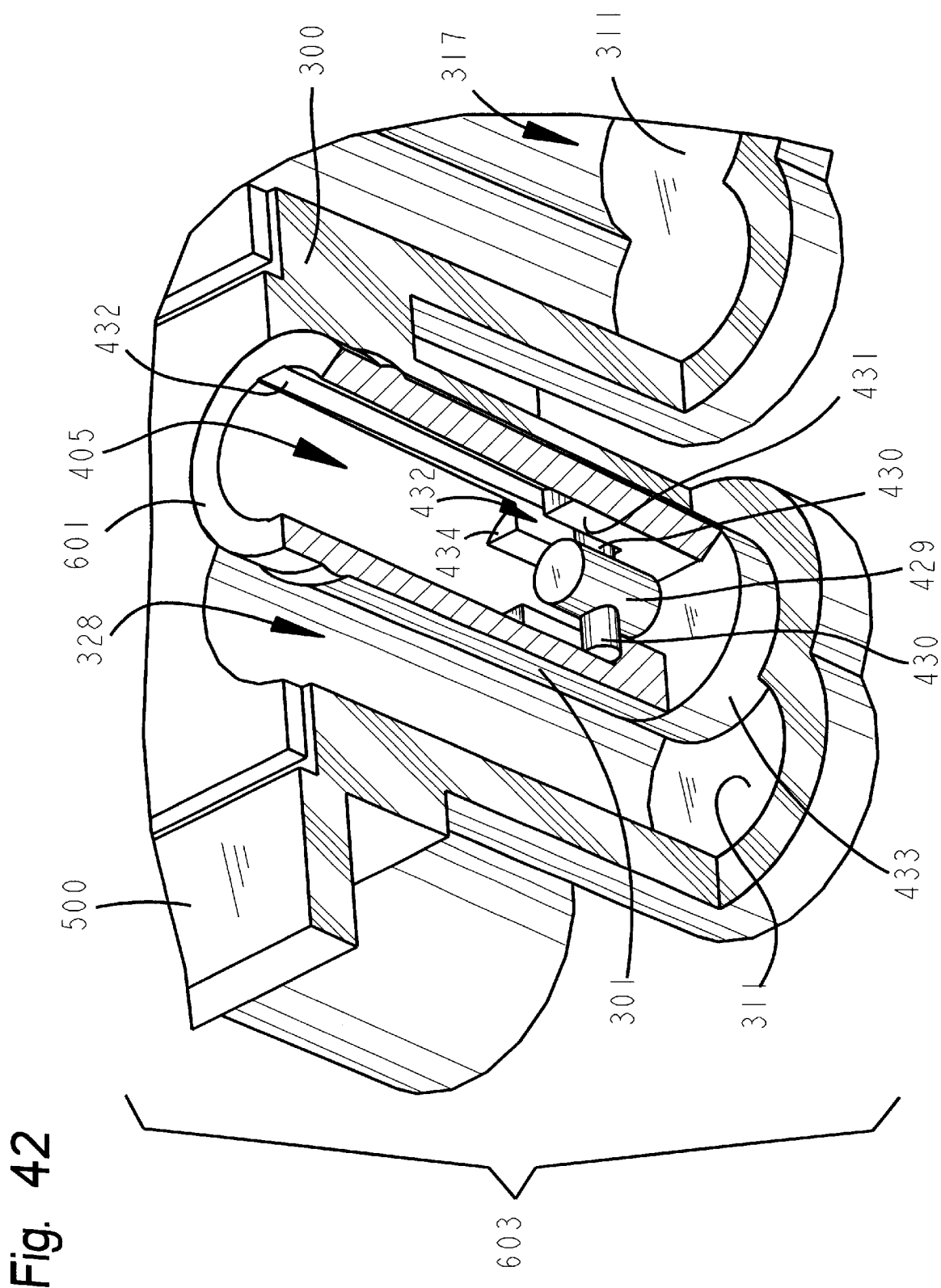
FIG. 42 is a partial isometric view with portions thereof removed of a fourth embodiment of the present invention.

FIG. 42 shows a third embodiment of disposable device 303 as disposable device 603. Disposable device 603 uses well plate 500, and replaces cup 501 with cup 601. In this embodiment, the location of the mix chamber 405 is reversed from the previous two embodiments of disposable device 303. The mix chamber 405, of this embodiment is inside cup 601. This embodiment uses a cylindrically shaped filter frit 433, instead of the toroidal filter frit 428 used in the previous embodiment. Cup 601 of this embodiment contains a protrusion on either side of the interior of cup 601, extending from the bottom of cup 601, and defined by side wall 431, and top wall 434. Both protrusions contain a slot 432. The follower magnet 429 of this embodiment contains two pins 430, the common central axis of which, intersects the central axis of follower magnet 429, and is orthogonal to the central axis of follower magnet 429, as shown in FIG. 42. The pins 430 of follower magnet 429 fit into slots 432. Well plate 500, and cup 601 should contain a key (not shown) to orient cup 601 in well plate 500, so that when disposable device 603, is assembled into constant temperature mixing and storage apparatus 342, the central axis of pins 430, will be parallel to the central axis of magnet drive shafts 344, shown in FIG. 28. The bottom of slots 343 of cup 601, should be located far enough above the top surface of filter frit 433, so that follower magnet 429 will not hit filter frit 433, as follower magnet 429 rotates about the central axis of pins 430. As follower magnet 429 rotates, it will efficiently mix resin with solution in mix chamber 405, and will also keep the surface of filter frit 433 clean, and will not damage the surface of filter frit 433. In the embodiment shown in FIG. 42, cylindrically shaped filter frit 433 could be replaced with toroidal filter frit 428 shown in FIG. 41, or it could be replaced with a filter element 302 (shown in FIG. 21), sealed to the bottom of cup 601, in which case a gap should exist between the bottom surface of the filter element and bottom wall 311 of well 317. The advantage of the disposable device 603 shown in FIG. 42, is that it is easier to assemble, and it can be fabricated from materials that are difficult to bond together, and because follower magnet 429 spins above the surface of filter frit 433, mixing is more efficient, and the surface of filter frit 433 is kept cleaner.

In any of the previous embodiments, the rotating shafts that contain the rotating permanent magnets of the reusable instrument, could be replaced with a rotating permanent magnet (not shown) located below the water bath of the reusable instrument, with the axis of rotation of said rotating permanent magnet being parallel to the central axis of the mix chambers of the disposable device, and being orthagonal to, and intersecting the centerline of said rotating permanent magnet, said centerline extending from the north pole to the south pole of said rotating permanent magnet. In this case the follower magnet within the mix chamber of the disposable device would rotate about an axis parallel to the axis of rotation of said rotating permanent magnet of said reusable instrument, and the axis of rotation of the follower magnet would be orthogonal to, and intersect the centerline of said follower magnet, said centerline of said follower magnet extending from the north pole to the south pole of said follower magnet. This would result in vortex mixing of the solution within the mix chamber.

In any of the previous embodiments of the present invention, a second follower magnet could be placed in the storage chamber of the disposable device to mix the solution in said storage chamber.

Although the present invention has been fully described by way of examples with references to the accompanying drawings, it is to be noted here that various changes and modifications will be apparent to those skilled in the art. Therefore, unless such changes and modifications depart from the scope of the present invention, they should be construed as included therein.

What is claimed:

1. A device for mixing a solvent with a solute to form a solution, and separating said solution from excess solute so that a sample of solution less excess solute can be obtained, said device comprising:

a well plate with at least one closed bottom well protruding downward from the top surface of said well plate, having a top interior profile formed by the non-overlapping portions of two overlapping circles and having a bottom interior profile formed by the non-overlapping portions of two overlapping circles with the radii of the bottom circles being equal to or less than the radii of the corresponding top circles to form a well with a nominal interior profile in the shape of a figure eight with multiple wells being arranged in an array, one cup for each of said at least one well, substantially cylindrical in shape with an open top and a closed bottom with at least one hole protruding through the bottom, with the bottom outside diameter being less than or equal to the top outside diameter with a length less than the height of said at least one well with one cup inserted into each of said at least one well with the top surface of each cup aligned with the top surface of said well plate and with the central axis of each cup aligned with the corresponding central axis of one of the circles of the top interior profile of said at least one well, a filter means capable of retaining said excess solute and capable of passing said solution disposed below said cup with the outer periphery of said filter means sealed to the outer periphery of the bottom of said cup thereby dividing said at least one well into a storage chamber contained in the interior of said cup and a mix chamber contained in the portion of the at least one well outside said cup, a permanent magnet located in the bottom portion of said mix chamber having a length less than the inside diameter of said mix chamber and rotatable about an axis substantially perpendicular to the central axis of the magnet and substantially parallel to the rotational axis of an external rotating magnetic field and rotating when driven by said external rotating magnetic field thereby efficiently mixing a solvent with a solute to form a solution in the mix chamber, one or more gas channels disposed in the top surface of said well plate for placing the mix chambers in gas flow relation with a mix gas port.

2. The device of claim 1 wherein said cup contains a ring protruding from its outer wall with the central axis of said ring coinciding with the central axis of said cup with said ring interlocked with a mating groove-in the side wall of said at least one well.

3. The device of claim 1 wherein said filter means is a cylindrically shaped frit with the top and bottom faces of said frit compressed between the bottom surface of said cup and the bottom surface of said at least one well.

4. The device of claim 1 wherein said filter means is a toroidally shaped frit with a flat top and a flat bottom, with the top and bottom faces of said frit compressed between the bottom surface of said cup and the bottom surface of said at least one well.

5. The device of claim 1 wherein said storage chamber contains a second permanent magnet located in the bottom portion of said storage chamber having a length less than the inside diameter of said storage chamber and rotatable about an axis substantially perpendicular to the central axis of the second magnet and substantially parallel to the rotational axis of said external rotating magnetic field and rotating when driven by said external rotating magnetic field thereby creating a homogenous solution in said storage chamber.

6. The device of claim 1 wherein said external magnetic field rotates about an axis parallel to the central axis of said mix chamber, thereby creating a vortex to efficiently mix the solvent with the solute to form a solution in said mix chamber.

7. An apparatus for mixing a solvent with a solute to form a solution, and separating said solution from excess solute so that a sample of solution less excess solute can be obtained, said apparatus comprising;
   a device including:
      a well plate with at least one closed bottom well protruding downward from the top surface of said well plate having a top interior profile formed by the non-overlapping portions of two overlapping circles and having a bottom interior profile formed by the non-overlapping portions of two overlapping circles with the radii of the bottom circles being equal to or less than the radii of the corresponding top circles to form a well with a nominal interior profile in the shape of a figure eight with multiple wells being arranged in an array,
      one cup for each of said at least one well, substantially cylindrical in shape with an open top and a closed bottom with at least one hole protruding through the bottom, with the bottom outside diameter being less than or equal to the top outside diameter with a length less than the height of said at least one well with one cup inserted into each of said at least one well with the top surface of each cup aligned with the top surface of said well plate and with the central axis of each cup aligned with the corresponding central axis of one of the circles of the top interior profile of said at least one well,
      a filter means capable of retaining said excess solute and capable of passing said solution disposed below said cup with the outer periphery of said filter means sealed to the outer periphery of the bottom of said cup thereby dividing said at least one well into a storage chamber contained in the interior of said cup and a mix chamber contained in the portion of the at least one well outside said cup,
      a permanent magnet located in the bottom portion of said mix chamber having a length less than the inside diameter of said mix chamber,
      one or more gas channels disposed in the top surface of said well plate said gas channels forming a communication path between said mix chambers and a mix gas port disposed in the top surface of said well plate,
   a water bath apparatus with a reservoir containing a temperature controlled liquid with said device releasably sealed to said water bath apparatus with the bottom outside portions of said at least one well immersed in said temperature controlled liquid, thereby controlling the temperature of the contents of said mix chamber and said storage chamber,
   a means to create a rotating magnetic field with the north and south poles of said magnetic field rotating about an axis normal to the central axis of said mix chamber of said device, thereby causing said permanent magnet located in the bottom portion of said mix chamber to rotate about an axis substantially perpendicular to the central axis of said magnet and substantially perpendicular to the central axis of said mix chamber, thereby efficiently mixing a solvent with a solute to form a solution in said mix chamber,
   a manifold disposed above said device, the shape of said manifold being substantially the same as the shape of the top surface of said device, with the edges of said manifold substantially aligned with the edges of the top surface of said device, said manifold containing one through hole for each storage chamber of said device with the central axis of each storage chamber of said device substantially aligned with the central axis of the corresponding through hole of said manifold with all through holes in gas flow communication with a storage gas port disposed in said manifold,
   a first sealing means releasably compressed between said device and said manifold, the shape of said first sealing means being substantially the same as the shape of the top surface of said device, with the edges of said first sealing means substantially aligned with the edges of the top surface of said device, said first sealing means containing one through hole for each storage chamber of said device with the central axis of each storage chamber of said device substantially aligned with the central axis of the corresponding through hole of said first sealing means, thereby placing each storage chamber of said device in communication with its corresponding through hole of said manifold, and thereby capping said one or more gas channels disposed in the top surface of said device, thereby placing said mix chambers of said device in gas flow communication with said mix gas port of said device,
   a top plate disposed above said manifold, the shape of said top plate being substantially the same as the shape of the top surface of said device, with the edges of said top plate substantially aligned with the edges of the top surface of said device, said top plate containing one through hole for each storage chamber of said device with the central axis of each storage chamber of said device substantially aligned with the central axis of the corresponding through hole of said top plate,
   a second sealing means releasably compressed between said top plate and said manifold, the shape of said second sealing means being substantially the same as the shape of the top surface of said device, with the edges of said second sealing means substantially aligned with the edges of the top surface of said device, said second sealing means penetrable with a needle and self sealable when said needle is withdrawn.

8. The apparatus of claim 7 wherein said cup contains a ring protruding from its outer wall with the central axis of said ring coinciding with the central axis of said cup with said ring interlocked with a mating groove in the side wall of said at least one well.

9. The apparatus of claim 7 wherein said filter means is a cylindrically shaped frit with the top and bottom faces of said frit compressed between the bottom surface of said cup and the bottom surface of said at least one well.

10. The apparatus of claim 7 wherein said storage chamber contains a second permanent magnet located in the bottom portion of said storage chamber having a length less than the inside diameter of said storage chamber and rotatable by said rotating magnetic field about an axis substantially perpendicular to the central axis of the second magnet and substantially parallel to the rotational axis of said rotating magnetic field, thereby creating a homogenous solution in said storage chamber.

11. A device for mixing a solvent with a solute to form a solution, and separating said solution from excess solute so that a sample of solution less excess solute can be obtained, said device comprising:

a well plate with at least one closed bottom well protruding downward from the top surface of said well plate, having a top interior profile formed by the non-overlapping portions of two overlapping circles and having a bottom interior profile formed by the non-overlapping portions of two overlapping circles with the radii of the bottom circles being equal to or less than the radii of the corresponding top circles to form a well with a nominal interior profile in the shape of a figure eight with multiple wells being arranged in an array, one cup for each of said at least one well, substantially cylindrical in shape with an open top and a closed bottom with at least one hole protruding through the bottom, with the bottom outside diameter being less than or equal to the top outside diameter with a length less than the height of said at least one well with one cup inserted into each of said at least one well with the top surface of each cup aligned with the top surface of said well plate and with the central axis of each cup aligned with the corresponding central axis of one of the circles of the top interior profile of said at least one well, a filter means capable of retaining said excess solute and capable of passing said solution disposed below said cup with the outer periphery of said filter means sealed to the outer periphery of the bottom of said cup thereby dividing said at least one well into a mix chamber contained in the interior of said cup and a storage chamber contained in the portion of the at least one well outside said cup, a permanent magnet located in the bottom portion of said mix chamber having a length less than the inside diameter of said mix chamber and rotatable about an axis substantially perpendicular to the central axis of the magnet and substantially parallel to the rotational axis of an external rotating magnetic field and rotating when driven by said external rotating magnetic field thereby efficiently mixing a solvent with a solute to form a solution in the mix chamber, one or more gas channels disposed in the top surface of said well plate for placing the storage chambers in gas flow relation with a storage gas port.

12. The device of claim 11 wherein said cup contains a ring protruding from its outer wall with the central axis of said ring coinciding with the central axis of said cup with said ring interlocked with a mating groove in the side wall of said at least one well.

13. The device of claim 11 wherein said filter means is a cylindrically shaped frit with the top and bottom faces of said frit compressed between the bottom surface of said cup and the bottom surface of said at least one well.

14. The device of claim 11 wherein said filter means is a toroidally shaped frit with a flat top and a flat bottom, with the top and bottom faces of said frit compressed between the bottom surface of said cup and the bottom surface of said at least one well.

15. The device of claim 11 wherein said storage chamber contains a second permanent magnet located in the bottom portion of said storage chamber having a length less than the inside diameter of said storage chamber and rotatable about an axis substantially perpendicular to the central axis of the second magnet and substantially parallel to the rotational axis of said external rotating magnetic field and rotating when driven by said external rotating magnetic field thereby creating a homogenous solution in said storage chamber.

16. A multi-well device comprising:

a well plate with at least one well, the interior side walls of said at least one well protruding downward from the top surface of said well plate, said at least one well having an open top a closed bottom and an interior profile taken through a plane parallel to said top surface formed by the non-overlapping portions of two overlapping closed planar curves, with multiple wells arranged in an array, one cup for each of said at least one well, said cup having an open top, a closed bottom, and at least one hole protruding through said closed bottom, the outside wall of said cup shaped to fit into a portion of said at least one well, with the length of said cup being less than the height of said at least one well, with one cup inserted into a portion of each of said at least one well with the top surface of each cup substantially aligned with the top surface of said well plate, a filter means disposed below said cup, said filter means sealed to the bottom of said cup with the inner periphery of the seal enclosing said at least one hole, said filter means thereby dividing said at least one well into a first chamber contained in the interior of said cup and a second chamber contained in the portion of the at least one well outside said cup.

17. The multi-well device, of claim 16 wherein one or more gas channels are disposed in the top surface of said well plate for placing the second chambers in gas flow relation with a mix gas port.

18. The multi-well device of claim 16 wherein the outer edges of said well plate form a rectangle.

19. The multi-well device of claim 16 wherein said array is a row by column matrix.

20. The multi-well device of claim 16 wherein said two overlapping closed planar curves are two overlapping circles.

21. The multi-well device of claim 20 wherein the outside wall of said cup is substantially cylindrical in shape, with the central axis of each cup aligned with the corresponding central axis of one of the circles of said interior profile.

22. The multi-well device of claim 21 wherein said at least one well contains a groove in at least a portion of the interior side wall of said at least one well with the central axis of said groove aligned with the central axis of one of the circles of said interior profile.

23. The multi-well device of claim 22 wherein each cup contains a ring protruding from its outer wall with the central axis of said ring coinciding with the central axis of said cup, with said ring interlocked with its corresponding groove in said at least one well.

24. The multi-well device of claim 23 wherein said filter means is a cylindrically shaped frit with the top and bottom faces of said frit compressed between the bottom surface of said cup and the bottom surface of said at least one well.

25. The multi-well device of claim 23 wherein said filter means is a toroidally shaped frit with a flat top and a flat bottom, with the top and bottom faces of said frit compressed between the bottom surface of said cup and the bottom surface of said at least one well.

26. The multi-well device of claim 24 wherein said multi-well device is disposable.

27. The multi-well device of claim 25 wherein said multi-well device is disposable.

28. An apparatus for mixing a solvent with a solute to form a solution, and separating said solution from excess solute so that a sample of solution less excess solute can be obtained, said apparatus comprising:

a multi-well device including:
a well plate with at least one well, the interior side walls of said at least one well protruding downward from the top surface of said well plate, said at least one well having an open top a closed bottom and an interior profile taken through a plane parallel to said top surface formed by the non-overlapping portions of two overlapping closed planar curves, with multiple wells arranged in an array,
one cup for each of said at least one well, said cup having an open top, a closed bottom, and at least one hole protruding through said closed bottom, the outside wall of said cup shaped to fit into a portion of said at least one well, with the length of said cup being less than the height of said at least one well, with one cup inserted into a portion of each of said at least one well with the top surface of each cup substantially aligned with the top surface of said well plate,
a filter means disposed below said cup, said filter means sealed to the bottom of said cup with the inner periphery of the seal enclosing said at least one hole, said filter means thereby dividing said at least one well into a first chamber contained in the interior of said cup and a second chamber contained in the portion of the at least one well outside said cup,
one or more gas channels disposed in the top surface of said well plate for placing the second chambers in gas flow relation with a mix gas port, a water bath apparatus with a reservoir containing a temperature controlled liquid with said multi-well device releasably sealed to said water bath apparatus with the bottom outside portion of said at least one well immersed in said temperature controlled liquid, thereby controlling the temperature of the contents of said first chamber and said second chamber, a manifold disposed above said multi-well device, said manifold containing one through hole for each first chamber of said multi-well device with the central axis of each first chamber of said multi-well device substantially aligned with the central axis of the corresponding through hole of said manifold with all through holes in gas flow communication with a storage gas port disposed in said manifold, a first sealing means releasably compressed between said multi-well device and said manifold, said first sealing means containing one through hole for each first chamber of said multi-well device with the central axis of each first chamber of said multi-well device substantially aligned with the central axis of the corresponding through hole of said first sealing means, thereby placing each first chamber of said multi-well device in communication with its corresponding through hole of said manifold, and thereby capping said one or more gas channels, thereby placing said second chambers of said multi-well device in gas flow communication with said mix gas port of said multi-well device, a top plate disposed above said manifold, said top plate containing one through hole for each first chamber of said multi-well device with the central axis of each first chamber of said multi-well device substantially aligned with the central axis of the corresponding through hole of said top plate, a second sealing means releasably compressed between said top plate and said manifold, said second sealing means penetrable with a needle and self sealable when said needle is withdrawn.

29. The apparatus of claim 28 wherein said apparatus contains a means to create a rotating magnetic field, with the north and south poles of said magnetic field rotating about a driver axis parallel to said top surface of said well plate.

30. The apparatus of claim 29 wherein a permanent magnet is located in the bottom portion of said second chamber, thereby making said second chamber a mix chamber and said first chamber a storage chamber, said permanent magnet having a length less than or equal to the maximum length that can be rotated about a follower axis perpendicular to the central axis of the magnet and substantially parallel to said driver axis, and rotating about said follower axis when driven by said rotating magnetic field, thereby efficiently mixing a solvent with a solute to form a solution in the mix chamber.

31. The apparatus of claim 30 wherein a second permanent magnet is located in the bottom portion of said first chamber, said second permanent magnet having a length less than or equal to the maximum length that can be rotated about a second follower axis perpendicular to the central axis of the second magnet and substantially parallel to said driver axis, and rotating about said second follower axis when driven by said rotating magnetic field, said second permanent magnet used to further mix the solution in said storage chamber prior to taking a sample of said solution from said storage chamber.

32. The apparatus of claim 28 wherein said apparatus contains a means to create a rotating magnetic field, with the north and south poles of said magnetic field rotating about a driver axis normal to said top surface of said well plate.

33. The apparatus of claim 32 wherein a permanent magnet is located in the bottom portion of said second chamber, thereby making said second chamber a mix chamber and said first chamber a storage chamber, said permanent magnet having a length less than or equal to the maximum length that can be rotated about a follower axis perpendicular to the central axis of the magnet and substantially parallel to said driver axis, and rotating about said follower axis when driven by said rotating magnetic field, thereby efficiently mixing a solvent with a solute to form a solution in the mix chamber.

34. The apparatus of claim 33 wherein a second permanent magnet is located in the bottom portion of said first chamber, said second permanent magnet having a length less than or equal to the maximum length that can be rotated about a second follower axis perpendicular to the central axis of the second magnet and substantially parallel to said driver axis, and rotating about said second follower axis when driven by said rotating magnetic field, said second permanent magnet used to further mix the solution in said storage chamber prior to taking a sample of said solution from said storage chamber.

35. An apparatus for synthesizing drug compounds by mixing a solution with a resin and separating said solution from said resin so that the solution can be removed from said apparatus comprising;
- a multi-well device including:
  - a well plate with at least one well, the interior side walls of said at least one well protruding downward from the top surface of said well plate, said at least one well having an open top a closed bottom and an interior profile taken through a plane parallel to said top surface formed by the non-overlapping portions of two overlapping closed planar curves, with multiple wells arranged in an array,
  - one cup for each of said at least one well, said cup having an open top, a closed bottom, and at least one hole protruding through said closed bottom, the outside wall of said cup shaped to fit into a portion of said at least one well, with the length of said cup being less than the height of said at least one well, with one cup inserted into a portion of each of said at least one well with the top surface of each cup substantially aligned with the top surface of said well plate,
  - a filter means disposed below said cup, said filter means sealed to the bottom of said cup with the inner periphery of the seal enclosing said at least one hole, said filter means thereby dividing said at least one well into a first chamber contained in the interior of said cup and a second chamber contained in the portion of the at least one well outside said cup,
  - one or more gas channels disposed in the top surface of said well plate for placing the second chambers in gas flow relation with a mix gas port,
- a water bath apparatus with a reservoir containing a temperature controlled liquid with said multi-well device releasably sealed to said water bath apparatus with the bottom outside portion of said at least one well immersed in said temperature controlled liquid, thereby controlling the temperature of the contents of said first chamber and said second chamber,
- a manifold disposed above said multi-well device, said manifold containing one through hole for each first chamber of said multi-well device with the central axis of each first chamber of said multi-well device substantially aligned with the central axis of the corresponding through hole of said manifold with all through holes in gas flow communication with a storage gas port disposed in said manifold,
- a first sealing means releasably compressed between said multi-well device and said manifold, said first sealing means containing one through hole for each first chamber of said multi-well device with the central axis of each first chamber of said multi-well device substantially aligned with the central axis of the corresponding through hole of said first sealing means, thereby plating each first chamber of said multi-well device in communication with its corresponding through hole of said manifold, and thereby capping said one or more gas channels, thereby placing said second chambers of said multi-well device in gas flow communication with said mix gas port of said multi-well device,
- a top plate disposed above said manifold, said top plate containing one through hole for each first chamber of said multi-well device with the central axis of each first chamber of said multi-well device substantially aligned with the central axis of the corresponding through hole of said top plate,
- a second sealing means releasably compressed between said top plate and said manifold, said second sealing means penetrable with a needle and self sealable when said needle is withdrawn.

36. The apparatus of claim 35 wherein said apparatus contains a meats to create a rotating magnetic field, with the north and south poles of said magnetic field rotating about a driver axis parallel to said top surface of said well plate.

37. The apparatus of claim 36 wherein a permanent magnet is located in the bottom portion of said second chamber, thereby making said second chamber a mix chamber and said first chamber a storage chamber, said permanent magnet having a length less than or equal to the maximum length that can be rotated about a follower axis perpendicular to the central axis of the magnet and substantially parallel to said driver axis, and rotating about said follower axis when driven by said rotating magnetic field, thereby efficiently mixing a solution with a resin in the mix chamber.

38. The apparatus of claim 35 wherein said apparatus contains a means to create a rotating magnetic field, with the north and south poles of said magnetic field rotating about a driver axis normal to said top surface of said well plate.

39. The apparatus of claim 38 wherein a permanent magnet is located in the bottom portion of said second chamber, thereby making said second chamber a mix chamber and said first chamber a storage chamber, said permanent magnet having a length less than or equal to the maximum length that can be rotated about a follower axis perpendicular to the central axis of the magnet and substantially parallel to said driver axis, and rotating about said follower axis when driven by said rotating magnetic field, thereby creating a vortex to efficiently mix a solution with a resin in the mix chamber.

* * * * *